US008208993B2

(12) United States Patent
Piferi et al.

(10) Patent No.: US 8,208,993 B2
(45) Date of Patent: *Jun. 26, 2012

(54) IMAGING DEVICE FOR MRI-GUIDED MEDICAL INTERVENTIONAL SYSTEMS

(75) Inventors: Peter Piferi, Orange, CA (US); Christopher Keidl, Hartland, WI (US); David M. Peterson, Archer, FL (US); David Sayler, Portland, OR (US)

(73) Assignee: MRI Interventions, Inc., Memphis, TN (US)

( * ) Notice: Subject to any disclaimer, the term of this patent is extended or adjusted under 35 U.S.C. 154(b) by 715 days.

This patent is subject to a terminal disclaimer.

(21) Appl. No.: 12/237,033

(22) Filed: Sep. 24, 2008

(65) Prior Publication Data
US 2009/0112082 A1    Apr. 30, 2009

Related U.S. Application Data

(63) Continuation-in-part of application No. 12/134,412, filed on Jun. 6, 2008.

(60) Provisional application No. 60/974,821, filed on Sep. 24, 2007, provisional application No. 60/933,641, filed on Jun. 7, 2007.

(51) Int. Cl.
*A61B 5/05* (2006.01)

(52) U.S. Cl. ........ 600/426; 600/407; 600/427; 600/429; 600/410

(58) Field of Classification Search .................. 600/407, 600/410, 426, 427, 429
See application file for complete search history.

(56) References Cited

U.S. PATENT DOCUMENTS

| 4,051,845 A | 10/1977 | Collins |
| 4,209,258 A | 6/1980 | Oakes |
| 4,276,697 A | 7/1981 | Drake et al. |
| 4,319,136 A | 3/1982 | Jinkins |
| 4,386,602 A | 6/1983 | Sheldon et al. |

(Continued)

FOREIGN PATENT DOCUMENTS

DE    19625834 A1    1/1998

(Continued)

OTHER PUBLICATIONS

Invitation to Pay Additional Fees and Partial Search Report for corresponding PCT Application Serial No. PCT/US2008/011040 issued by the European Patent Office on Dec. 19, 2008.

(Continued)

*Primary Examiner* — Brian Casler
*Assistant Examiner* — Joel Lamprecht
(74) *Attorney, Agent, or Firm* — Myers Bigel Sibley & Sajovec, P.A.

(57) ABSTRACT

An MRI-guided interventional system includes a head support apparatus for engaging and securing the head of a patient, and a targeting frame configured to be secured to the body of a patient. The targeting frame includes a cooperating targeting cannula that is configured to guide placement of an interventional device through a burr hole in a patient's skull in vivo. The system includes an MRI-compatible camera positioned proximate to the head support apparatus, and an MRI-compatible imaging device having one end attached to the targeting frame to provide a local field of view of the burr hole, and an opposite end in communication with the camera. The system also includes a display output module coupled to the camera for receiving electrical signals therefrom and for displaying images corresponding thereto.

20 Claims, 44 Drawing Sheets

U.S. PATENT DOCUMENTS

| | | | |
|---|---|---|---|
| 4,838,265 A | 6/1989 | Cosman et al. | |
| 5,125,888 A | 6/1992 | Howard et al. | |
| 5,154,723 A | 10/1992 | Kubota et al. | |
| 5,342,356 A | 8/1994 | Ellman et al. | |
| 5,469,847 A | 11/1995 | Zinreich et al. | |
| 5,638,819 A | 6/1997 | Manwaring et al. | |
| 5,655,084 A | 8/1997 | Pinsky et al. | |
| 5,695,501 A | 12/1997 | Carol et al. | |
| 5,697,958 A | 12/1997 | Paul et al. | |
| 5,699,801 A | 12/1997 | Atalar et al. | |
| 5,707,335 A | 1/1998 | Howard et al. | |
| 5,728,079 A | 3/1998 | Weber et al. | |
| 5,776,144 A | 7/1998 | Leysieffer et al. | |
| 5,779,694 A | 7/1998 | Howard et al. | |
| 5,855,582 A | 1/1999 | Gildenberg | |
| 5,928,145 A | 7/1999 | Ocali et al. | |
| 5,961,455 A | 10/1999 | Daum et al. | |
| 5,971,984 A | 10/1999 | Taylor et al. | |
| 5,993,463 A | 11/1999 | Truwit | |
| 6,006,126 A | 12/1999 | Cosman | |
| 6,050,992 A | 4/2000 | Nichols | |
| 6,167,292 A | 12/2000 | Badano et al. | |
| 6,167,311 A | 12/2000 | Rezai | |
| 6,195,577 B1 | 2/2001 | Truwit et al. | |
| 6,206,890 B1 | 3/2001 | Truwit | |
| 6,216,030 B1 | 4/2001 | Howard et al. | |
| 6,263,229 B1 | 7/2001 | Atalar et al. | |
| 6,264,607 B1 | 7/2001 | Goll et al. | |
| 6,267,769 B1 | 7/2001 | Truwit | |
| 6,267,770 B1 | 7/2001 | Truwit | |
| 6,273,896 B1 | 8/2001 | Franck et al. | |
| 6,282,437 B1 | 8/2001 | Franck et al. | |
| 6,284,971 B1 | 9/2001 | Atalar et al. | |
| 6,298,262 B1 | 10/2001 | Franck et al. | |
| 6,351,662 B1 | 2/2002 | Franck et al. | |
| 6,356,786 B1 | 3/2002 | Rezai et al. | |
| 6,368,329 B1 | 4/2002 | Truwit | |
| 6,405,079 B1 | 6/2002 | Ansarinia | |
| 6,419,680 B1 | 7/2002 | Cosman et al. | |
| 6,438,423 B1 | 8/2002 | Rezai et al. | |
| 6,526,318 B1 | 2/2003 | Ansarinia | |
| 6,529,765 B1 | 3/2003 | Franck et al. | |
| 6,539,263 B1 | 3/2003 | Schiff et al. | |
| 6,584,351 B1 | 6/2003 | Ekwall | |
| 6,591,128 B1 * | 7/2003 | Wu et al. | 600/422 |
| 6,606,513 B2 | 8/2003 | Lardo et al. | |
| 6,609,030 B1 | 8/2003 | Rezai et al. | |
| 6,628,980 B2 | 9/2003 | Atalar et al. | |
| 6,675,033 B1 | 1/2004 | Lardo et al. | |
| 6,701,176 B1 | 3/2004 | Halperin et al. | |
| 6,708,064 B2 | 3/2004 | Rezai | |
| 6,725,080 B2 | 4/2004 | Melkent et al. | |
| 6,725,092 B2 | 4/2004 | MacDonald et al. | |
| 6,752,812 B1 | 6/2004 | Truwit | |
| 6,772,000 B2 | 8/2004 | Talpade | |
| 6,782,288 B2 | 8/2004 | Truwit et al. | |
| 6,904,307 B2 | 6/2005 | Karmarkar et al. | |
| 7,022,082 B2 | 4/2006 | Sonek | |
| 7,155,316 B2 * | 12/2006 | Sutherland et al. | 700/248 |
| 7,167,760 B2 | 1/2007 | Dawant et al. | |
| 7,217,276 B2 | 5/2007 | Henderson et al. | |
| 7,235,084 B2 | 6/2007 | Skakoon et al. | |
| 7,313,430 B2 | 12/2007 | Urquhart et al. | |
| 7,602,190 B2 * | 10/2009 | Piferi et al. | 324/318 |
| 2001/0004676 A1 | 6/2001 | Ouchi | |
| 2001/0014771 A1 | 8/2001 | Truwit et al. | |
| 2001/0027271 A1 * | 10/2001 | Franck et al. | 600/426 |
| 2001/0047126 A1 | 11/2001 | Nagai et al. | |
| 2001/0053879 A1 | 12/2001 | Mills et al. | |
| 2002/0010479 A1 | 1/2002 | Skakoon et al. | |
| 2002/0019641 A1 | 2/2002 | Truwit | |
| 2002/0049451 A1 | 4/2002 | Parmer et al. | |
| 2002/0052610 A1 | 5/2002 | Skakoon et al. | |
| 2003/0028095 A1 | 2/2003 | Tulley et al. | |
| 2003/0050557 A1 | 3/2003 | Susil et al. | |
| 2003/0055436 A1 | 3/2003 | Daum et al. | |
| 2003/0120143 A1 | 6/2003 | Franklin et al. | |
| 2003/0205233 A1 | 11/2003 | Aboul-Hosn et al. | |
| 2004/0046557 A1 | 3/2004 | Karmarkar et al. | |
| 2004/0064148 A1 | 4/2004 | Daum et al. | |
| 2004/0092810 A1 | 5/2004 | Daum et al. | |
| 2004/0167393 A1 | 8/2004 | Solar et al. | |
| 2004/0167543 A1 | 8/2004 | Mazzocchi et al. | |
| 2004/0215279 A1 | 10/2004 | Houben et al. | |
| 2004/0228796 A1 | 11/2004 | Talpade | |
| 2004/0267284 A1 | 12/2004 | Parmer et al. | |
| 2005/0004453 A1 | 1/2005 | Tearney et al. | |
| 2005/0049486 A1 * | 3/2005 | Urquhart et al. | 600/429 |
| 2005/0070781 A1 | 3/2005 | Dawant et al. | |
| 2005/0222647 A1 | 10/2005 | Wahlstrand et al. | |
| 2006/0192319 A1 | 8/2006 | Solar | |
| 2006/0195119 A1 | 8/2006 | Mazzocchi et al. | |
| 2006/0229641 A1 | 10/2006 | Gupta et al. | |
| 2006/0252314 A1 | 11/2006 | Atalar et al. | |
| 2007/0106305 A1 | 5/2007 | Kao et al. | |
| 2007/0118049 A1 | 5/2007 | Viola | |
| 2008/0039709 A1 | 2/2008 | Karmarkar | |
| 2008/0097193 A1 * | 4/2008 | Karmarkar | 600/423 |
| 2008/0306375 A1 | 12/2008 | Sayler et al. | |

FOREIGN PATENT DOCUMENTS

| | | |
|---|---|---|
| DE | 10029736 A1 | 1/2002 |
| DE | 100 29 737 | 5/2003 |
| EP | 1 524 626 | 4/2005 |
| WO | WO 98/52064 A | 11/1998 |
| WO | WO 03/102614 A | 12/2003 |
| WO | WO 2004/029782 | 4/2004 |
| WO | WO 2004/058086 A1 | 7/2004 |
| WO | WO 2006/081409 A2 | 8/2006 |
| WO | WO 2006/099475 A2 | 9/2006 |
| WO | WO 2007/064739 | 6/2007 |
| WO | WO 2007/106558 A2 | 9/2007 |

OTHER PUBLICATIONS

Notification of Transmittal of the International Search Report and the Written Opinion of the International Searching Authority, or the Declaration for corresponding PCT Application No. PCT/US2008/011051 mailed Feb. 11, 2009.

Baker et al., Neurostimulation systems: assessment of magnetic field interactions associated with 1.5- and 3-Tesla MR systems, J Magn Reson Imaging, 2005, 72-77, 21(1).

Bhidayasiri et al., Bilateral neurostimulation systems used for deep brain stimulation: in vitro study of MRI-related heating at 1.5 T and implications for clinical imaging of the brain, Magn Reson Imaging, 2005, 549-555, 23(4).

Buchli et al., Increased RF power absorption in MR imaging due to RF coupling between body coil and surface coil, Magn Reson Med, 1989, 105-112, 9(1).

Chou et al., RF heating of implanted spinal fusion stimulator during magnetic resonance imaging, IEEE Trans Biomed Eng, 1997, 367-373, 44(5).

Dorward et al., Accuracy of true frameless stereotaxy: in vivo measurement and laboratory phantom studies, J. Neurosurg., 1999, 90:160-168.

Francel, Nexframe System, Bilateral Active Lead Delivery to STN Using NEXFRAME, Oklahoma University Presbyterian Hospital, Image-Guided Neurolgics.

Grimson et al., An automatic registration method for frameless stereotaxy, image guided surgery, and visualization, IEEE Tran on Medical Imaging, Apr. 1996, 129-140.

Hall et al., Brian biopsy sampling by using prospective stereotaxis and a trajectory guide, J. Neurosurg., 2001, 94:67-71.

Jorgensen, Erik, Brain Image Analysis Team Joins SCI Institute, http://www.sci.utah.edu/stories/2007/Gerig_NeuroimageAnalysis.html, (2007), 3 Pages.

Ladd et al., Reduction of resonant RF heating in intravascular catheters using coaxial chokes, Magn Reson Med, 2000, 615-619, 43(4).

Liu et al., Remotely-Controlled Approach for Stereotactic Neurobiopsy, Computer Aided Surgery, 2002, 7:237-247.

Luechinger et al., In vivo heating of pacemaker leads during magnetic resonance imaging, Eur Heart J, 2005, 376-383, 26(4).

Martin et al., Placement of Deep Brain Stimulator Electrodes Using Real-Time High-Field Interventional Magnetic Resonance Imaging, Magnetic Resonance in Medicine, 2005, 54:1107-1114.

Martin, Can cardiac pacemakers and magnetic resonance imaging systems co-exist?, Eur Heart J, 2005, 325-327, 26(4).

Rezai et al., Neurostimulators: potential for excessive heating of deep brain stimulation electrodes during magnetic resonance imaging, J Magn Reson Imaging, 2001, 488-489, 14(4).

Sauser, Brittany, A 3-D View of the Brain, http://www.technologyreview.com/Biotech/19140, Aug. 6, 2007, 3 Pages.

Smith et al., The Neurostation—A Highly Accurate, Minimally Invasive Solution to Frameless Stereotactic Neurosurgery, Computerized Medical Imaging and Graphics, 1994, 247-256, 18(4).

STarFix™—Dr. Joel Franck and FHC engineer Ron Franklin—creators, www.tgt.vanderbilt.edu/reu2/REU2002/chris.ppt.

Tear Away Introducer Sets (INTREDYN), B. Braun Medical, Inc. http://www.bbraunusa.com.

Truwit et al., Prospective Stereotaxy: A Novel Method of Trajectory Alignment Using Real-Time Image Guidance, J. Magn. Reson. Imag., 2001, 13:452-457.

Willems et al., Frameless Stereotaxy, VHL Family Alliance, http://www.vhl.org/newsletter/vhl2000/00aefrst.htm.

Wirtz et al., Image-Guided Neurosurgery with Intraoperative MRI: Update of Frameless Stereotaxy and Radicality Control, Sterotact Funct Neurosurg 1997, 68:39-43.

Yoda, Decoupling technique for transmit coils in NMR spectroscopy and imaging, NMR Biomed, 1990, 27-30, 3(1).

Notification of Transmittal of the International Search Report and the Written Opinion of the International Searching Authority, or the Declaration for corresponding PCT Application No. PCT/US2008/007169 mailed Mar. 12, 2009.

Notification of Transmittal of the International Search Report and the Written Opinion of the International Searching Authority, or the Declaration for corresponding PCT Application No. PCT/US2008/011050 mailed Mar. 10, 2009.

Notification of Transmittal of the International Search Report and the Written Opinion of the International Searching Authority, or the Declaration for corresponding PCT Application No. PCT/US2008/011040 mailed Apr. 27, 2009.

Lin et al., "A Wavelet-Based Approximation of Surface Coil Sensitivity Profiles for Correction of Image Intensity Inhomogeneity and Parallel Imaging Reconstruction," Human Brain Mapping 19:96-111 (2003).

Singh et al., "Accurate Intensity Correction for Endorectal Surface Coil MR Imaging of the Prostate," IEEE Xplore, 1307-1309 (1993).

Notification of Transmittal of the International Search Report and the Written Opinion of the International Searching Authority issued on Jun. 24, 2009 by the European Patent Office for a corresponding PCT application No. PCT/US2008/011050.

Invitation to Pay Additional Fees and Partial Search Report for corresponding PCT Application Serial No. PCT/US2008/007169 issued by the European Patent Office on Nov. 19, 2008.

* cited by examiner

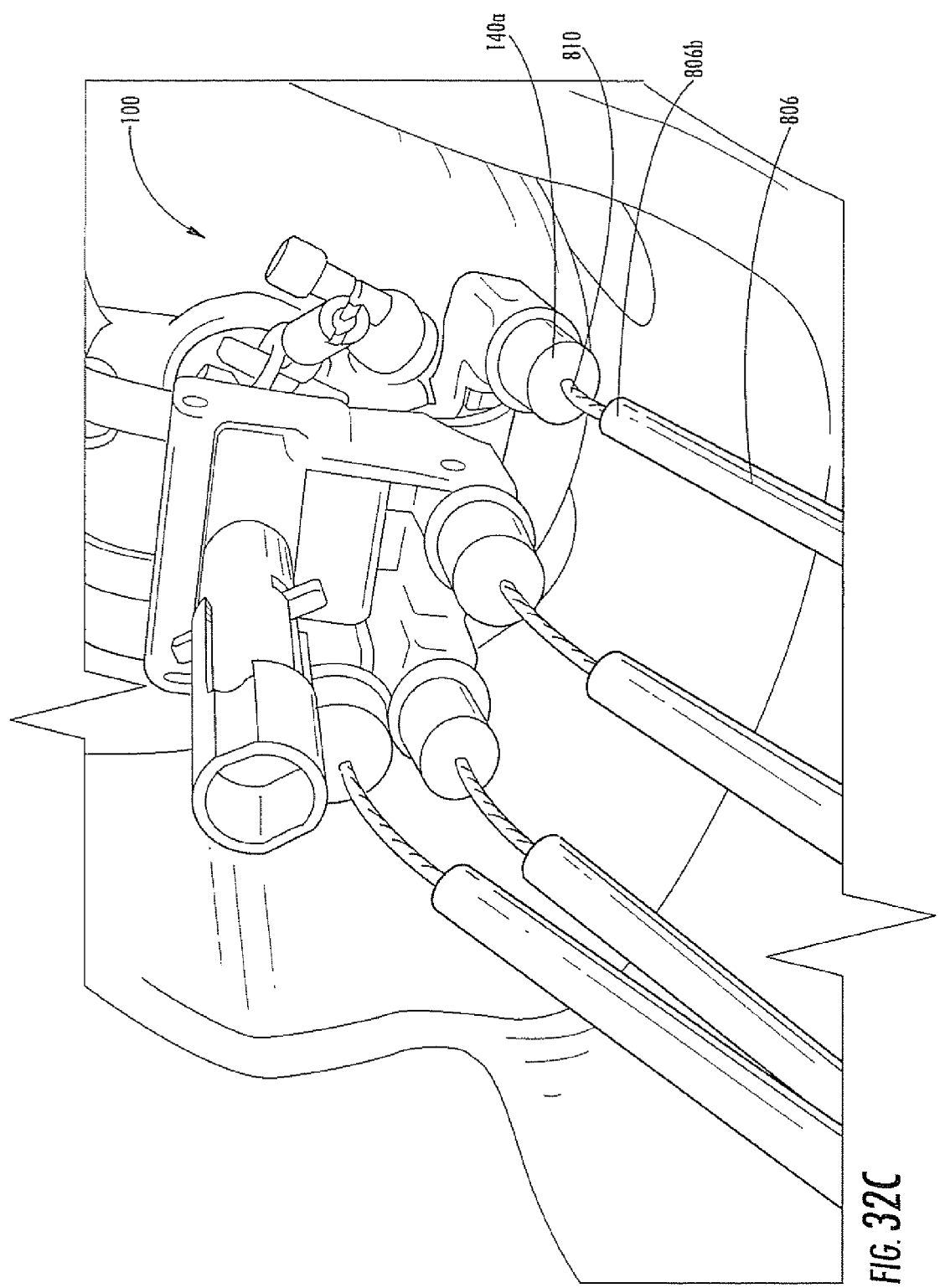

IMAGING DEVICE FOR MRI-GUIDED MEDICAL INTERVENTIONAL SYSTEMS

RELATED APPLICATIONS

This application is a continuation-in-part application of U.S. patent application Ser. No. 12/134,412, filed Jun. 6, 2008, which claims the benefit of and priority to U.S. Provisional Patent Application No. 60/974,821, filed Sep. 24, 2007, and to U.S. Provisional Patent Application No. 60/933,641, filed Jun. 7, 2007, the disclosures of which are incorporated herein by reference as if set forth in their entireties.

FIELD OF THE INVENTION

The present invention relates generally to medical systems and methods and, more particularly, to in vivo medical systems and methods.

BACKGROUND

Deep Brain Stimulation (DBS) is becoming an acceptable therapeutic modality in neurosurgical treatment of patients suffering from chronic pain, Parkinson's disease or seizure, and other medical conditions. Other electro-stimulation therapies have also been carried out or proposed using internal stimulation of the sympathetic nerve chain and/or spinal cord, etc. One example of a prior art DBS system is the Activa® system from Medtronic, Inc. The Activa® system includes an implantable pulse generator stimulator that is positioned in the chest cavity of the patient and a lead with axially spaced apart electrodes that is implanted with the electrodes disposed in neural tissue. The lead is tunneled subsurface from the brain to the chest cavity connecting the electrodes with the pulse generator. These leads can have multiple exposed electrodes at the distal end that are connected to conductors which run along the length of the lead and connect to the pulse generator placed in the chest cavity.

It is believed that the clinical outcome of certain medical procedures, particularly those using DBS, may depend on the precise location of the electrodes that are in contact with the tissue of interest. For example, to treat Parkinson's tremor, presently the DBS probes are placed in neural tissue with the electrodes transmitting a signal to the thalamus region of the brain. DBS stimulation leads are conventionally implanted during a stereotactic surgery, based on pre-operative MRI and CT images. These procedures can be long in duration and may have reduced efficacy as it has been reported that, in about 30% of the patients implanted with these devices, the clinical efficacy of the device/procedure is less than optimum. Notwithstanding the above, there remains a need for alternative MRI-guided interventional tools for DBS, as well as for other interventional medical procedures.

SUMMARY

In view of the above, MRI-guided interventional systems and methods are provided. Embodiments of the present invention provide methods, devices and systems for highly localized placement and/or delivery of diagnostic or therapeutic devices or substances.

According to embodiments of the present invention, an MRI-guided interventional system includes a targeting frame with a cooperating targeting cannula. The frame is configured to be secured to the body of a patient, and is configured to translate and rotate such that the targeting cannula can be positioned to a desired intrabody trajectory. The frame may include one or more MRI-visible fiducial markers that allow frame location/orientation to be determined within an MRI image.

Embodiments of the present invention may be particularly suitable for placing neuro-modulation leads, such as Deep Brain Stimulation ("DBS") leads, implantable parasympathetic or sympathetic nerve chain leads and/or CNS stimulation leads, as well as other devices within the brain.

Embodiments of the present invention may be suitable for a number of interventional procedures in many locations inside the body including, but not limited to, brain, cardiac, spinal, urethral, and the like. Embodiments of the present invention may be suitable for a number of MRI-guided drug delivery procedures, MRI-guided ablation procedures, etc.

A plurality of user-activatable actuators are operably connected to the frame and are configured to translate and rotate the frame relative to the body of a patient so as to position the targeting cannula to a desired intrabody trajectory. In some embodiments, the actuators are dials or thumbscrew-type devices that allow manual manipulation thereof. In other embodiments, the actuators are manipulated remotely using remote controls and cables.

The targeting cannula includes an axially-extending guide bore therethrough that is configured to guide placement of an interventional device in vivo. Various instrumentation and equipment (e.g., stimulation leads, ablation probes or catheters, injection or fluid delivery devices, biopsy needles, extraction tools, etc.) can be inserted through the targeting cannula to execute diagnostic and/or surgical procedures.

According to some embodiments of the present invention, the frame includes a base, a yoke movably mounted to the base and that is rotatable about a roll axis, and a platform movably mounted to the yoke and that is rotatable about a pitch axis. The platform includes an X-Y support table that is configured to move in an X-direction and Y-direction relative to the platform. The base has a patient access aperture formed therein, and is configured to be secured to the body of a patient such that the aperture overlies an opening in the body. A roll actuator is operably connected to the yoke and is configured to rotate the yoke about the roll axis. A pitch actuator is operably connected to the platform and is configured to rotate the platform about the pitch axis. An X-direction actuator is operably connected to the platform and is configured to move the X-Y support table in the X-direction. A Y-direction actuator is operably connected to the platform and is configured to move the X-Y support table in the Y-direction.

The base may include a plurality of locations for attachment to a body of a patient via fasteners. In some embodiments, one or more attachment locations may include multiple adjacent apertures configured to receive a fastener therethrough. For embodiments where the frame is configured to be attached to the skull of a patient, the base can be configured to be secured to the skull of a patient such that the patient access aperture overlies a burr hole formed in the patient skull.

According to some embodiments of the present invention, the yoke includes a pair of spaced apart arcuate arms. The platform engages and moves along the yoke arcuate arms when rotated about the pitch axis. The base includes at least one arcuate arm. The yoke engages and moves along the base arcuate arm when rotated about the roll axis.

According to some embodiments of the present invention, at least one of the yoke arcuate arms includes a thread pattern formed in a surface thereof. The pitch actuator includes a rotatable worm with teeth configured to engage the thread pattern. Rotation of the worm causes the platform to rotate about the pitch axis. Similarly, at least one of the base arcuate arms includes a thread pattern formed in a surface thereof. The roll actuator includes a rotatable worm with teeth configured to engage the thread pattern, and wherein rotation of the worm causes the yoke to rotate about the roll axis.

In some embodiments, the actuators are color-coded such that each different actuator has a respective different color. This allows a user to quickly determine which actuator is the correct one for a particular desired movement of the frame.

According to some embodiments of the present invention, an ergonomic remote control unit is provided that allows a user to remotely translate and rotate the frame such that the targeting cannula can be positioned to a desired intrabody trajectory. The remote control unit includes a plurality of position controls. Each control is operably connected to a respective frame actuator by a respective cable. One or more of the position controls can include both "gross" and "fine" adjustments.

Movement of a position control operates a respective actuator via a respective control cable. For example, the remote control unit includes a roll adjustment control, a pitch adjustment control, an X-direction adjustment control, and a Y-direction adjustment control. A roll control cable is operably connected to the roll adjustment control and to the roll actuator. Movement of the roll adjustment control operates the roll actuator via the roll control cable. A pitch control cable is operably connected to the pitch adjustment control and to the pitch actuator. Movement of the pitch adjustment control operates the pitch actuator via the pitch control cable. An X-direction control cable is operably connected to the X-direction control and to the X-direction actuator. Movement of the X-direction adjustment control operates the X-direction actuator via the X-direction control cable. A Y-direction control cable is operably connected to the Y-direction control and to the Y-direction actuator. Movement of the Y-direction adjustment control operates the Y-direction actuator via the Y-direction control cable.

In some embodiments, the roll adjustment control, pitch adjustment control, X-direction adjustment control, and Y-direction adjustment control are manually-operated thumbwheels, and rotation of each thumbwheel by a user causes corresponding axial rotation of a respective control cable and corresponding axial rotation of a respective actuator. In other embodiments, one or more of the roll adjustment control, pitch adjustment control, X-direction adjustment control, and Y-direction adjustment control are electric motor-assisted, rotatable controls.

In some embodiments, locking mechanisms are associated with the remote unit position controls, and are configured to prevent user operation of the controls when in a locked position.

In some embodiments, each control cable has a geometrically shaped rigid end that is configured to removably engage a free end of a respective actuator. Each control cable rigid end may have a shape that is different from the other control cable rigid ends such that each control cable free end can only removably engage one of the respective actuator free ends. Each control cable includes a flexible elastomeric collar that is configured to surround a respective actuator free end and to maintain engagement of a cable end to a respective actuator free end. Each flexible collar can be rolled or folded back then released to cover and conformably compress against an actuator free end to hold the end of the cable in position; then the collar can be pushed back to easily release the cable from an actuator free end.

According to some embodiments, a safety lanyard may be used to connect the remote control module to a rigid object, such as a patient support frame or head coil (or even the gantry or gantry housing) to prevent over extension of the cables or unwanted adjustments to the trajectory.

According to some embodiments, a drape is provided that is configured to be positioned near the body of a patient within a magnet of an MRI scanner. The drape includes a pocket that is configured to removably receive the remote control unit therein. The drape also includes one or more apertures through which the cables extend from the remote control unit to the frame.

According to some embodiments of the present invention, an imaging device is removably secured to the frame via a bracket. The bracket includes a sleeve that is configured to slidably receive the imaging device therein.

An elongated tubular member extends through the platform and yoke and is secured to the X-Y table of the frame. The targeting cannula is slidably secured within the tubular member and is movable between extended and retracted positions. The targeting cannula is configured to translate in response to translational movement of the X-Y support table and to rotate in response to rotational movement of the yoke and platform to define different axial trajectories extending through the patient access aperture of the base. The tubular member is configured to lock the targeting cannula in an extended position and in a retracted position.

A depth stop is removably secured within a proximal end of the tubular member. The depth stop receives a sheath therein, and is configured to limit the distance that the sheath can extend into the body of a patient. The sheath is configured to receive an elongated interventional device (e.g., imaging probe, stimulation lead, ablation device, injection device, etc.). In some embodiments, the sheath is removable. A locking mechanism is removably secured to the depth stop and is configured to prevent axial movement of an elongated interventional device extending through the sheath.

According to some embodiments of the present invention, an MRI-guided interventional system includes a frame with a cooperating targeting cannula that has a guide bore therethrough that is configured to guide placement of an interventional device in vivo. The frame is configured to rotate such that the targeting cannula can be positioned to a desired intrabody trajectory. The frame includes a base having a patient access aperture formed therein, wherein the base is configured to be secured to the body of a patient, a yoke movably mounted to the base and rotatable about a roll axis; and a platform movably mounted to the yoke and rotatable about a pitch axis. A plurality of user-activatable actuators are operably connected to the frame and are configured to rotate the frame relative to the body of the patient so as to position the targeting cannula to a desired intrabody trajectory. In some embodiments, the actuators are color-coded such that each actuator has a respective different color. In some embodiments, the frame includes a roll actuator operably connected to the yoke and configured to rotate the yoke about the roll axis; and a pitch actuator operably connected to the platform and configured to rotate the platform about the pitch axis.

In some embodiments, the system includes a remote control unit comprising a plurality of elongate control devices. Each control device includes first and second elongate rods axially connected at respective first ends via a first cable. The first rod second end is operably connected to a respective actuator via a second cable. Rotational movement of the second end of the second rod operates the actuator via the second cable. Each second cable may have a geometrically shaped rigid end configured to removably engage a free end of a respective actuator.

MRI-guided interventional methods, according to embodiments of the present invention, include affixing a frame with a cooperating targeting cannula to the body of a patient, wherein the frame is configured to translate and rotate such that the targeting cannula can be positioned to a desired intrabody access path trajectory. The targeting cannula includes a guide bore therethrough that is configured to guide placement of an interventional device in vivo. The targeting cannula position is adjusted (e.g., rotated about a roll axis, rotated about a pitch axis, and/or translated in X-Y directions) so that the targeting cannula is aligned with the desired access path trajectory while the patient is positioned within a magnetic field associated with an MRI scanner. Once the targeting cannula is repositioned, an interventional device is inserted through the targeting cannula guide bore and into the body of the patient for therapeutic and/or diagnostic purposes. The targeting cannula is movable between retracted and extended positions, and is moved to the extended position and locked in the extended position prior to the adjusting the access path trajectory thereof.

The necessary rotational and translational adjustments required to reposition the targeting cannula to the desired access path trajectory are displayed to a user via a graphical user interface. Both the actual access path trajectory and desired access path trajectory can be displayed, as well. In addition, the user can view the actual trajectory changing as he/she adjusts the position of the targeting cannula. In some embodiments, an indication of when the actual trajectory is aligned with a desired trajectory can be displayed to the user.

According to some embodiments of the present invention, an MRI-guided interventional system includes a head support apparatus for engaging and securing the head of a patient, and a targeting frame configured to be secured to the body of a patient. The targeting frame includes a cooperating targeting cannula that is configured to guide placement of an interventional device through a burr hole in a patient's skull in vivo. The system includes an MRI-compatible camera (e.g., digital camera capable of acquiring still images, streaming images, etc.) positioned proximate to the head support apparatus, and an MRI-compatible imaging device having one end attached to the targeting frame to provide a local field of view of the burr hole, and an opposite end in communication with the camera. In some embodiments, the imaging device is removably secured to the targeting frame via a bracket, which can include a sleeve configured to slidably receive the imaging device therein. The system also includes a display output module coupled to the camera for receiving electrical signals therefrom and for displaying images corresponding thereto.

According to other embodiments of the present invention, an MRI-guided interventional system includes a head support assembly for immobilizing the head of a patient during an MRI-guided procedure, a targeting frame configured to be secured to the skull of a patient, an MRI-compatible camera, and an MRI-compatible imaging device in communication with the camera. The head support assembly includes a base configured to be removably secured to a gantry, a head support frame attached to the base, and a longitudinally extending head coil apparatus positioned proximate to the head support frame and configured to surround at least a portion of a patient's head. The head coil apparatus includes a plurality of spaced-apart RF coils. The head support frame includes a pair of elongated arms extending outwardly in adjacent, spaced-apart relationship. A pair of head engagement rods are adjustably associated with the head support frame arms, and are configured to engage a patient's head within the head support frame.

The targeting frame includes a cooperating targeting cannula that is configured to guide placement of an interventional device through a burr hole in a patient's skull in vivo. The MRI-compatible camera is positioned proximate to the head support assembly. The MRI-compatible imaging device has one end attached to the targeting frame to provide a local field of view of the burr hole, and an opposite end in communication with the camera. In some embodiments, the imaging device is removably secured to the targeting frame via a bracket, which can include a sleeve configured to slidably receive the imaging device therein. The system also includes a display output module coupled to the camera for receiving electrical signals therefrom and for displaying images corresponding thereto.

In some embodiments, the head coil apparatus has an open-face, substantially U-shaped configuration with spaced-apart leg portions having free ends, wherein the head coil apparatus is positioned between the head support frame arms such that the leg portion free ends extend upwardly. In some embodiments, the head coil apparatus has an open-face, substantially U-shaped configuration and comprises a plurality of spaced-apart access windows formed therein. The head coil apparatus can be adjustable along a longitudinal direction relative to the head support frame.

According to other embodiments of the present invention, an MRI-guided interventional system includes a head support apparatus for engaging and securing the head of a patient, and a pair of targeting frames configured to be secured to the body of a patient in adjacent, spaced-apart relationship. Each targeting frame includes a cooperating targeting cannula that is configured to guide placement of an interventional device through a burr hole in a patients skull in vivo. A pair of MRI-compatible cameras are positioned proximate to the head support apparatus, and are in communication with a pair of MRI-compatible imaging devices. Each imaging device has one end attached to a respective targeting frame to provide a local field of view of a respective burr hole, and an opposite end in communication with a respective camera. The system also includes a display output module coupled to the camera for receiving electrical signals therefrom and for displaying images corresponding thereto.

BRIEF DESCRIPTION OF THE DRAWINGS

FIGS. 32A-32C illustrate a remote control unit for remotely controlling the positioning actuators of the frame of FIG. 3A, according to other embodiments of the present invention.

DETAILED DESCRIPTION

Figure 1A:
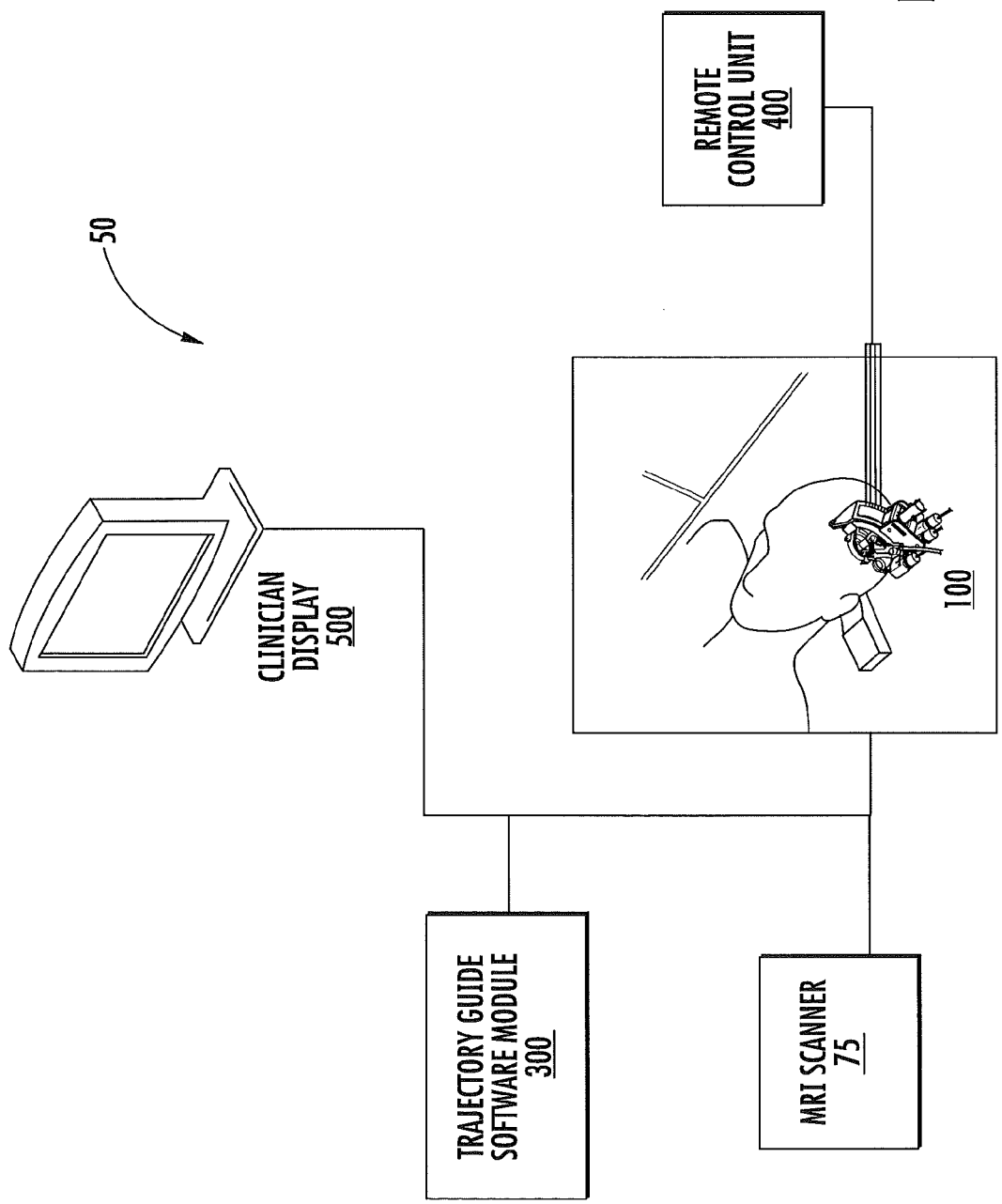
FIG. 1A is a block diagram of an MRI-guided interventional system, according to some embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MRI environment and/or can operate as intended in an MRI environment, and, as such, if residing within the high-field strength region of the magnetic field, is typically made of a non-ferromagnetic MRI compatible material(s) suitable to reside and/or operate in a high magnetic field environment.

The term "high-magnetic field" refers to field strengths above about 0.5 T, typically above 1.0 T, and more typically between about 1.5 T and 10 T.

The term "targeting cannula" refers to an elongate device, typically having a substantially tubular body that can be oriented to provide positional data relevant to a target treatment site and/or define a desired access path orientation or trajectory. At least portions of a targeting cannula contemplated by embodiments of the invention can be configured to be visible in an MRI image, thereby allowing a clinician to visualize the location and orientation of the targeting cannula in vivo relative to fiducial and/or internal tissue landscape features. Thus, the term "cannula" refers to an elongate device that can be associated with a trajectory frame that attaches to a patient, but does not necessarily enter the body of a patient.

The term "imaging coils" refers to a device that is configured to operate as an MRI receive antenna. The term "coil" with respect to imaging coils is not limited to a coil shape but is used generically to refer to MRI antenna configurations, loopless, looped, etc., as are known to those of skill in the art. The term "fluid-filled" means that the component includes an amount of the fluid but does not require that the fluid totally, or even substantially, fill the component or a space associated with the component. The fluid may be an aqueous solution, MR contrast agent, or any material that generates MRI signal.

The term "two degrees of freedom" means that the trajectory frame described herein allows for at least translational (swivel or tilt) and rotational movement over a fixed site, which may be referred to as a Remote Center of Motion (RCM).

Embodiments of the present invention can be configured to guide and/or place diagnostic or interventional devices and/or therapies to any desired internal region of the body or object using MRI and/or in an MRI scanner or MRI interventional suite. The object can be any object, and may be particularly suitable for animal and/or human subjects. Some embodiments can be sized and configured to place implantable DBS leads for brain stimulation, typically deep brain stimulation. Some embodiments can be configured to deliver tools or therapies that stimulate a desired region of the sympathetic nerve chain. Other uses inside or outside the brain include stem cell placement, gene therapy or drug delivery for treating physiological conditions. Some embodiments can be used to treat tumors. Some embodiments can be used for RF ablation, laser ablation, cryogenic ablation, etc. In some embodiments the trajectory frame and/or interventional tools can be configured to facilitate high resolution imaging via integral intrabody imaging coils (receive antennas), and/or the interventional tools can be configured to stimulate local tissue, which can facilitate confirmation of proper location by generating a physiologic feedback (observed physical reaction or via fMRI).

Some embodiments can be used to deliver bions, stem cells or other target cells to site-specific regions in the body, such as neurological target and the like. In some embodiments, the systems deliver stem cells and/or other cardio-rebuilding cells or products into cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318, 6,405,079; 6,167,311; 6539,263; 6,609,030 and 6,050,992, the contents of which are hereby incorporated by reference as if recited in full herein.

Generally stated, some embodiments of the invention are directed to MRI interventional procedures and provide interventional tools and/or therapies that may be used to locally place interventional tools or therapies in vivo to site-specific regions using an MRI system. The interventional tools can be used to define an MRI-guided trajectory or access path to an in vivo treatment site. Some embodiments of the invention provide interventional tools that can provide positional data regarding location and orientation of a tool in 3-D space with a visual confirmation on an MRI. Embodiments of the invention may provide an integrated system that may allow physicians to place interventional devices/leads and/or therapies accurately and in shorter duration procedures over conventional systems (typically under six hours for DBS implantation procedures, such as between about 1-5 hours).

In some embodiments, MRI can be used to visualize (and/or locate) a therapeutic region of interest inside the brain or other body locations and utilize MRI to visualize (and/or locate) an interventional tool or tools that will be used to deliver therapy and/or to place a chronically implanted device that will deliver therapy. Then, using the three-dimensional data produced by the MRI system regarding the location of the therapeutic region of interest and the location of the interventional tool, the system and/or physician can make positional adjustments to the interventional tool so as to align the trajectory of the interventional tool, so that when inserted into the body, the interventional tool will intersect with the therapeutic region of interest. With the interventional tool now aligned with the therapeutic region of interest, an interventional probe can be advanced, such as through an open lumen inside of the interventional tool, so that the interventional probe follows the trajectory of the interventional tool and proceeds to the therapeutic region of interest. It should be noted that the interventional tool and the interventional probe may be part of the same component or structure. A sheath may optionally form the interventional tool or be used with an interventional probe or tool.

In particular embodiments, using the MRI in combination with local or internal imaging coils and/or MRI contrast material that may be contained at least partially in and/or on the interventional probe or sheath, the location of the interventional probe within the therapeutic region of interest can be visualized on a display or image and allow the physician to either confirm that the probe is properly placed for delivery of the therapy (and/or placement of the implantable device that will deliver the therapy) or determine that the probe is in the incorrect or a non-optimal location. Assuming that the interventional probe is in the proper desired location, the therapy can be delivered and/or the interventional probe can be removed and replaced with a permanently implanted therapeutic device at the same location.

In some embodiments, in the event that the physician determines from the MRI image produced by the MRI and the imaging coils, which may optionally be contained in or on the interventional probe, that the interventional probe is not in the proper location, a new therapeutic target region can be determined from the MRI images, and the system can be updated to note the coordinates of the new target region. The interventional probe is typically removed (e.g., from the brain) and the interventional tool can be repositioned so that it is aligned with the new target area. The interventional probe can be reinserted on a trajectory to intersect with the new target region. Although described and illustrated herein with respect to the brain and the insertion of deep brain stimulation leads, it is understood that embodiments of the present invention may be utilized at other portions of the body and for various other types of procedures.

Exemplary embodiments are described below with reference to block diagrams and/or flowchart illustrations of methods, apparatus (systems and/or devices) and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, exemplary embodiments may be implemented in hardware and/or in software (including firmware, resident software, micro-code, etc.). Furthermore, exemplary embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a programmed digital signal processor or microcontroller.

Embodiments of the present invention will now be described in detail below with reference to the figures. FIG. 1A is a block diagram of an MRI-guided interventional system 50, according to some embodiments of the present invention. The illustrated system 50 includes an MRI scanner 75, a trajectory frame 100 attached to the body of a patient positioned within a magnetic field of the MRI scanner 75, a remote control unit 400, a trajectory guide software module 300, and a clinician display 500. The trajectory frame 100 supports a targeting cannula through which various interventional devices may be inserted into the body of a patient. The frame 100 is adjustable such that the targeting cannula is rotatable about a pitch axis, about a roll axis, and such that the targeting cannula can translate in X-Y directions. The frame 100 may be attached to the body of a patient directly or indirectly and may be configured to be attached to various parts of the body.

Figure 1B:
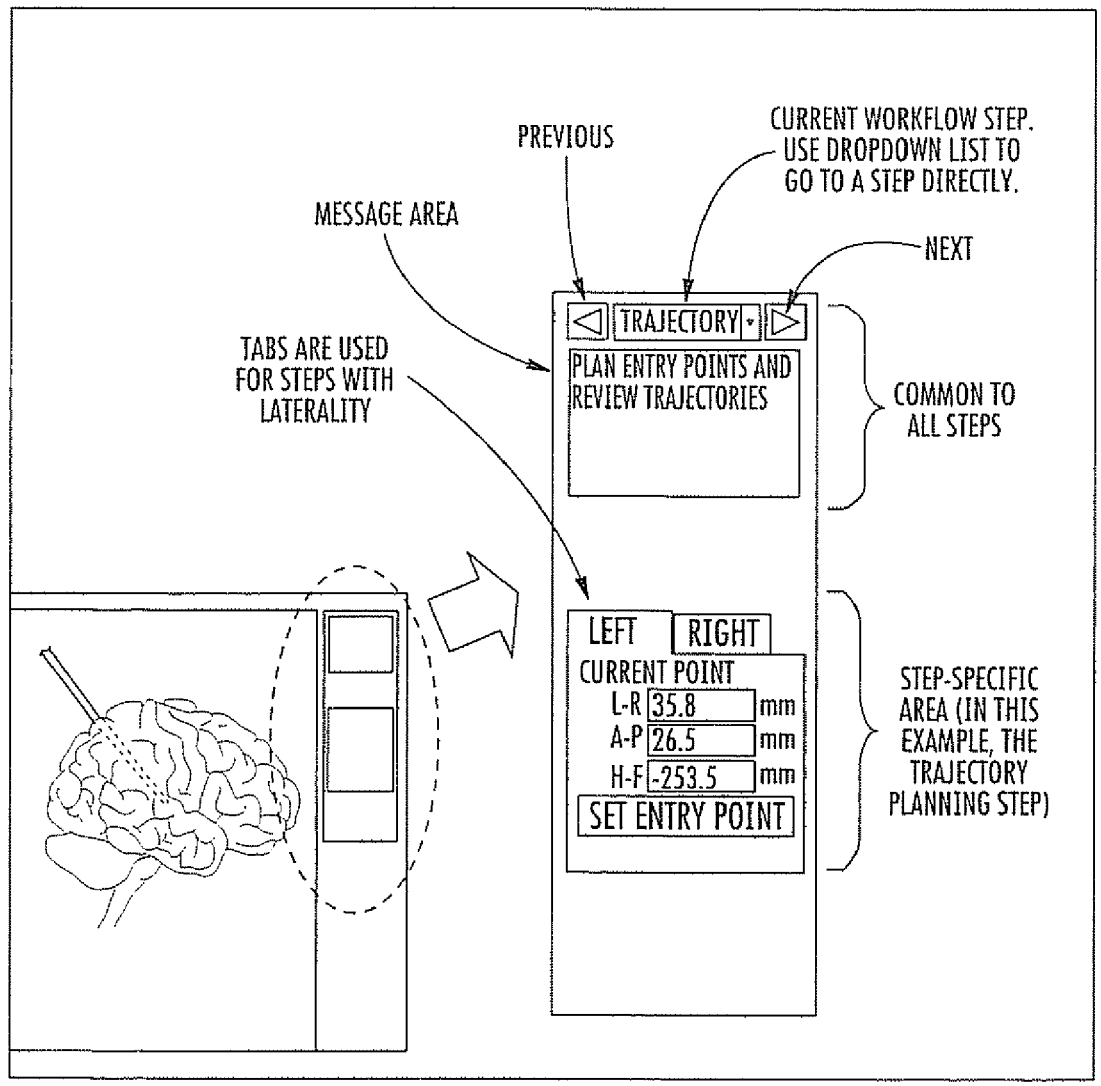
FIG. 1B illustrates a user interface that displays, and that allows a user to adjust, the trajectory of a targeting cannula, according to some embodiments of the present invention.
Figure 17:
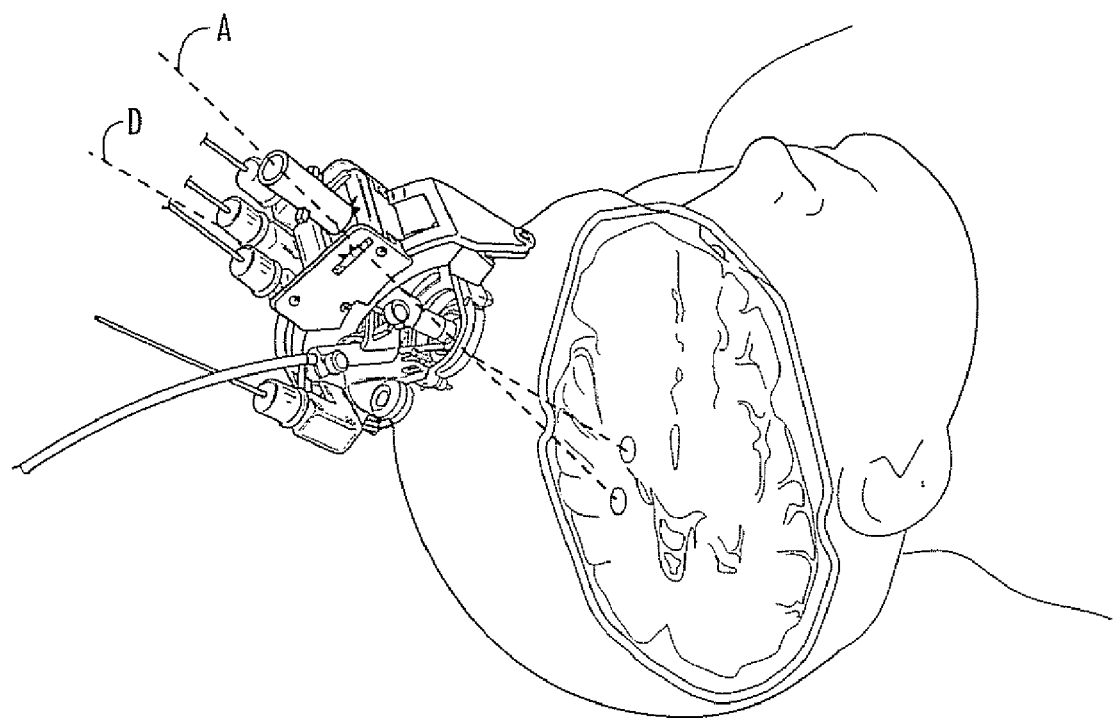
FIG. 17 illustrates the frame of FIG. 3A secured to the skull of a patient and illustrates a desired trajectory for an interventional device, and also illustrates the actual trajectory of the interventional device as oriented by the frame.
Figure 18:
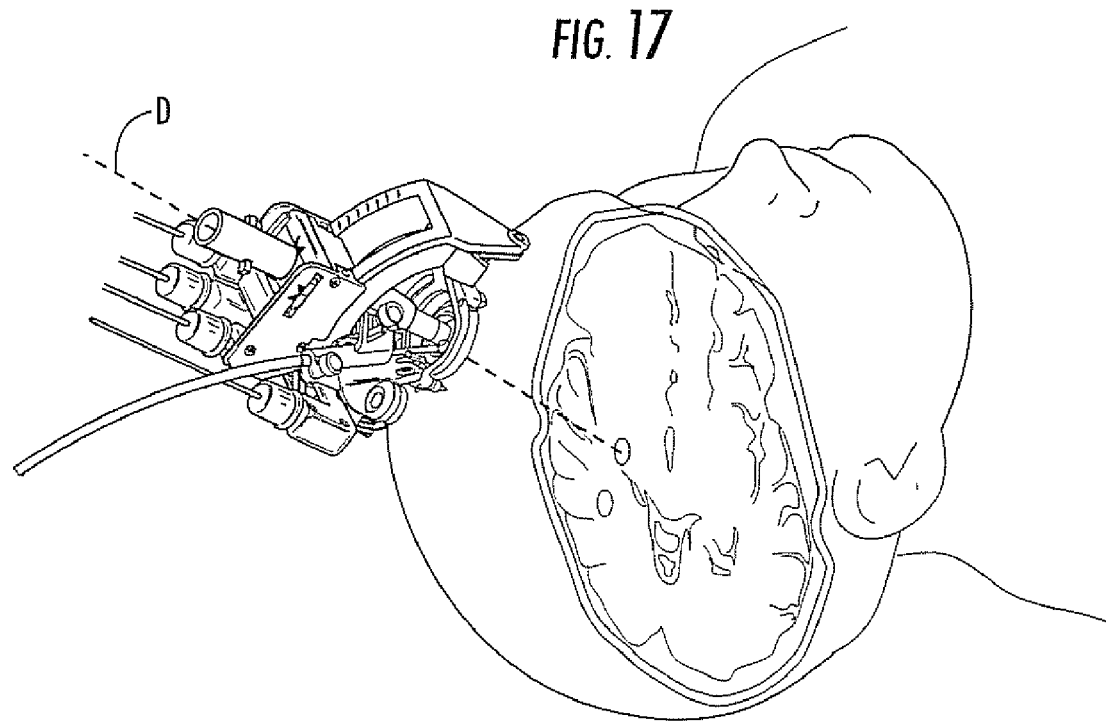
FIG. 18 illustrates the frame of FIG. 17 after reorientation via manipulation of one or more frame actuators such that the actual trajectory is adjusted to be in alignment with the desired trajectory.

In some embodiments, a remote control unit 400 is provided to allow a user to remotely adjust the position of the targeting cannula. The trajectory guide software module 300 allows a user to define and visualize, via display 500, a desired trajectory (D, FIGS. 17-18) into the body of a patient of an interventional device extending through the targeting cannula. The trajectory guide software module 300 also allows the user to visualize and display, via display 500, an actual trajectory (A, FIG. 17) into the body of an interventional device extending through the targeting cannula. The trajectory guide software module 300 displays to the user the necessary positional adjustments (e.g., pitch axis rotation, roll axis rotation, X-Y translation) needed to align the actual trajectory of the targeting cannula with the desired trajectory path (FIG. 1B). In addition, the user can view, via display 500, the actual trajectory changing as he/she adjusts the position of the targeting cannula. The trajectory guide software module 300 is configured to indicate and display when an actual trajectory is aligned with a desired trajectory.

Figure 2A:
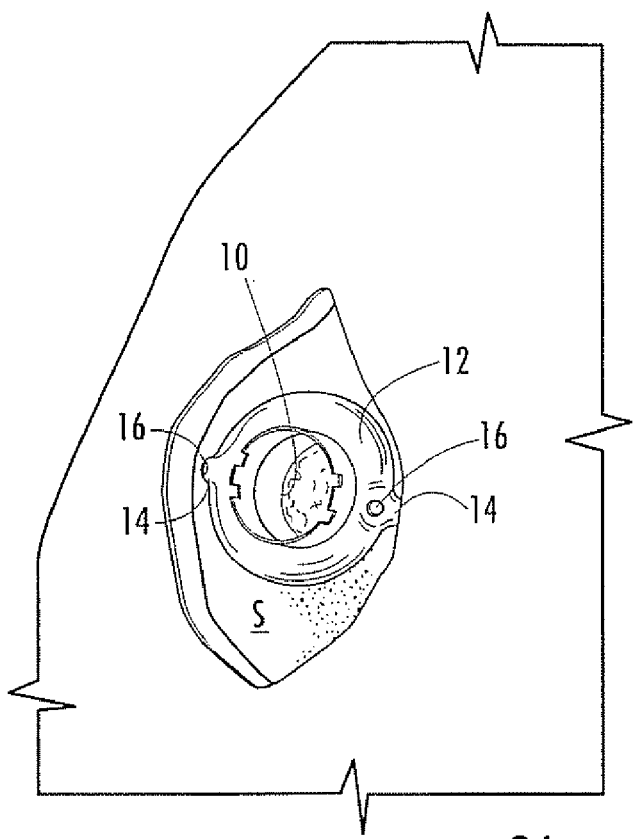
FIG. 2A is a top perspective view of a burr hole formed in the skull of a patient, and a burr hole ring overlying the burr hole and secured to the skull.
Figure 2B:
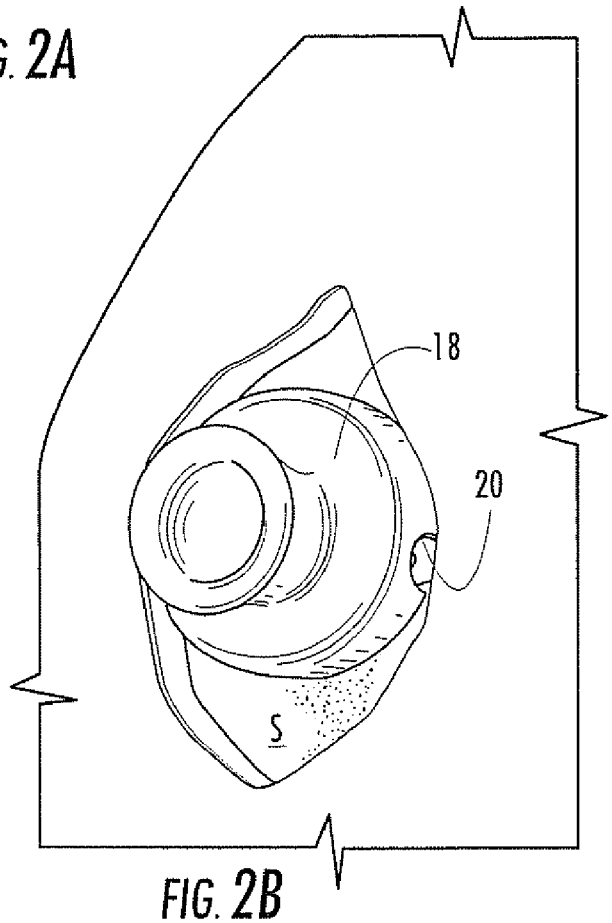
FIG. 2B is a top perspective view of a removable centering device positioned on the burr hole ring of FIG. 1.

FIG. 2A illustrates a burr hole 10 formed in the skull S of a patient. A burr hole ring 12 overlies the burr hole 10 and is secured to the skull S. The illustrated burr hole ring 12 has a pair of ears 14, each configured to receive a respective fastener (e.g., screw) therethrough for securing the burr hole ring 12 to the skull. In the illustrated embodiment, the burr hole ring 12 is secured to the skull S via screws 16. FIG. 2B illustrates a removable centering device 18 positioned on the burr hole ring 12. The centering device 18 includes cut out portions 20 that fit over the ears 14 of the burr hole ring 12. The function of the centering device 18 is to facilitate centering a trajectory frame 100, described below, over the burr hole 10. After the frame 100 is attached to the skull of a patient, the centering device 18 is removed.

Figure 3A:
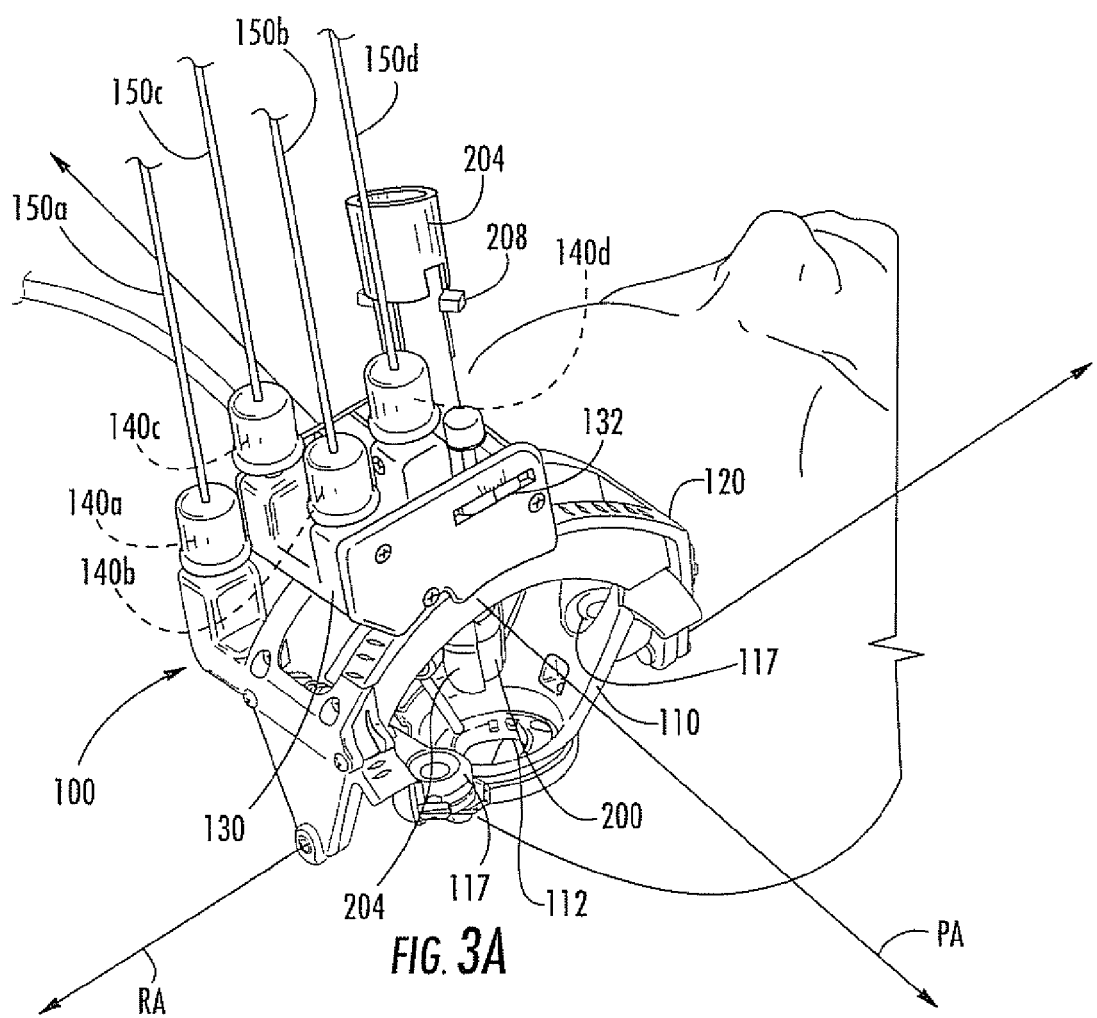
FIG. 3A is a perspective view of a trajectory frame utilized in the MRI-guided interventional system, according to some embodiments of the present invention.

Referring to FIG. 3A, a trajectory frame 100 with a targeting cannula 200 associated therewith is illustrated. The trajectory frame 100 allows for the adjustability (typically at least two degrees of freedom, including rotational and translational) and calibration/fixation of the trajectory of the targeting cannula 200 and/or probe or tool inserted through the targeting cannula 200. The targeting cannula 200 includes an axially-extending guide bore (not shown) therethrough that is configured to guide the desired therapeutic or diagnostic tool, e.g., intra-brain placement of a stimulation lead (or other type of device) in vivo, as will be described below. Intra-brain placement of devices may include chronically placed devices and acutely placed devices. The trajectory frame 100 may include fiducial markers 117 that can be detected in an MRI to facilitate registration of position in an image.

The illustrated trajectory frame 100 is configured to be mounted to a patient's skull around a burr hole ring (12, FIG. 1) and over a burr hole (10, FIG. 1), to provide a stable platform for advancing surgical devices, leads, etc. in the brain. The frame 100 includes a base 110, a yoke, 120, a platform 130, and a plurality of actuators 140a-140d. The base 110 has a patient access aperture 112 formed therein, as illustrated. The base 110 is configured to be secured (directly or indirectly) to the skull of a patient such that the patient access aperture 112 overlies the burr hole 10 in the patient skull. The patient access aperture 112 is centered over the burr hole 10 via the removable centering device 18. The yoke 120 is movably mounted to the base 110 and is rotatable about a roll axis RA. A roll actuator 140a is operably connected to the yoke 120 and is configured to rotate the yoke 120 about the roll axis RA, as will be described in detail below. In some embodiments, the yoke 120 has a range of motion about the roll axis RA of about seventy degrees (70°). However, other ranges, greater and lesser than 70°, are possible, e.g., any suitable angle typically between about 10°-90°, 30°-90°, etc. The illustrated platform 130 is movably mounted to the yoke 120 and is rotatable about a pitch axis PA. In some embodiments, the platform 130 has a range of motion about the pitch axis PA of about seventy degrees (70°). However, other ranges, greater and lesser than 70°, are possible, e.g., any suitable angle typically between about 10°-90°, 30°-90°, etc.

Figure 3B:
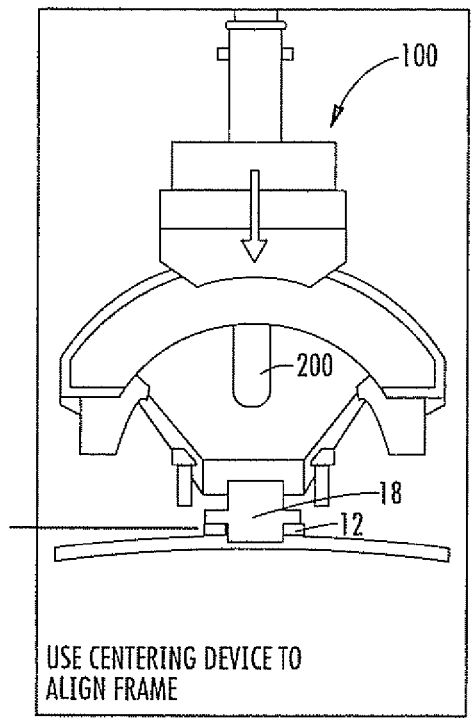
FIGS. 3B-3E are side view, schematic illustrations of the trajectory frame.
Figure 3C:
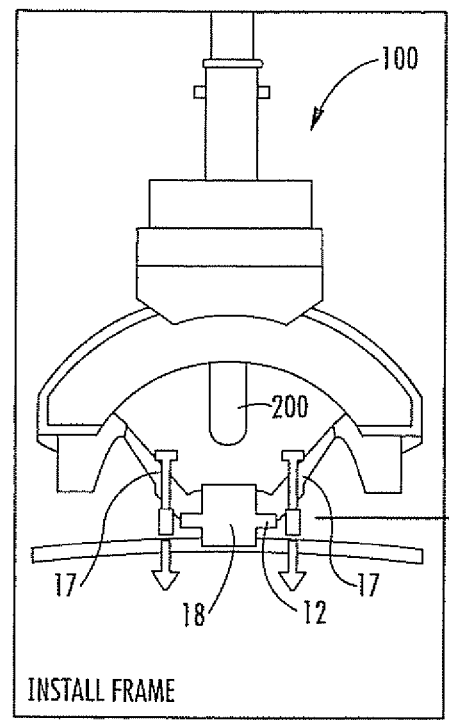
Figure 3D:
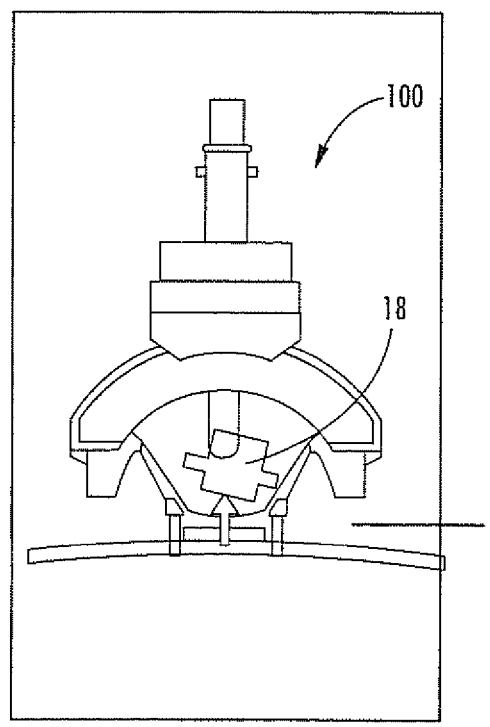
Figure 3E:
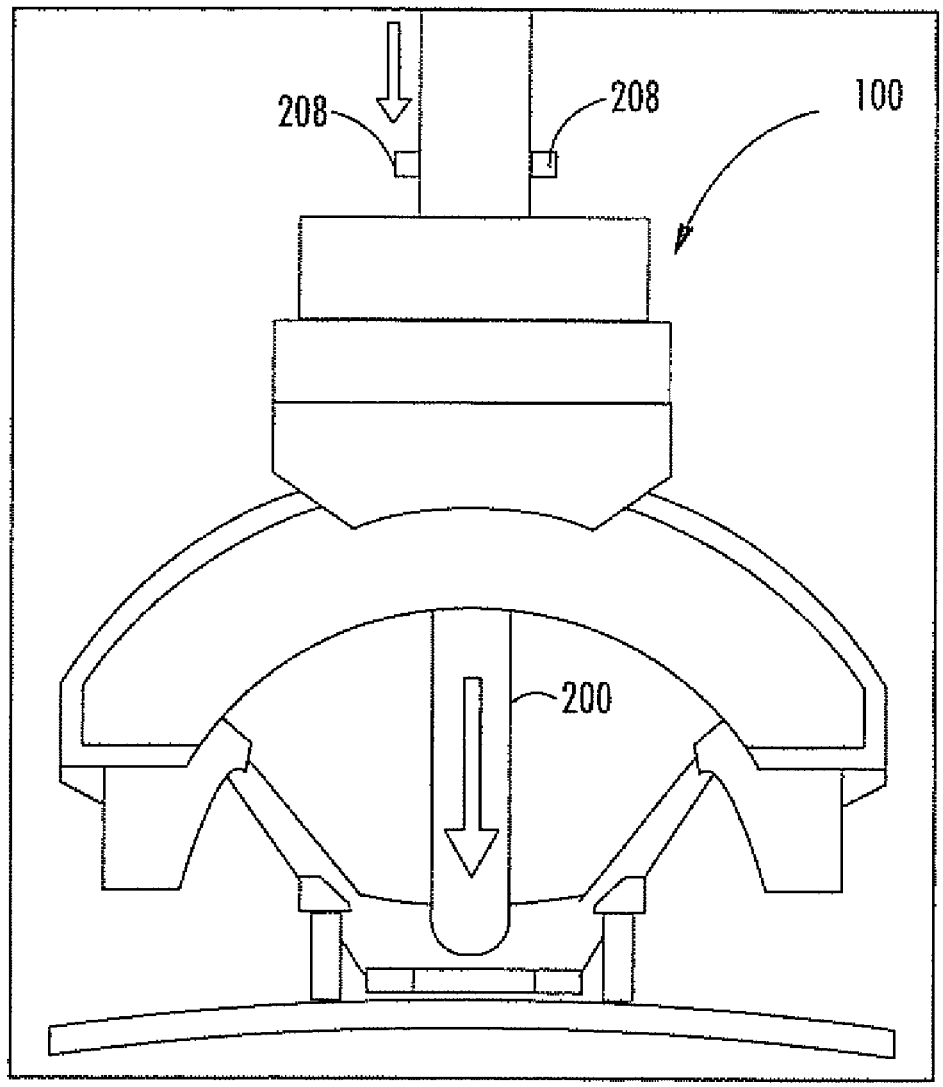

FIGS. 3B-3E are side view, schematic illustrations of the trajectory frame being secured to the skull of a patient. FIG. 3B illustrates use of the centering device 18 to align the frame 100 relative to the burr hole 10. In FIG. 3C, the frame 100 is secured to the skull with fasteners and such that the patient access aperture 112 in the base 110 is centered around the centering device 18. In FIG. 3D, the yoke 120 is rotated out of the way such that the centering device 18 can be removed. In FIG. 3E, the targeting cannula 200 is moved to an extended position and locked in the extended position via prongs 208.

The platform 130 includes an X-Y support table 132 that is movably mounted to the platform 130. The X-Y support table 132 is configured to move in an X-direction and Y-direction relative to the platform 130. An X-direction actuator 140c is operably connected to the platform 130 and is configured to move the X-Y support table 132 in the X-direction. A Y-direction actuator 140d is operably connected to the platform 130 and is configured to move the X-Y support table 132 in the Y-direction. A pitch actuator 140b is operably connected to the platform 130 and is configured to rotate the platform 130 about the pitch axis PA, as will be described in detail below.

The actuators 140a-140d are configured to translate and/or rotate the frame. The targeting cannula 200 is configured to translate in response to translational movement of the X-Y support table 132 and to rotate in response to rotational movement of the yoke 120 and platform 130 to define different axial intrabody trajectories extending through the patient access aperture 112 in the frame base 110.

Figure 9:
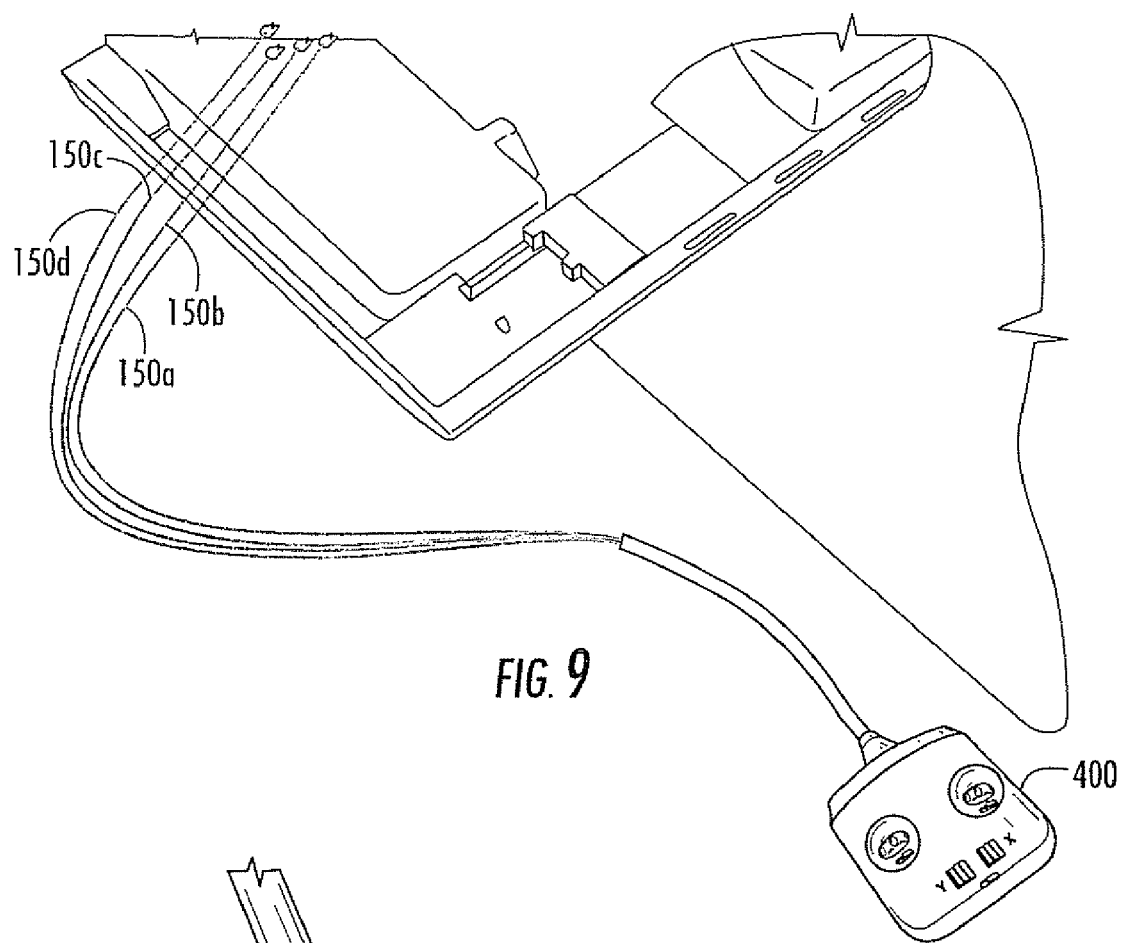
FIGS. 9 and 10A-10C illustrate a remote control unit for remotely controlling the positioning actuators of the frame of FIG. 3A, according to some embodiments of the present invention.
Figure 10A:
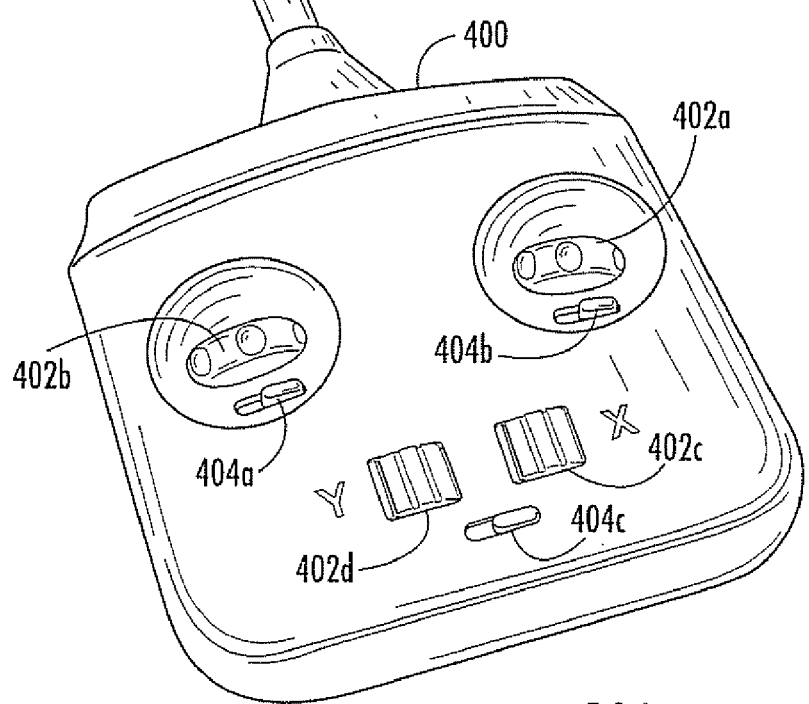

The actuators 140a-140d may be manually-operated devices, such as thumbscrews, in some embodiments. The thumbscrews can be mounted on the frame 100 or may reside remotely from the frame 100. A user may turn the actuators 140a-140d by hand to adjust the position of the frame 100 and, thereby, a trajectory of the targeting cannula 200. In other embodiments, the actuators 140a-140d are operably connected to a remote control unit 400 (FIGS. 9-10) via a respective plurality of non-ferromagnetic, flexible drive shafts or control cables 150a-150d. The remote control unit 400 includes a plurality of position controls 402a-402d, and each cable 150a-150d is operably connected to a respective position control 402a-402d and to a respective actuator 140a-140d. Movement of a position control 402a-402d operates a respective actuator 140a-140d via a respective control cable 150a-150d, as will be described below. The cables 150a-150d may extend a suitable distance (e.g., between about 1-4 feet, etc.) to allow a clinician to adjust the settings on the trajectory frame 100 without moving a patient and from a position outside the bore of a magnet (where such magnet type is used) associated with an MRI scanner.

Figure 6:
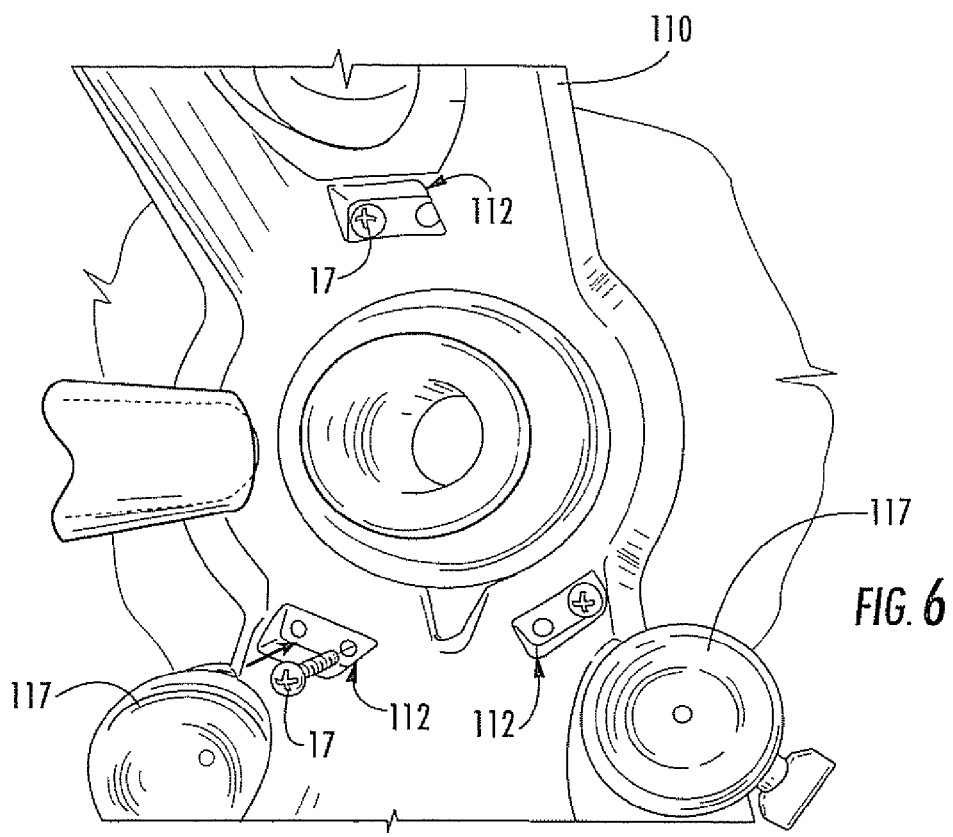
FIG. 6 illustrates the base secured to the skull of a patient.
Figure 7:
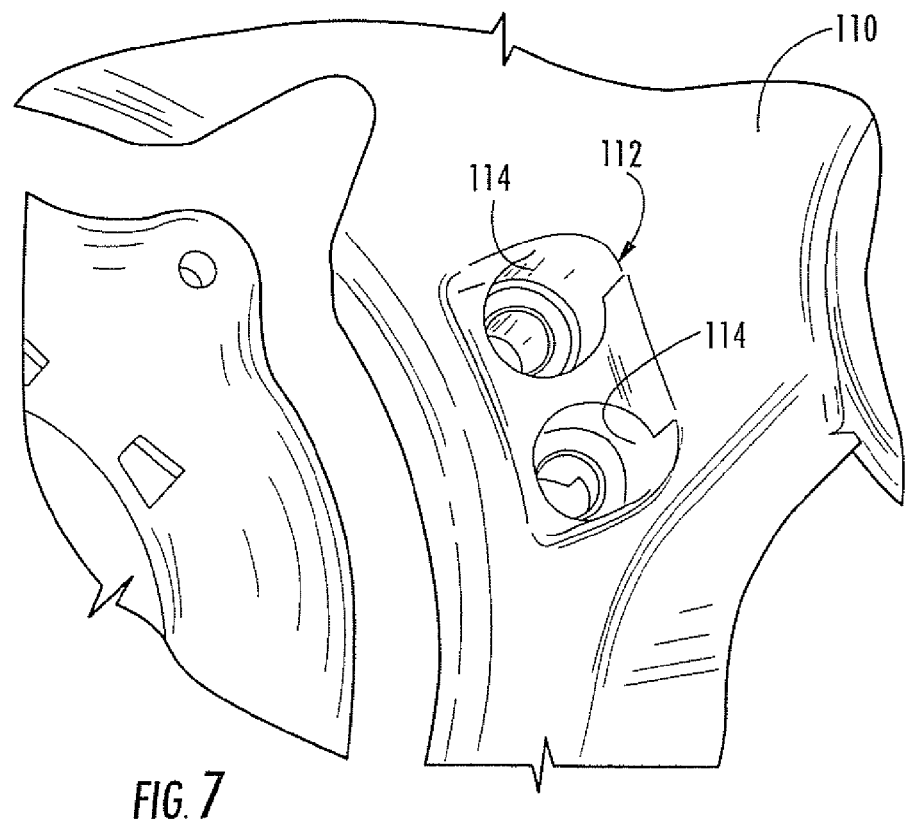
FIG. 7 is an enlarged partial perspective view of the base illustrating an attachment location with a pair of adjacent apertures for receiving fasteners therethrough, according to some embodiments of the present invention.

Referring to FIGS. 6-7, the base 110 includes a plurality of locations 112 for attaching the base 110 to a skull of a patient via fasteners. Each location may include two or more adjacent apertures 114. Each aperture 114 is configured to receive a fastener (e.g., a screw, rod, pin, etc.) therethrough that is configured to secure the base 110 to the skull of a patient.

The base 110 also includes MRI-visible fiducial markers 117 that allow the location/orientation of the frame 100 to be determined within an MRI image during an MRI-guided procedure. In the illustrated embodiment, the fiducial markers 117 have a torus or "doughnut" shape and are spaced apart. However, fiducial markers having various shapes and positioned at various locations on the frame 100 may be utilized.

Figure 4:
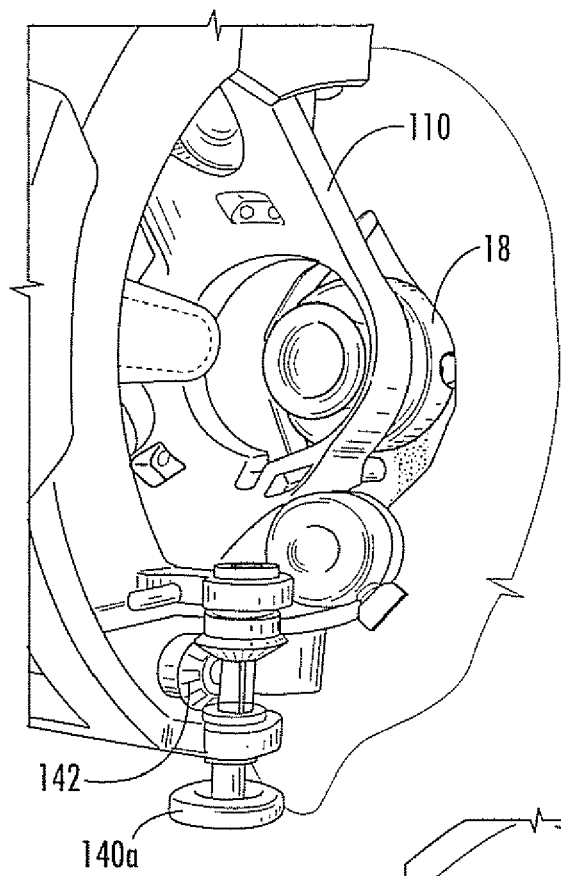
FIGS. 4-5 are partial perspective views of the frame of FIG. 3A illustrating the base of the frame being positioned on the skull of a patient with the centering device of FIG. 2B extending through the patient access aperture.
Figure 5:
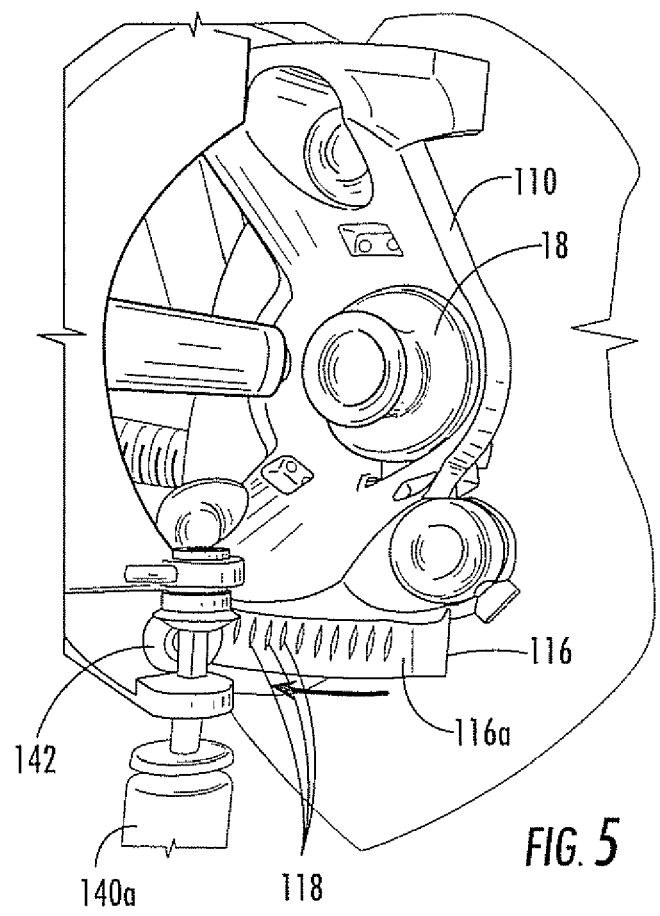
Figure 11:
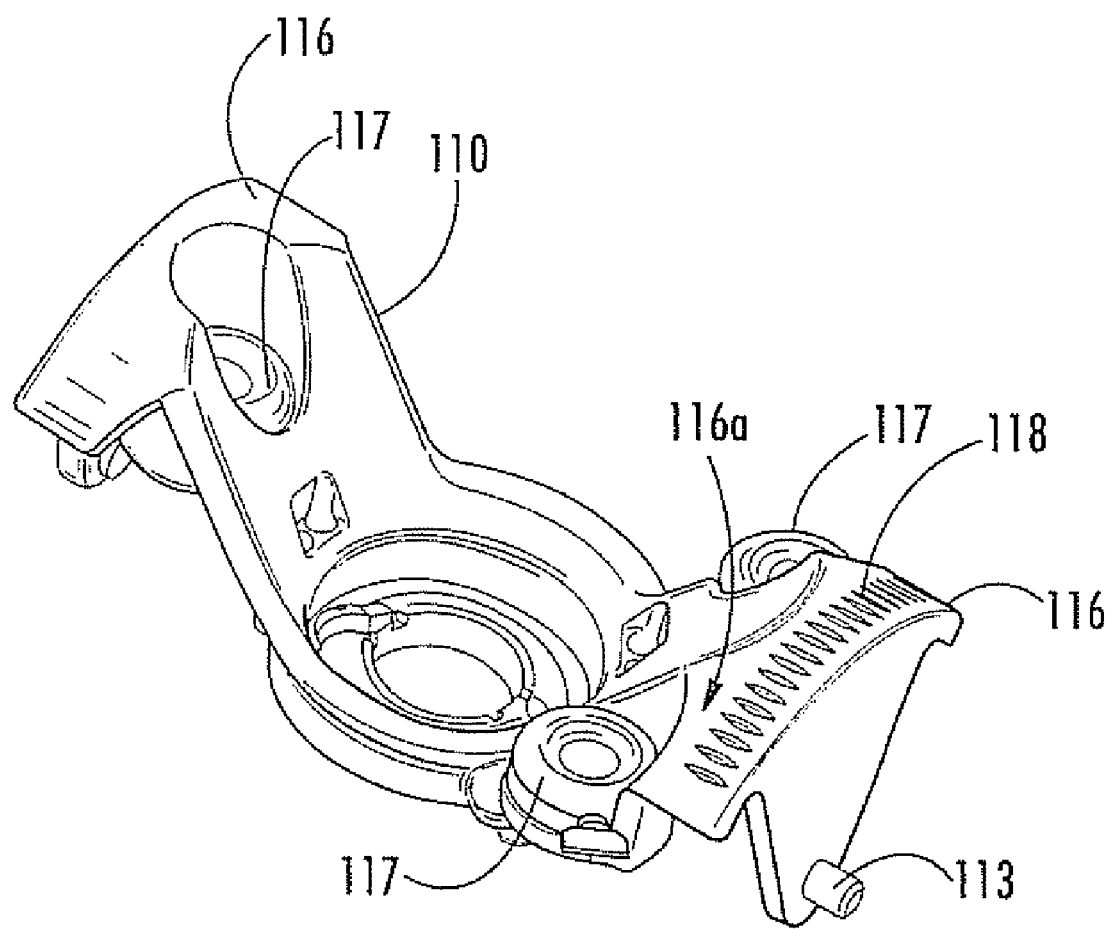
FIG. 11 is a perspective view of the base of the frame of FIG. 3A illustrating fiducial markers associated therewith and illustrating an arcuate arm with a thread pattern formed in a surface thereof that is configured to be engaged by a roll axis actuator, according to some embodiments of the present invention.

The base 110 also includes a pair of spaced apart arcuate arms 116, as illustrated in FIG. 11. The yoke 120 is pivotally attached to pivot points 113 for rotation about the roll axis RA. The yoke 120 engages and moves along the base arcuate arms 116 when rotated about the roll axis RA. In the illustrated embodiment, one of the base arcuate arms 116 includes a thread pattern 118 formed in (e.g., embossed within, machined within, etc.) a surface 116a thereof. However, in other embodiments, both arms 116 may include respective thread patterns. The roll actuator 140a includes a rotatable worm 142 with teeth that are configured to engage the thread pattern 118, as illustrated in FIG. 5. As the worm 142 is rotated, the teeth travel along the thread pattern 118 in the arcuate arm surface 116a. Because the base 110 is fixed to a patient's skull, rotation of the roll actuator worm 142 causes the yoke 120 to rotate about the roll axis RA relative to the fixed base 110. Rotation about roll axis RA is illustrated in FIGS. 4-5. For example, in FIG. 5, the yoke 120 is rotated about the roll axis RA sufficiently to allow removal of the centering device 18.

Figure 12:
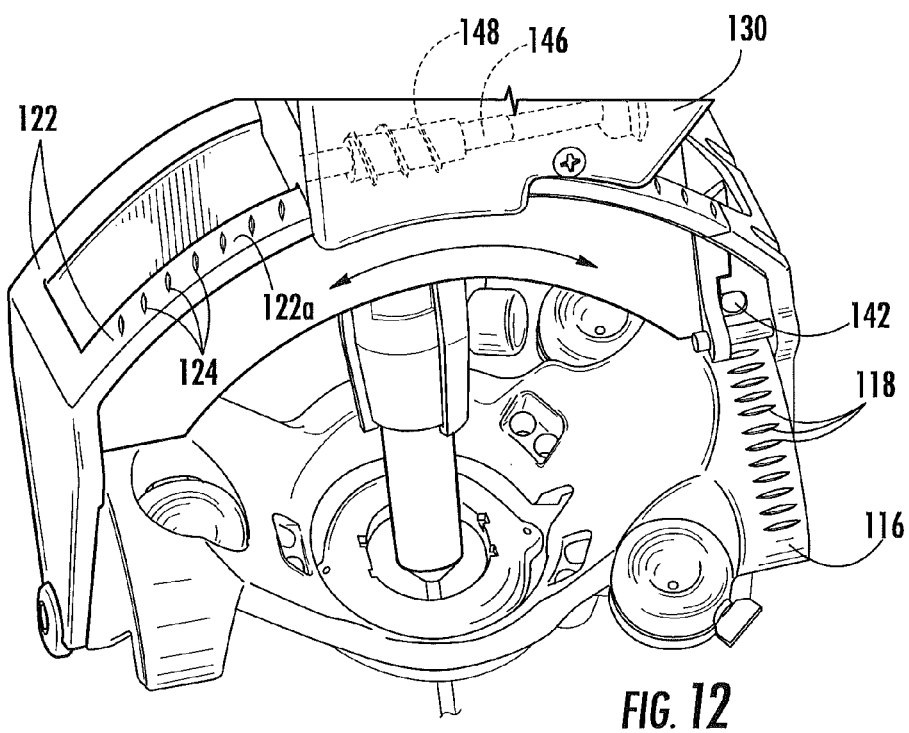
FIG. 12 is a partial perspective view of the frame of FIG. 3A illustrating a yoke arcuate arm with a thread pattern formed in a surface thereof that is configured to be engaged by a pitch axis actuator, according to some embodiments of the present invention.

Referring to FIG. 12, the yoke 120 includes a pair of spaced apart upwardly extending, arcuate arms 122. The platform 130 engages and moves along the yoke arcuate arms 122 when rotated about the pitch axis PA. In the illustrated embodiment, one of the yoke arcuate arms 122 includes a thread pattern 124 formed in (e.g., embossed within, machined within, etc.) a surface 122a thereof. However, in other embodiments, both arms 122 may include respective thread patterns. The pitch actuator 140b includes a rotatable worm 146 with teeth 148 that are configured to engage the thread pattern 124. As the worm 146 is rotated, the teeth 148 travel along the thread pattern 124 in the arcuate arm surface 122a. Because the base 110 is fixed to a patient's skull, rotation of the pitch actuator worm 146 causes the platform 130 to rotate about the pitch axis PA relative to the fixed base 110.

Figure 19A:
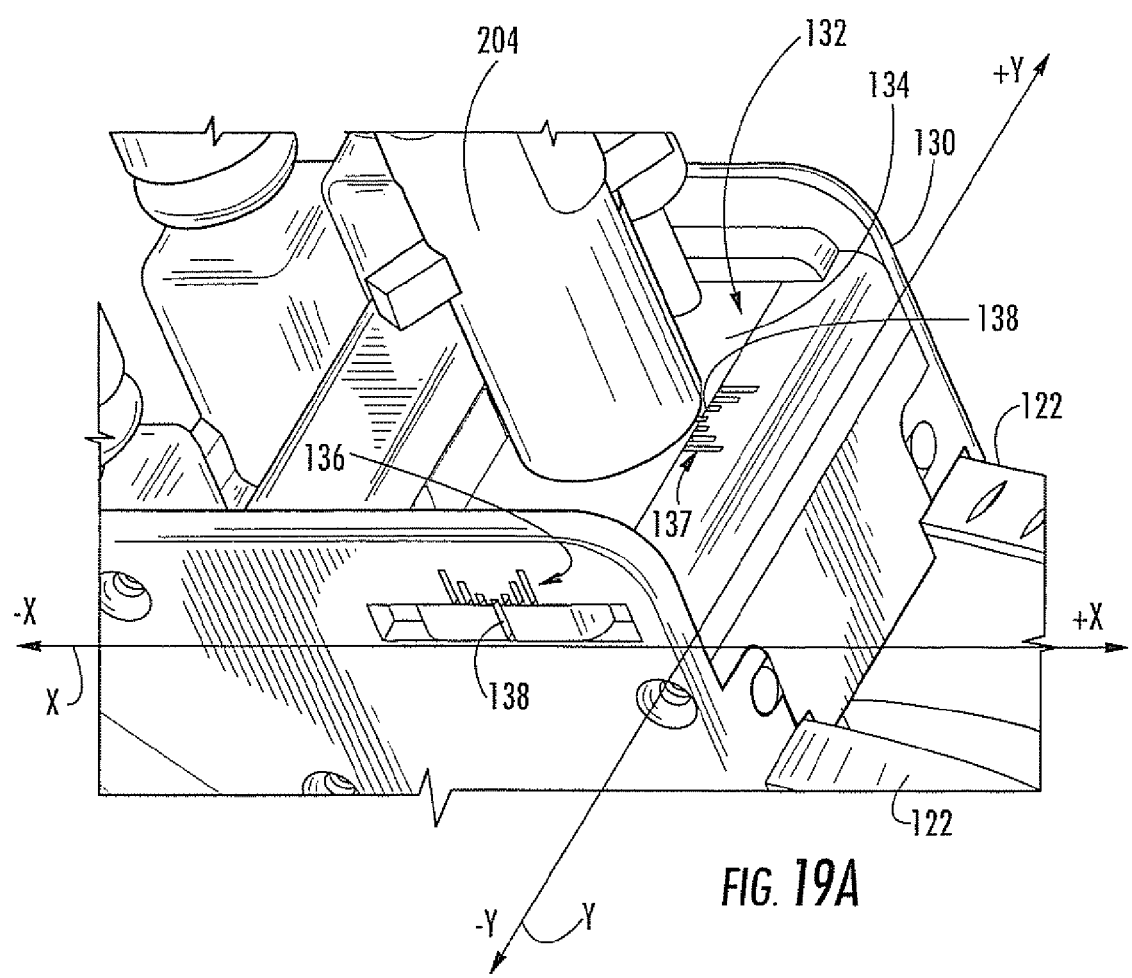
FIG. 19A is an enlarged, partial perspective view of the frame of FIG. 3A illustrating the X-Y support table, according to some embodiments of the present invention.
Figure 19B:
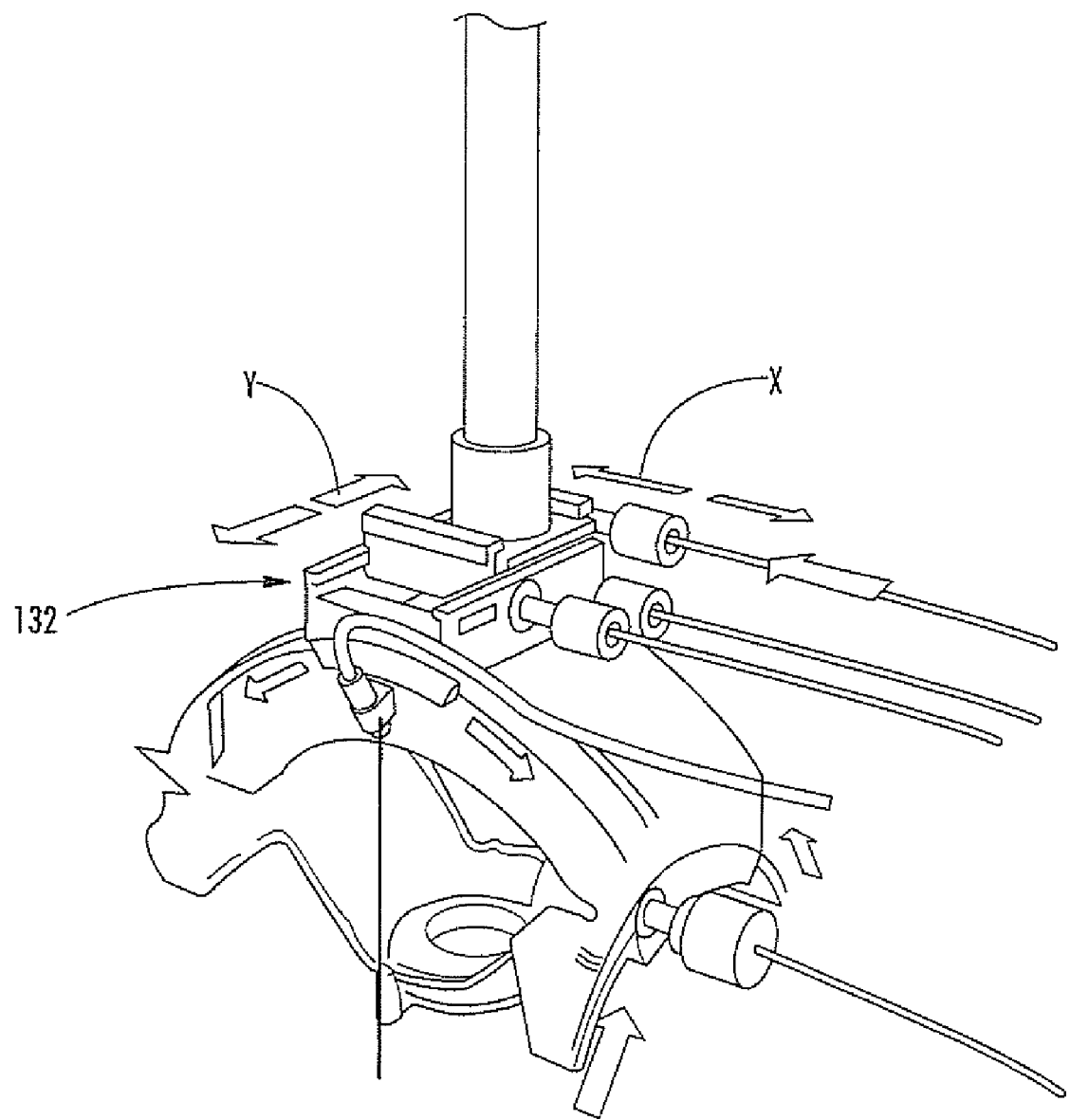
FIG. 19B schematically illustrates X-Y translation of an X-Y support table and rotational movement of the yoke and platform, according to some embodiments of the present invention.

As illustrated in FIG. 19A, the X-Y support table 132 includes a moving plate 134 that moves in both the X-direction and Y-direction. The X-direction actuator 140c, when rotated, causes translational movement of the moving plate 134 along the X-axis. For example, clockwise rotation of the X-direction actuator 140c causes movement toward the "−X direction (i.e., to the left) in FIG. 19A; and counterclockwise rotation of the X-direction actuator 140c causes movement along the +X direction (i.e., to the right) in FIG. 19A, etc. The Y-direction actuator 140d, when rotated, causes translational movement of the moving plate 134 along the Y-axis. For example, clockwise rotation of the Y-direction actuator 140d causes movement along the −Y direction (i.e., out of the paper) in FIG. 19A; and clockwise rotation of the Y-direction actuator 140d causes movement along the +Y direction (i.e., into the paper) in FIG. 19A. In the illustrated embodiment, graduation scales 136, 137 are provided on the platform adjacent the moving plate 134. The moving plate 134 includes a pair of marks or indicators 138 that provide visual indication of X-Y movement of the moving plate 134. FIG. 19B illustrates X-Y translation of an X-Y support table 132, according to some embodiments of the present invention.

Figure 19C:
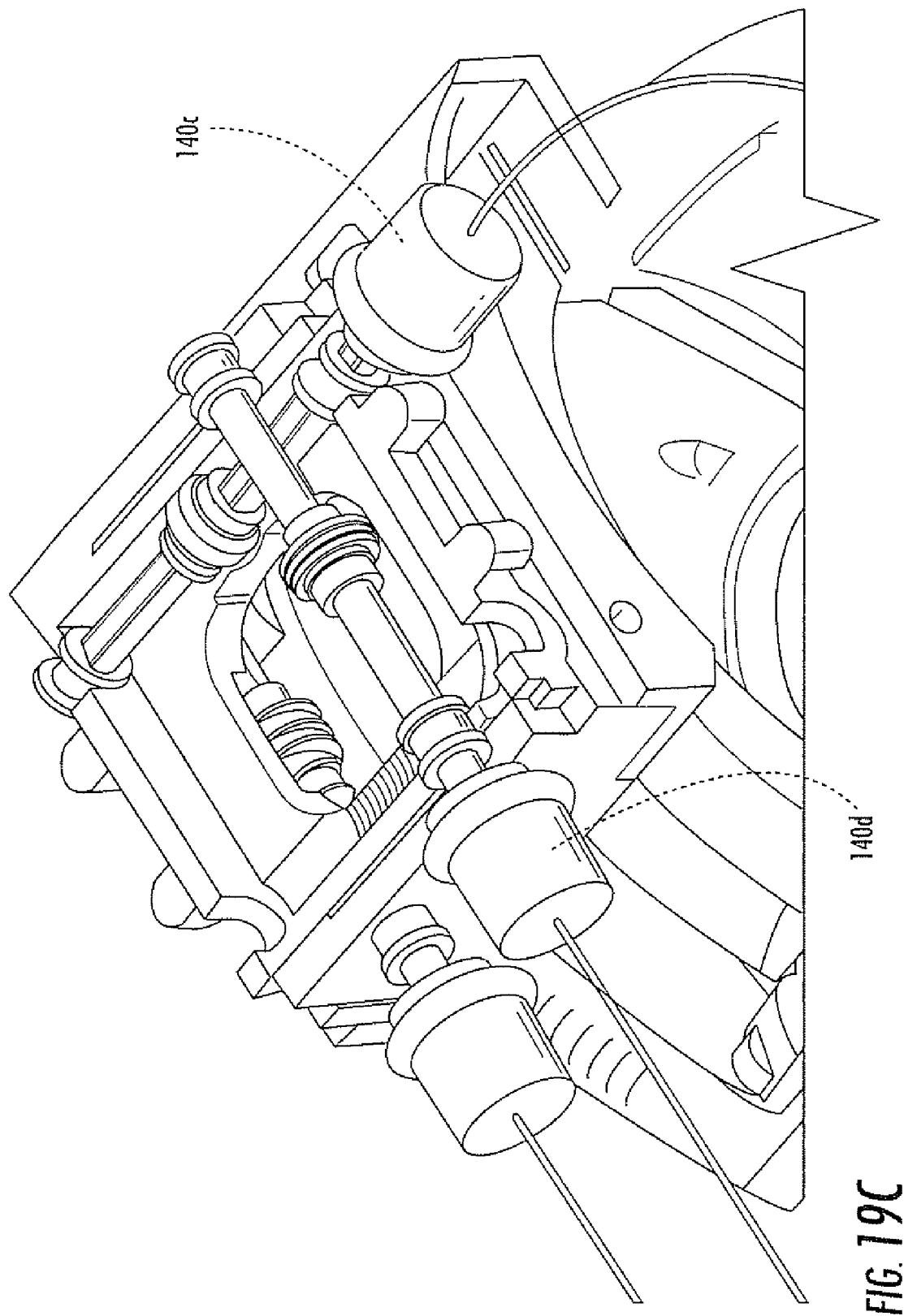
FIG. 19C is partial perspective view of an X-Y support table, according to some embodiments, with elements removed to reveal internal components of an X-direction actuator and Y-direction actuator.
Figure 20:
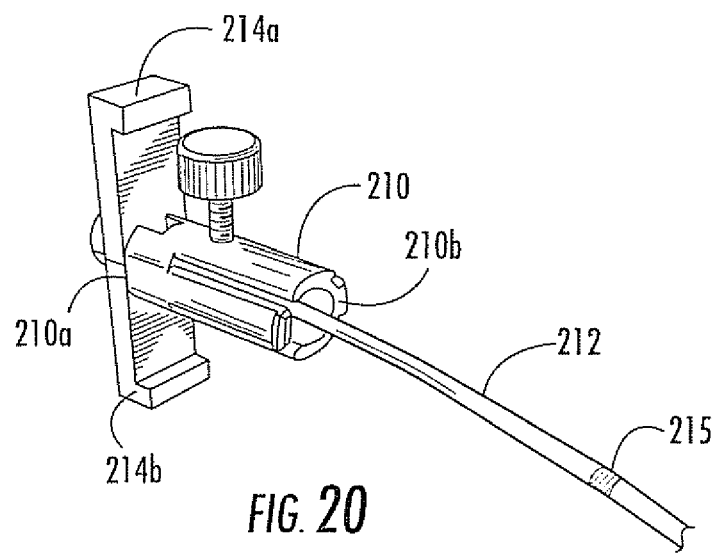
FIG. 20 illustrates a depth stop with a peel-away sheath inserted therein, according to some embodiments of the present invention.

Various internal drive mechanisms may be utilized for causing translational movement of the moving plate 134 in response to user rotation of the X-direction actuator 140c and the Y-direction actuator 140d. For example, drive belts, linkages, gears, or worm drives may be utilized, as would be understood by one skilled in the art of X-Y tables, Embodiments of the present invention are not limited to any particular mechanism for translating the X-Y table 132 along the X and Y directions. FIG. 19C is partial perspective view of an X-Y support table, according to some embodiments, with elements removed to reveal internal components of an X-direction actuator 140c and Y-direction actuator 140d.

As illustrated in FIG. 3A, the roll actuator 140a, pitch actuator 140b, X-direction actuator 140c, and Y-direction actuator 140d each extend outwardly from the frame 100 along the same direction (e.g., upwardly from the platform 130). This configuration facilitates easy connection of the control cables 150a-150d to the actuators 140a-140d (where used) and also facilitates bundling of the cables 150a-150d to reduce clutter or provide ease of handling and set-up. Embodiments of the present invention are not limited to the illustrated embodiment, however. The actuators 140a-140d may extend in various directions and these directions may be different from each other. In addition, the actuators 140a-140d may extend along the same direction from the frame, but in a different direction than that illustrated in FIG. 3A. For example, FIG. 16 illustrates an embodiment where the actuators 140a-140d extend from a common side of the platform 130.

Referring to FIGS. 9 and 10A-10C, the remote control unit 400 of the illustrated system 50 includes a plurality of manually-operable position controls 402a-402d. Specifically, the control unit 400 includes a roll adjustment control 402a, a pitch adjustment control 402b, an X-direction adjustment control 402c, and a Y-direction adjustment control 402d. A roll control cable 150a is operably connected to the roll adjustment control 402a and to the roll actuator 140a such that movement of the roll adjustment control 402a operates the roll actuator 140a via the roll control cable 150a. A pitch control cable 150b is operably connected to the pitch adjustment control 402b and to the pitch actuator 140b such that movement of the pitch adjustment control 402b operates the pitch actuator 140b via the pitch control cable 150b. An X-direction control cable 150c is operably connected to the X-direction control 402c and to the X-direction actuator 140c such that movement of the X-direction adjustment control 402c operates the X-direction actuator 140c via the X-direction control cable 150c. A Y-direction control cable 150d is operably connected to the Y-direction control 402d and to the Y-direction actuator 140d such that movement of the Y direction adjustment control 402d operates the Y-direction actuator 140d via the Y-direction control cable 150d.

In the illustrated embodiment, each of the position controls 402a-402d is a thumbwheel control that can be rotated by a user's finger in clockwise and counterclockwise directions. Rotation of each thumbwheel 402a-402d by a user causes corresponding axial rotation of a respective control cable 150a-150d and corresponding axial rotation of a respective actuator 140a-140d.

Figure 10B:
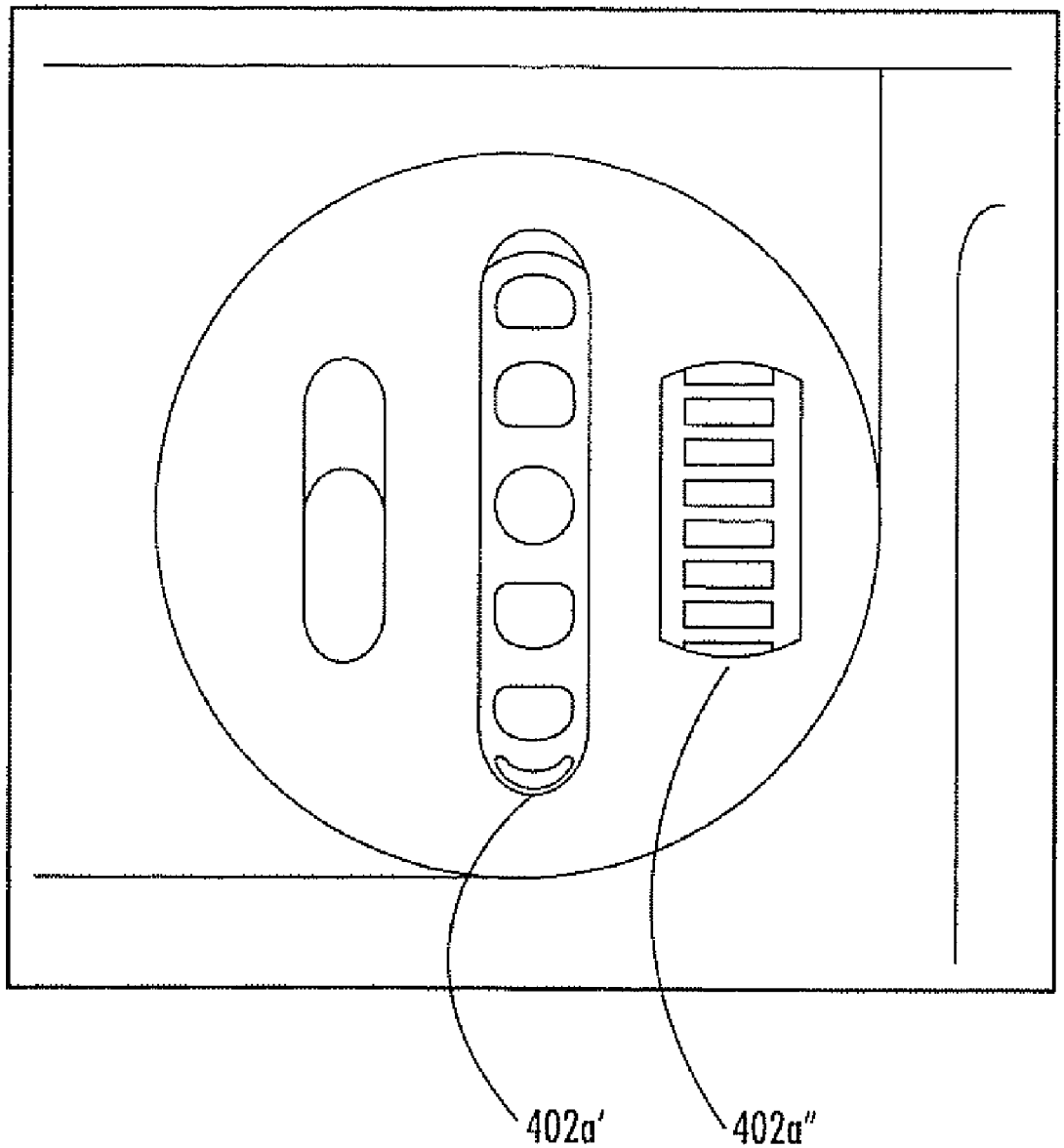
Figure 10C:
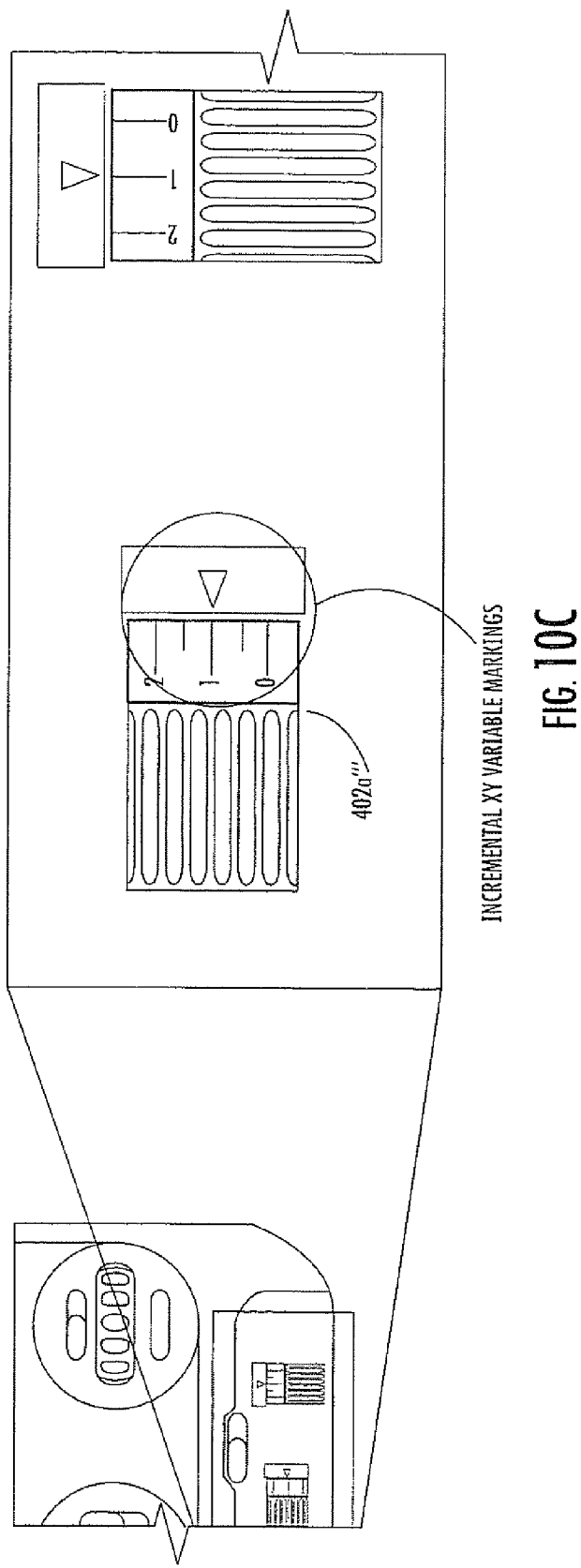

FIG. 10B illustrates position controls, according to additional embodiments of the present invention, that utilize two thumbwheels. One thumbwheel 402a' is for "fine" adjustments; the other thumbwheel 402a" is for "gross" adjustments. The amount of fine and gross adjustment is correlated to the diameter of each thumbwheel, as would be understood by one skilled in the art. FIG. 10C illustrates a position control 402a''', according to additional embodiments of the present invention, that indicates incremental X-Y variable markings.

In the illustrated embodiment, locking mechanisms 404a-404c are associated with the thumbwheels 402a-402d and prevent user rotation thereof when in a locked position. For example, a locking mechanism 404a is operably associated with the roll adjustment control 402a and is configured to prevent rotation thereof by a user when in a "locked" position. Locking mechanism 404b is operably associated with pitch adjustment control 402b and is configured to prevent rotation thereof by a user when in a "locked" position. Locking mechanism 404c is operably associated with X-direction control 402c and Y-direction control 402d and is configured to prevent rotation of X-direction control 402c and Y-direction control 402d by a user when in a "locked" position.

Figure 15:
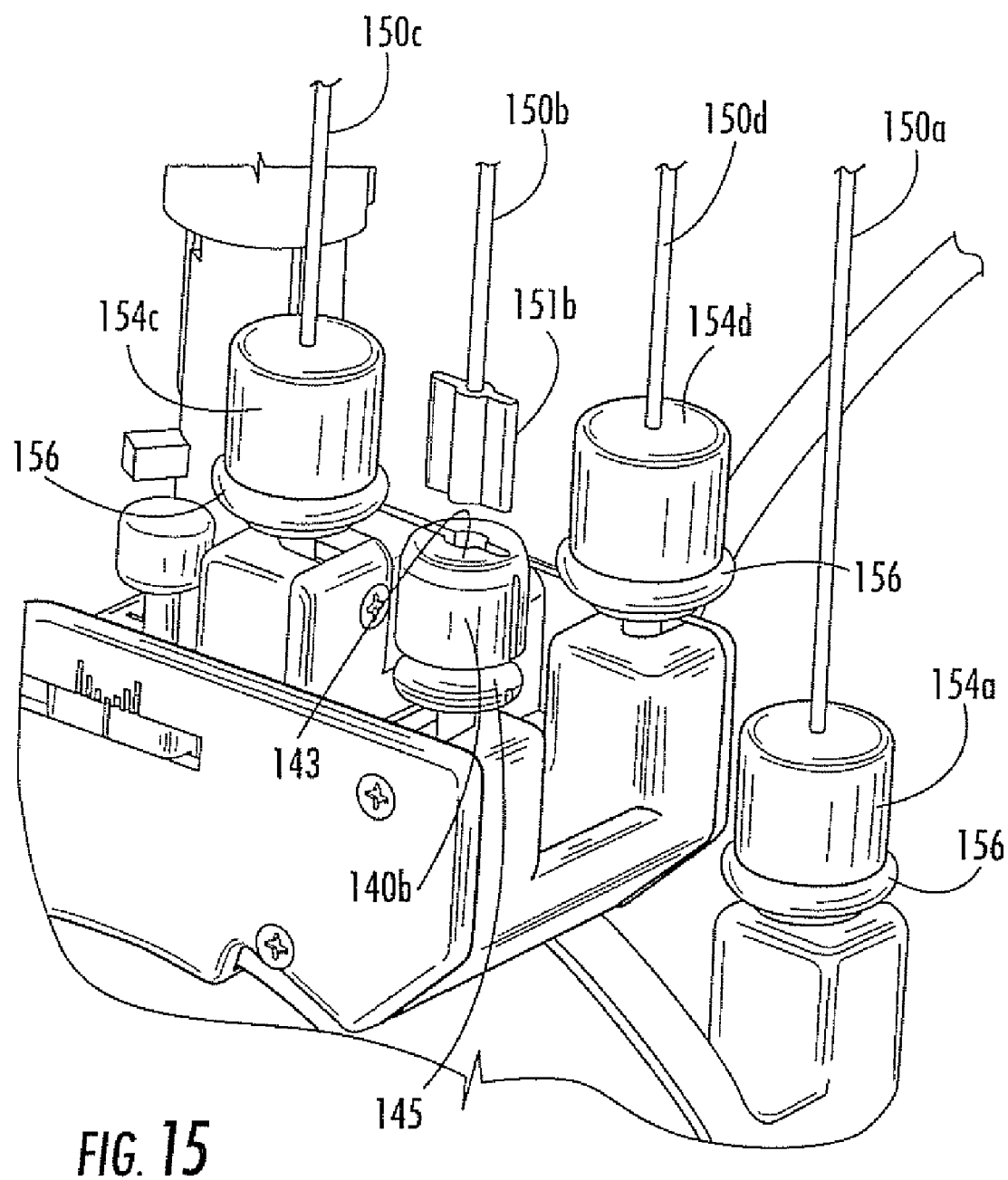
FIG. 15 is an enlarged, partial perspective view of the frame of FIG. 3A illustrating control cables removably engaged with respective actuators, and illustrating flexible elastomeric collars configured to surround respective actuator free ends and to maintain engagement of the cable ends to a respective actuator free end, according to some embodiments of the present invention.

Each control cable 150a-150d can have a geometrically shaped rigid end 151a-151d that is configured to removably engage a free end of a respective actuator 140a-140d. As illustrated in FIG. 16, the respective free ends 141a-141d of the actuators 140a-140d may have a slot 143 formed therein that is configured to removably receive a respective cable end. Exemplary cable end shapes include, but are not limited to, "L" shapes, "U" shapes, square shapes, rectangular shapes, oval/circular shapes, and other polygonal shapes. Each cable end has sufficient rigidity such that axial rotation of the cable causes the cable free end to impart rotational motion to a respective actuator. FIG. 15 illustrates the free end of cable 150b having a connector 151b with a geometric shape attached thereto that is configured to matingly engage a respective slot 143 in actuator 140b, according to other embodiments of the present invention.

In some embodiments, the free end of an actuator 140a-140d may be configured to receive only a specific one of the control cables 150a-150d. For example, in FIG. 15, the connector 151b may not fit within the slots 143 of any of the other actuators. As such, a control cable cannot be inadvertently connected to the wrong actuator. For example, the roll adjustment actuator free end 141a may be configured to only receive the free end 151a of the control cable 150a associated with the roll control 402a. Similarly, the pitch adjustment actuator free end 141b may be configured to only receive the free end 151b of the control cable 150b associated with the pitch control 402b.

Each control cable 150a-150d also has a flexible elastomeric (e.g., silicone, rubber, etc.) collar 154a-154d that is configured to surround a respective actuator 140a-140d and maintain engagement of the respective cable end 151a-151d within the respective actuator. Each elastomeric collar 154a-154d is configured to prevent removal of a cable by a user, for example, as a result of inadvertent tugging on the cable by a user, or by movement of the remote control unit 400. Each of the illustrated collars 154a-154d can be rolled or folded back then released to cover and conformably compress against an actuator to hold the end of a respective cable in position. Each collar 154a-154d can then be pushed back to easily release the cable from the actuator. In the illustrated embodiment, each actuator 140a-140d has a circumferential groove 145 configured to receive a corresponding circumferential ridge 156 of a collar 154a-154d in mating relation therewith.

Figure 16A:
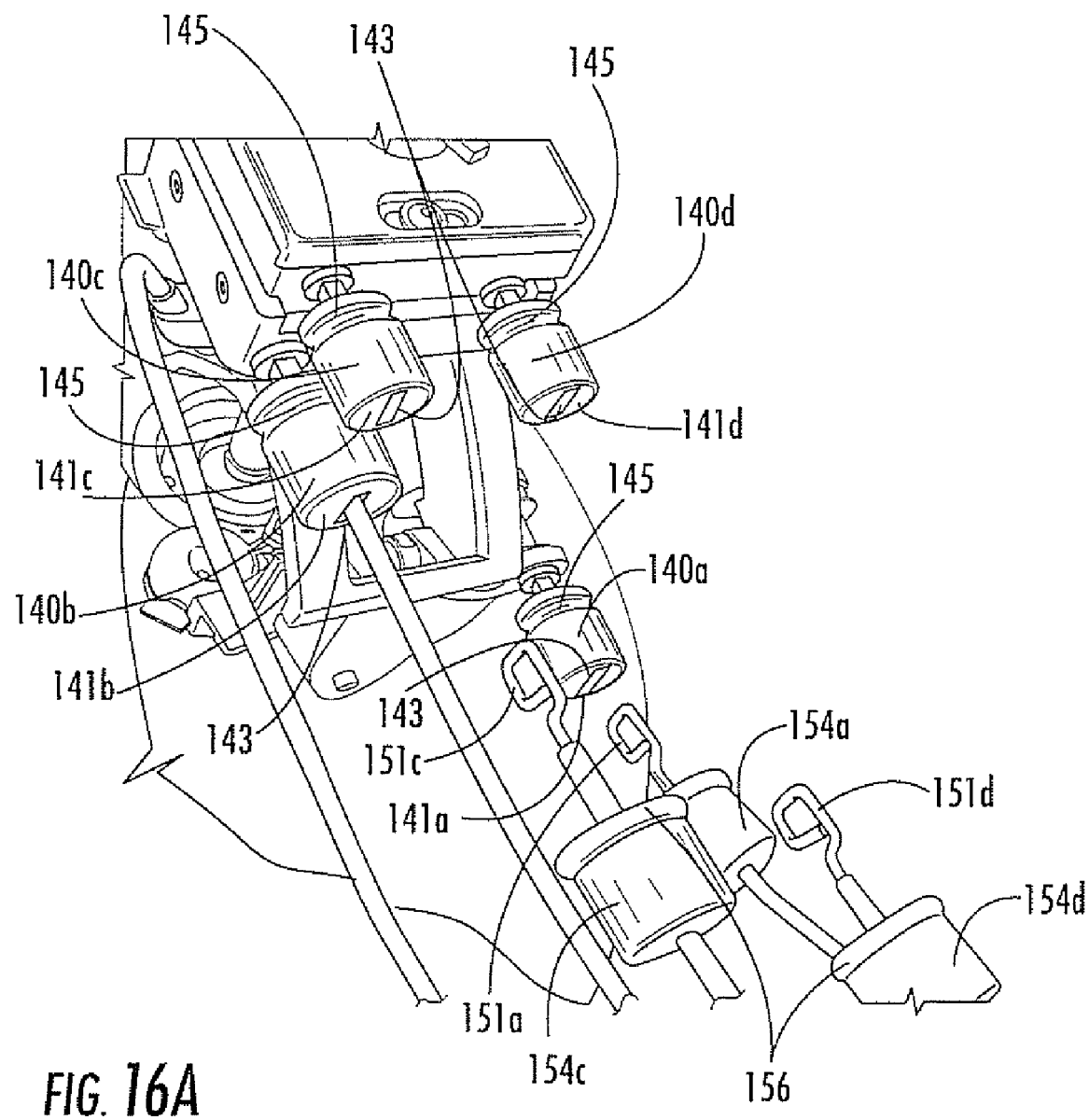
FIG. 16A is a partial perspective view of a frame of an MRI-guided interventional system, according to other embodiments of the present invention, and illustrating actuators positioned on a side of the frame and illustrating control cables removably engaged with the respective actuators.
Figure 16B:
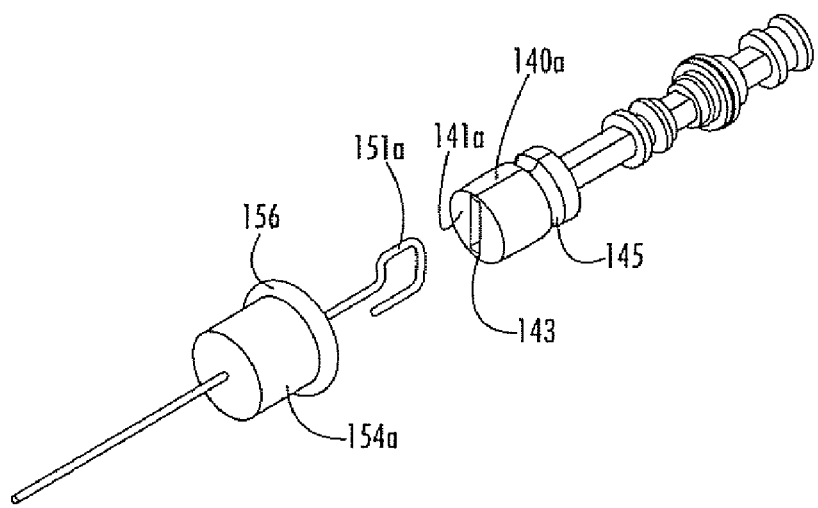
FIG. 16B is a partial perspective view of an exemplary prototype actuator illustrating a remote control cable end about to be inserted into a slot in the actuator free end, according to some embodiments of the present invention.
Figure 16C:
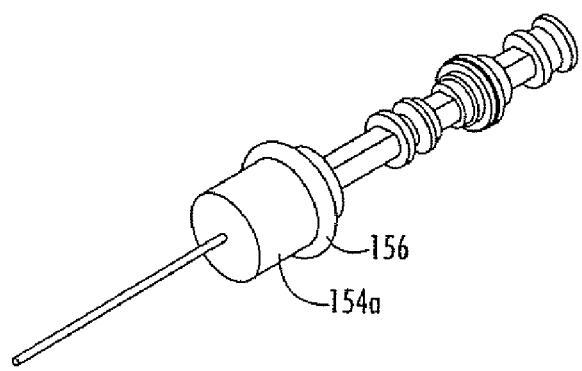
FIG. 16C is a partial perspective view of the actuator of FIG. 16B with the remote control cable end inserted into the actuator and with an elastomeric collar engaging the free end of the actuator to prevent the cable from being inadvertently removed from the actuator.
Figure 16D:
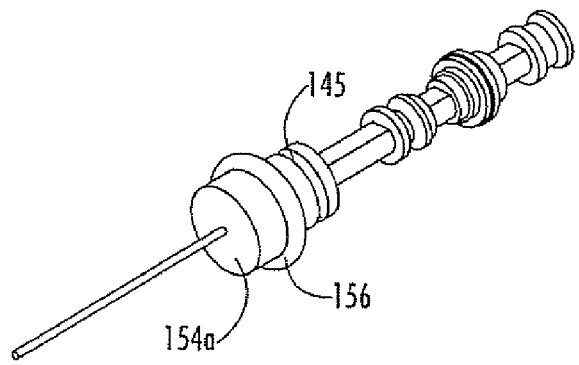
FIGS. 16D-16E are partial perspective views of the actuator of FIG. 16C illustrating removal of the elastomeric collar and cable (FIG. 16E) from the free end of the actuator.
Figure 16E:
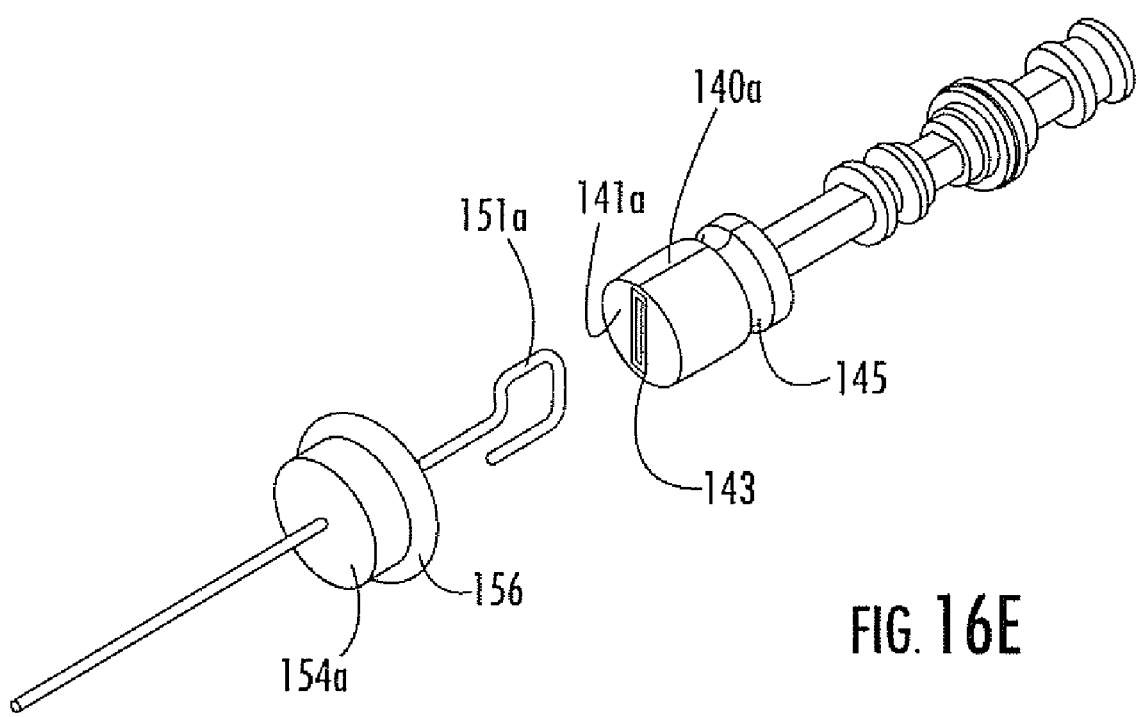

FIG. 16B illustrates remote control cable end 151a about to be inserted into slot 143 in the actuator free end 141a. The cable end 151a is inserted into the slot 143 and then the elastomeric collar 154a is fitted around the actuator 140a such that the circumferential ridge 156 engages the circumferential actuator groove 145, as illustrated in FIG. 16C. Because of the elastomeric nature of the collar 154a, the collar snuggly fits the actuator 140a and retains the cable end 151a within slot 143. To remove the cable end 151a, the circumferential ridge 156 is pulled out of the groove 145 and the collar 154a is rolled back on itself as illustrated in FIGS. 16D-16E.

Embodiments of the present invention are not limited to the illustrated elastomeric collars 154a-154d. Other ways of retaining the cable ends 151a-151d within respective actuators 140a-140d may be utilized without limitation.

In some embodiments, the actuators 140a-140d are color coded such that each actuator has a different respective color for easy identification by a user. For example, the roll actuator 140a may be colored red and the pitch actuator 140b may be colored yellow such that a user can easily identify the two respective actuators when positioning the frame 100. In some embodiments, the elastomeric collars 154a-154d may also be color coded so as to match the color of a respective actuator 140a-140d. In some embodiments, the cable ends 151a-151d may also be color coded so as to match the color of a respective actuator 140a-140d.

In some embodiments of the present invention, the control cables 150a-150d are formed of NITINOL or other MR-compatible materials. One or more portions of the frame 100 and the targeting cannula 200 may also be formed of NITINOL or other MR-compatible (non-paramagnetic) materials, such as plastics and other polymeric materials.

Figure 31:
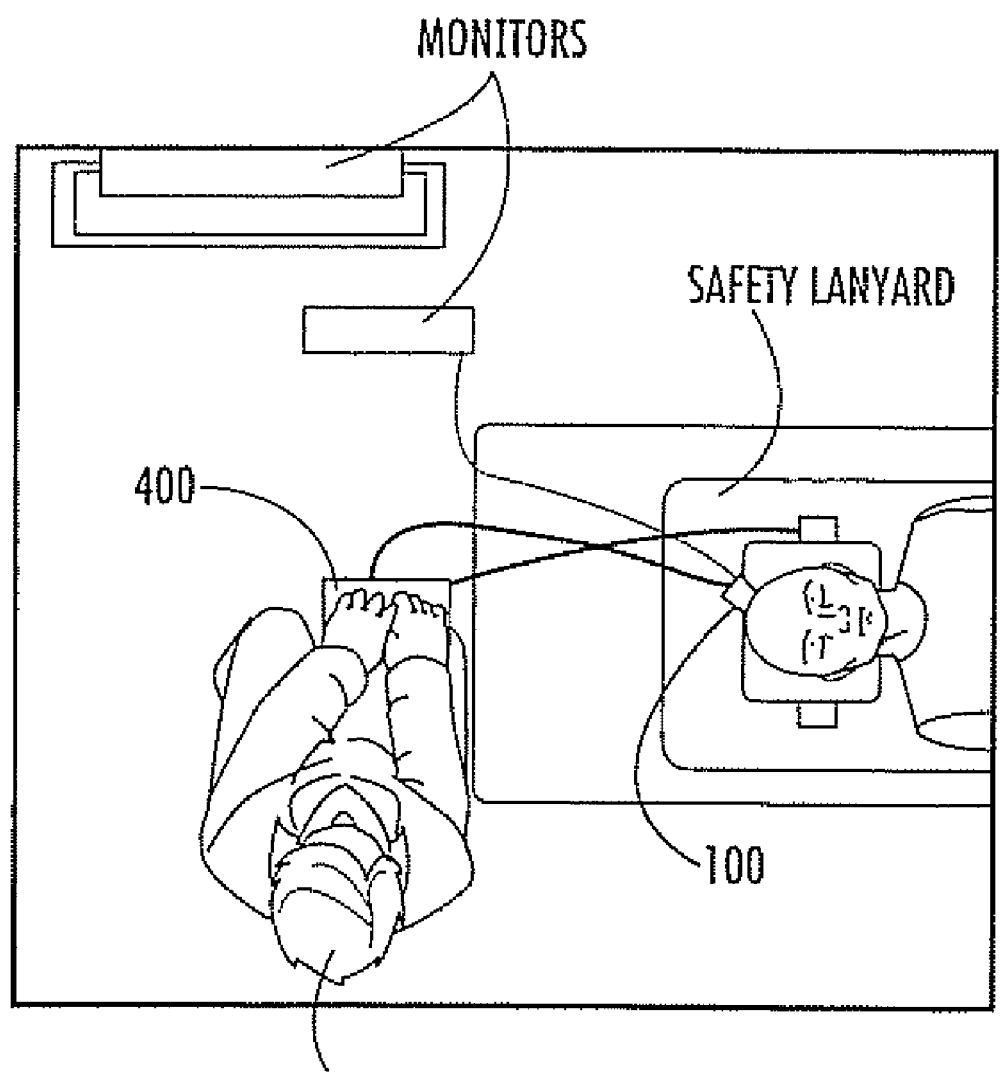
FIG. 31 is a schematic illustration of a patient positioned within an MRI scanner and a user utilizing a remote control apparatus 400 and display monitors to position a targeting cannula, according to some embodiments of the present invention.

FIG. 31 illustrates a patient positioned within an MRI scanner and a user utilizing the remote control apparatus 400 and display monitors to adjust the trajectory a targeting cannula, according to some embodiments of the present invention.

Figure 32A:
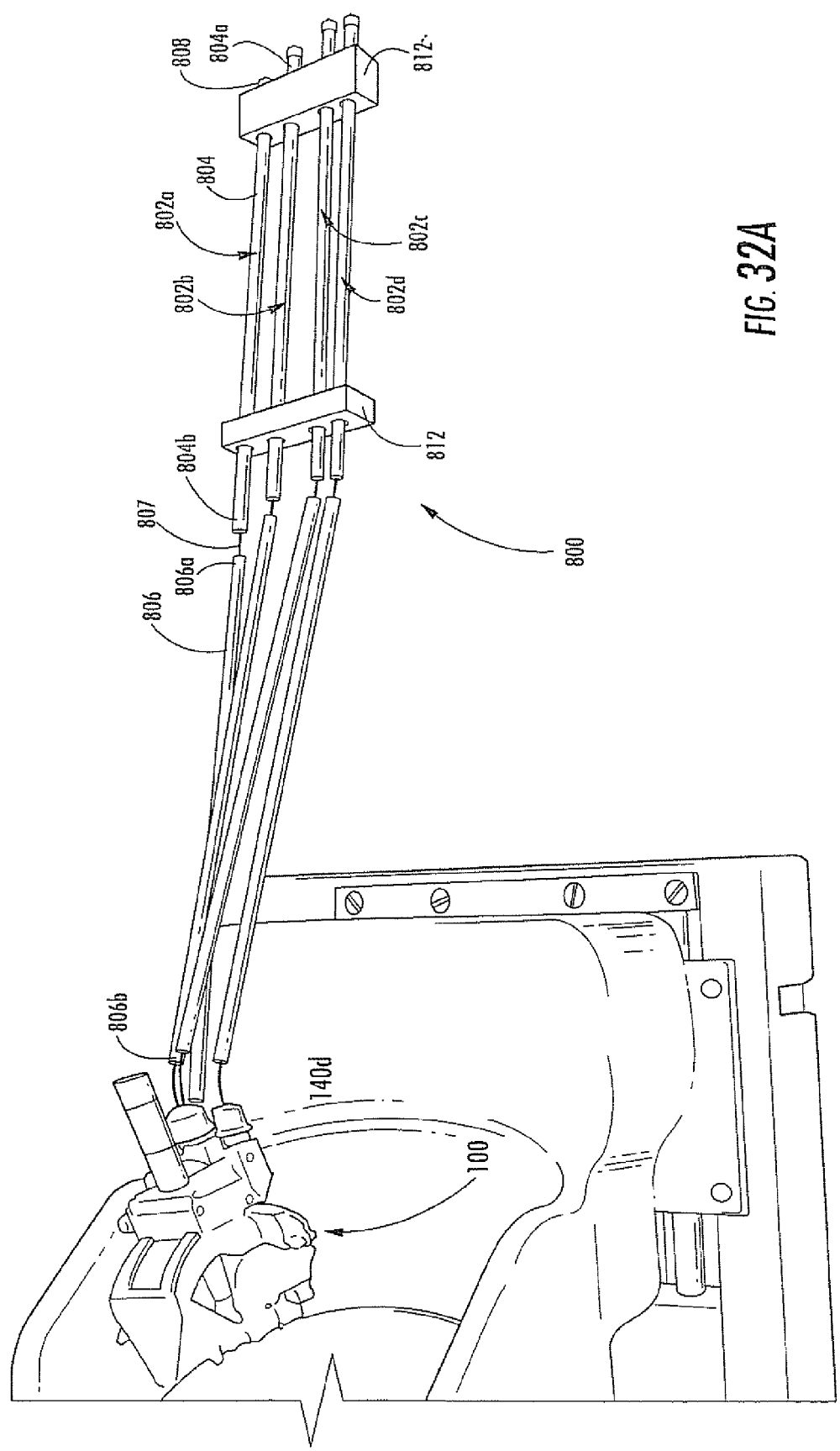
Figure 32B:
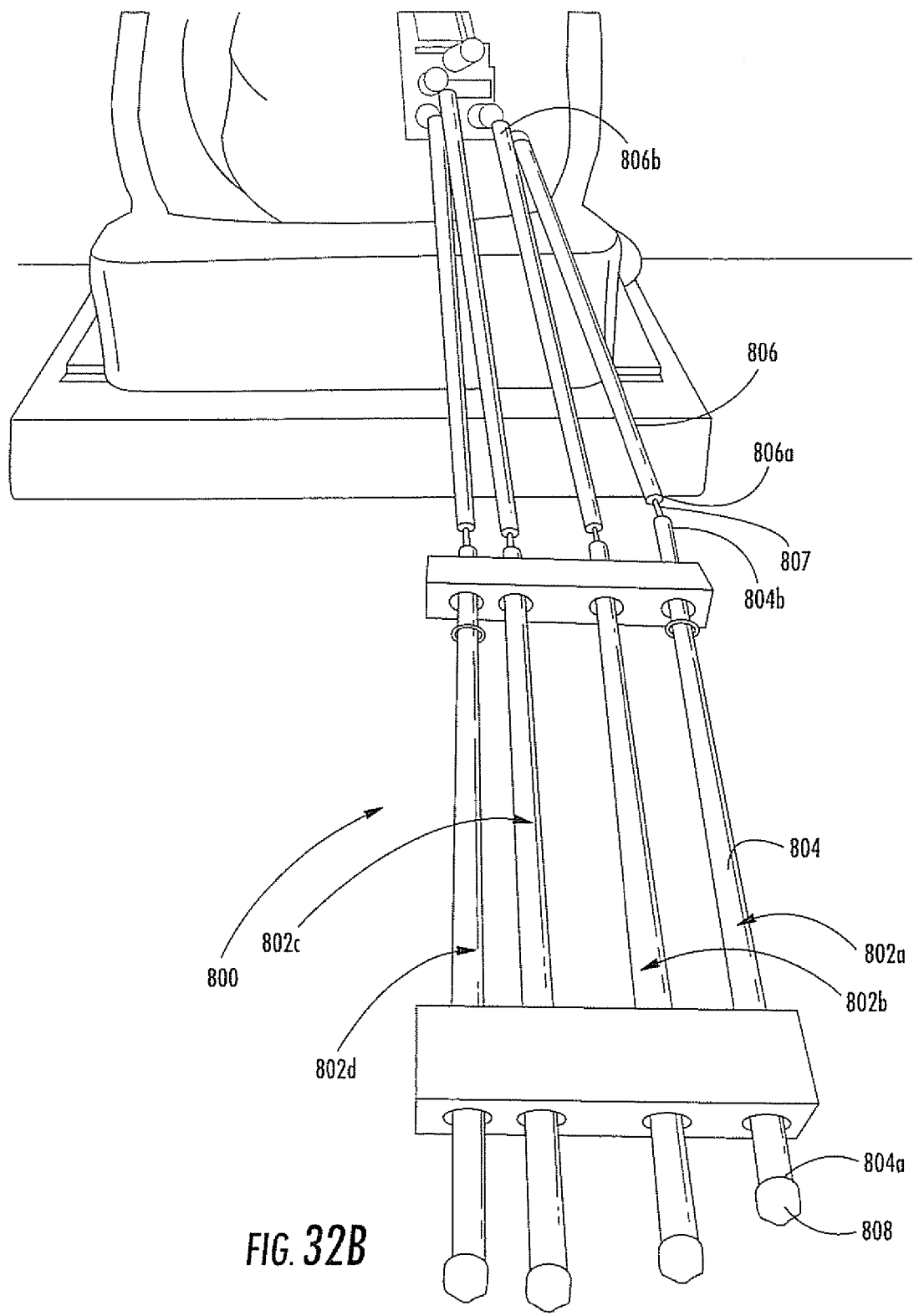

FIGS. 32A-32C illustrate a remote control unit 800 for remotely controlling the positioning actuators of the frame of FIG. 3A, according to other embodiments of the present invention. The illustrated remote control unit 800 includes a separate, multi-rod control device 802a-802d for each respective actuator 140a-140d. Each of the control devices 802a-802d can be identical in structure and, as such, only one will be described in detail hereinafter. However, each control device 802a-802d may be color coded with a color different from the other control devices 802a-802d, and each control device 802a-802d may have different lengths, shapes or sizes for ease of assembly and/or operation. Moreover, each control device 802a-802d may be color coded so as to match the color of a respective actuator 140a-140d.

Each control device 802a-802d includes a pair of elongated rods 804, 806 (e.g., solid, MRI-compatible rods) joined at respective ends via a flexible member such as a cable 807, as illustrated. The rods 804, 806 may be formed of wood, polymeric material, or other suitable relatively lightweight MRI-compatible material. In addition, the rods 804, 806 are not required to be solid.

The cable 807 is relatively short in length relative to the length of rods 804, 806 and serves as a universal joint to allow the two rods 804, 806 to rotate even when oriented transverse to each other. For example, the cable 807 may be between about one quarter inch and about one inch (0.25"-1") in length. However, embodiments of the present invention are not limited to this range for the length of cable 807; cable 807 may have other lengths. In some embodiments, the cable 807 is an MRI-compatible cable (e.g., NITINOL, etc.). In the illustrated embodiment, the distal end 804b of rod 804 is joined to the proximal end 806a of rod 806 via cable 807. The cable 807 may be joined to rods 804, 806 in any of various ways including, but not limited to, via adhesives, via fasteners, via threaded connections, etc.

The proximal end 804a of rod 804 includes an endcap 808 secured thereto. The endcap 808 may be formed from tactile material to facilitate rotation of rod 804 by a user. A knob or other device that facilitates rotation may be secured to the proximal end of rod 804 in lieu of endcap 808, in other embodiments. In operation, a user rotates the proximal end 804a of rod 804 in a clockwise or counterclockwise direction to correspondingly rotate actuator 140a.

The distal end 806b of rod 806 is joined to actuator 140a via a flexible member such as a cable 810, as illustrated. The cable 810 is relatively short in length relative to the length of rod 806 and serves as a universal joint to allow rod 806 to rotate even when oriented transverse to actuator 140a. In some embodiments, the cable 810 is an MRI-compatible cable. For example, the cable 810 may be between about one half inch and about one and one half inch (0.5"-1.5") in length. However, embodiments of the present invention are not limited to this range for the length of cable 810; cable 810 may have other lengths.

Cable 810 may be joined to rod 806 in any of various ways including, but not limited to, via adhesives, via fasteners, via threaded connections, etc. The free end of cable 810 may have a rigid, geometrical shape, as described above with respect to the embodiments of cables 150a-150d, and may be configured to engage a slot within the actuator 140a, as described above. An elastomeric collar, as described above with respect to FIGS. 16A-16E, may or may not be necessary to retain the free end of cable 810 within actuator 140a. In the illustrated embodiment, an elastomeric collar is not utilized. When used, an elastomeric collar can also be color coded to the actuator and/or control device rods 804, 806.

In the illustrated embodiment, the control devices 802a-802d are supported by a pair of spaced apart separator devices 812. Each separator device 812 includes a plurality of substantially parallel, spaced apart bores passing therethrough that are configured to receive each of the rods 804 for the respective control devices 802a-802d. The separator devices 812 are configured to maintain the rods 804 in substantially parallel, spaced apart relationship, as illustrated. In the illustrated embodiment, only rods 804 pass through the two separator devices 812. However, embodiments of the present invention are not limited to the illustrated use, configuration, location, or number of separation devices 812. In addition, although shown as two rods forming each control device 802a-802d, they may include three or more spaced apart rods (not shown), or only a single rod (not shown). Moreover, other types of devices may be utilized without limitation.

Figure 8A:
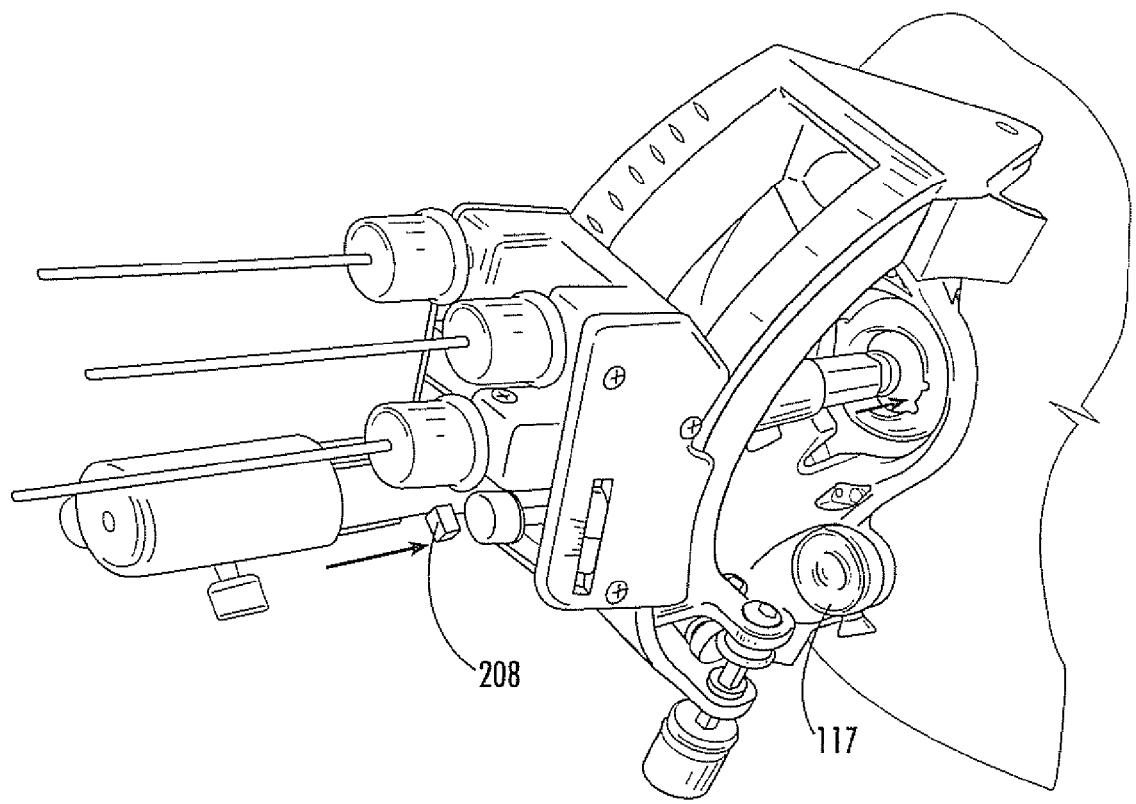
FIG. 8A is a perspective view of the frame of FIG. 3A secured to the body (e.g., skull) of a patient, and with the targeting cannula in an extended position.
Figure 14:
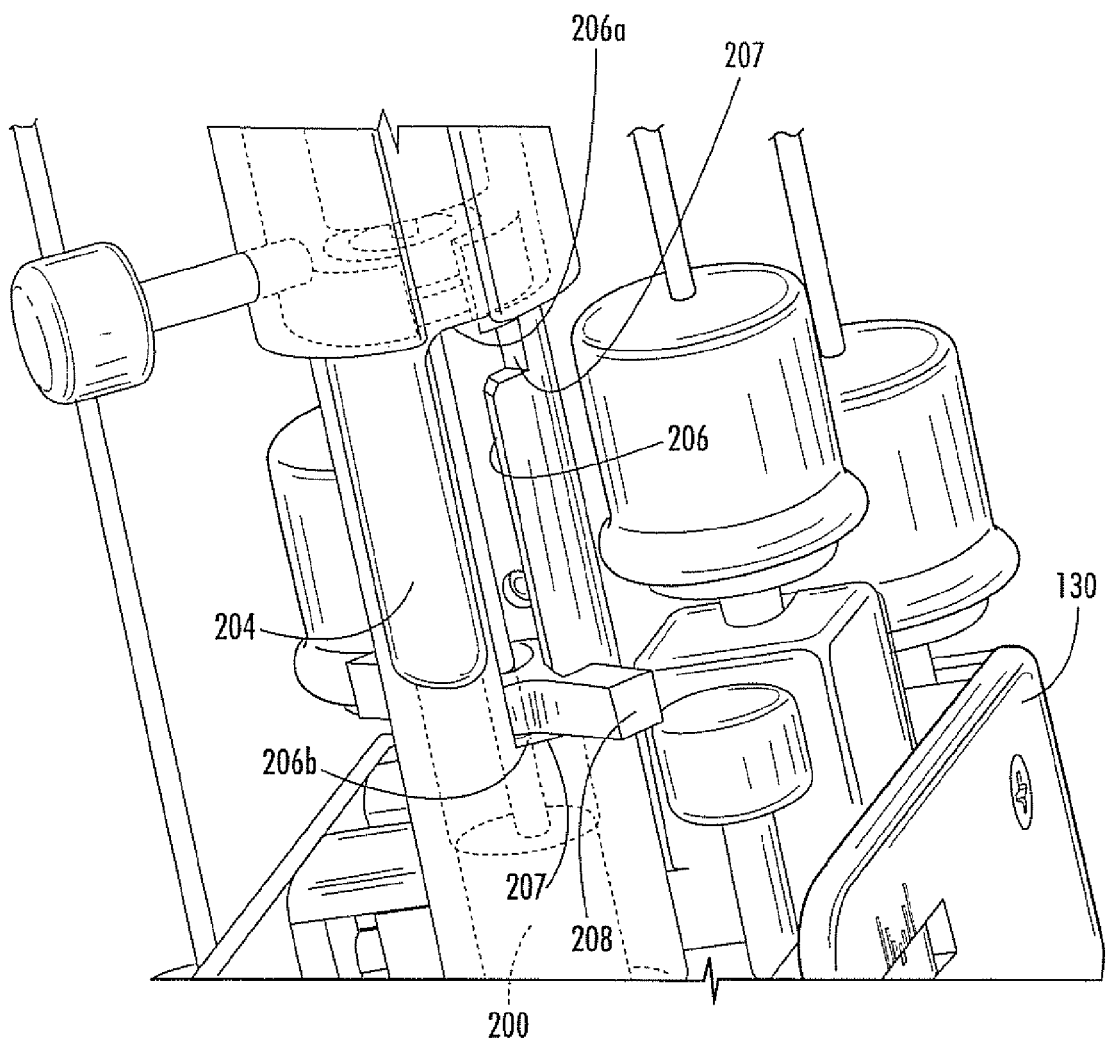
FIG. 14 is an enlarged, partial perspective view of the frame of FIG. 3A illustrating the targeting cannula locked in an extended position, according to some embodiments of the present invention.

Referring to FIGS. 14 and 19, an elongated tubular member 204 extends through the platform 130 and yoke 120 and is secured to the X-Y support table 132. The targeting cannula 200 is slidably secured within the tubular member 204 and is movable between extended and retracted positions. FIGS. 3A-3D and 4-6 illustrate the targeting cannula 200 in a retracted position above the burr hole 10 and FIGS. 3E and 8A illustrate the targeting cannula 200 in an extended position. The tubular member 204 is configured to lock the targeting cannula 200 in an extended position and in a retracted position, as illustrated in FIG. 14. The tubular member 204 has a pair of radially opposed elongated, axial-extending slots 206, as illustrated. The ends 206a, 206b of each slot 206 include a transverse portion 207 that is configured to retain the targeting cannula 200 in respective extended and retracted positions. The targeting cannula 200 includes a respective pair of radially extending prongs 208, as illustrated. Each prong 208 cooperates with a respective slot 206. When the targeting cannula 200 is moved upwardly to the retracted position, the targeting cannula 200 is rotated slightly (or the tubular member 204 is rotated slightly) such that prongs 208 each engage a respective transverse portion 207. When so engaged, the targeting cannula 200 is retained in the retracted position. When the targeting cannula 200 is moved downwardly to the extended position, the targeting cannula 200 is rotated slightly (or the tubular member 204 is rotated slightly) such that prongs 208 each engage a respective transverse portion 207. When so engaged, the targeting cannula 200 is retained in the extended position.

Embodiments of the present invention are not limited to the illustrated configuration or number of slots 206 in the tubular member 204 or to the number of prongs 208 extending from the targeting cannula 200. For example, the targeting cannula 200 may have a single prong 208 that is configured to cooperate with a respective single slot 206 in the tubular member 204. In addition, slot 206 may have a different configuration than illustrated.

Referring to FIGS. 20-26, a depth stop 210 with a removable sheath 212 inserted and secured therein is illustrated. The illustrated depth stop 210 has a generally cylindrical configuration with opposite proximal and distal ends 210a, 210b and is adapted to be removably secured within the proximal end 204a of the tubular member 204. The depth stop 210 is configured to limit a distance that the sheath 212 extends into the body of a patient when the depth stop is inserted within the tubular member 204. The sheath 212 is configured to receive and guide an elongated interventional device therethrough, as will be described below. The sheath 212 includes opposing tabs 214a, 214b that, when pulled apart, cause the sheath 212 to peel away for removal from the targeting cannula 200.

Figure 21:
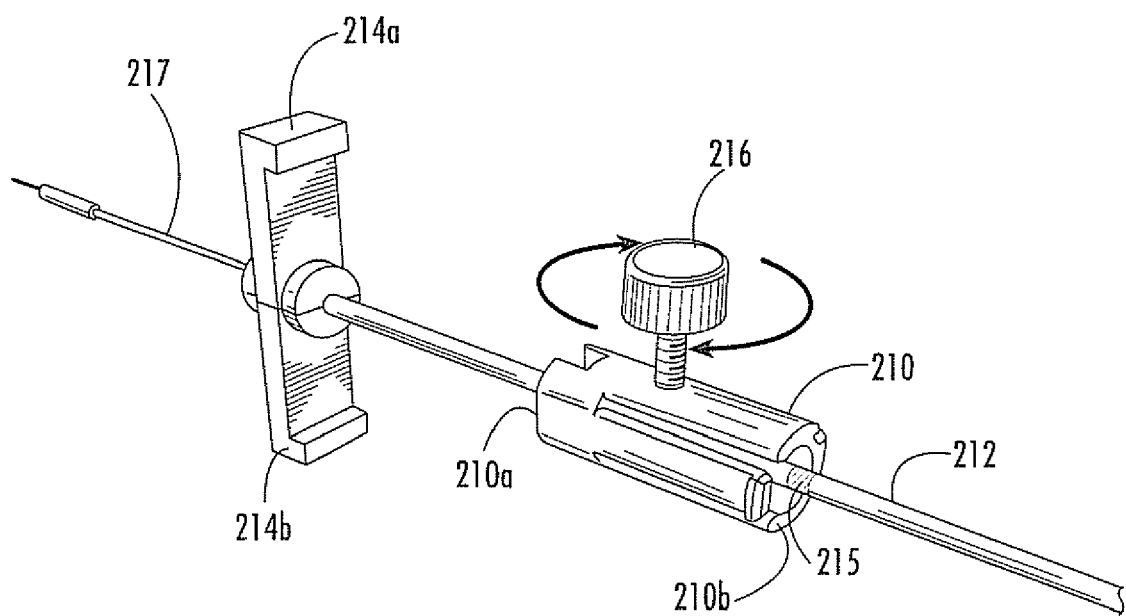
FIG. 21 illustrates an imaging probe inserted within the peel-away sheath of FIG. 20 and with the depth stop advanced to a depth mark on the peel-away sheath, according to some embodiments of the present invention.

Prior to insertion within the tubular member 204, the distal end 210b of the depth stop 210 is positioned adjacent to a mark 215 on the removable sheath 212, as illustrated in FIG. 21. Locking screw 216 is then tightened to prevent axial movement of the sheath 212 relative to the depth stop 210. An elongate location verification probe 217, such as an imaging probe, is then inserted within the sheath 212 as illustrated in FIG. 21.

Figure 22:
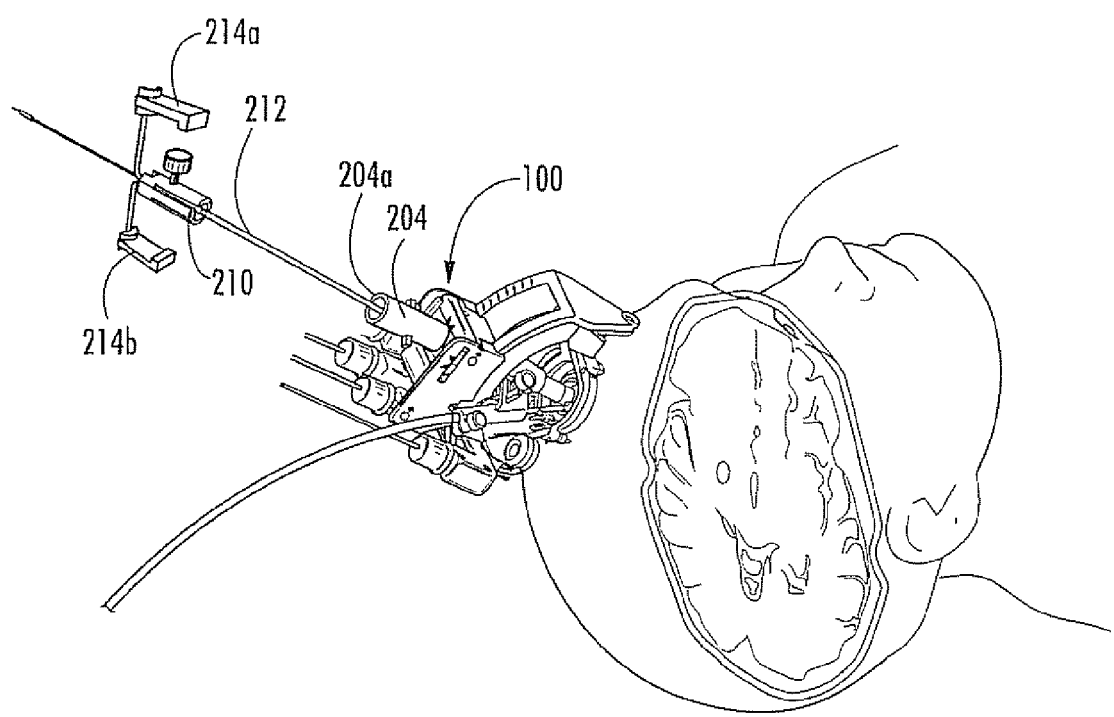
FIG. 22 illustrates the depth stop and probe being inserted into the targeting cannula of the frame of FIG. 3A.
Figure 23:
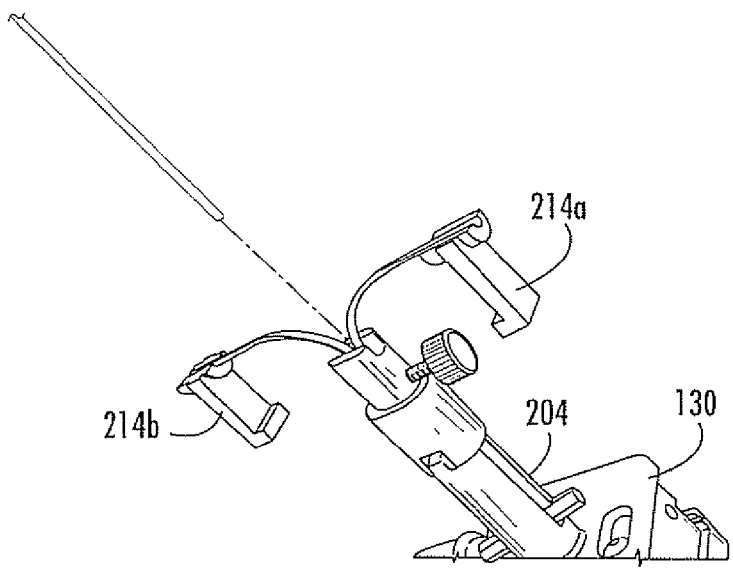
FIG. 23 illustrates the probe of FIG. 22 being removed from the peel-away sheath and depth stop.
Figure 24:
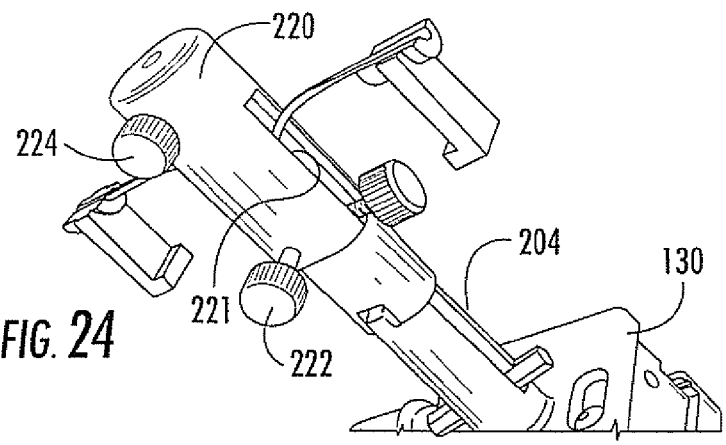
FIG. 24 illustrates a lead lock secured to the depth stop of FIG. 23.

Referring to FIGS. 22-23, the opposing tabs 214a, 214b of the sheath are pulled apart slightly, and the depth stop 210, sheath 212 and imaging probe 217 are inserted into the proximal end 204a of tubular member 204. When so inserted, as illustrated in FIG. 23, the sheath 212 and imaging probe 217 pass through the axial bore of the targeting cannula 200. The imaging probe 217 is then utilized to verify that the distal end 212b of the sheath 212 is positioned at the correct location within the body of a patient. Upon verifying that the sheath 212 is accurately positioned, the imaging probe 217 is removed (FIG. 23).

The probe 217 extending through the targeting cannula guide bore can include at least one electrode (which may include a coil winding) on a distal tip portion thereof. The electrode can be a recording and/or stimulating electrode. The electrode can be configured to deliver test voltages for physiologic confirmation of location/efficacy that can be done by fMRI or by feedback from a non-anesthetized patient. Thus, a patient can be stimulated with an interventional probe (the stimulation may be via a transducer on a distal tip portion of the probe), to help confirm that the interventional probe is in the correct location (i.e., confirm proper location via anatomical as well as provide physiologic information and feedback). During (and typically substantially immediately after) stimulation from the interventional probe, the physician can monitor for a physiologic response from the patient that can be observed either directly from the patient as a physical response or via an fMRI-visible response.

The elongate probe 217 can be MRI-visible and may optionally be configured to define an MRI antenna. The system 50 can be configured to allow for real-time tracking under MRI, with an SNR imaging improvement in a diameter of at least 1-10 mm surrounding the probe.

Next, a locking mechanism 220 is removably secured to the proximal end 210a of the depth stop 210. The locking mechanism 202 includes opposing axially extending slots 221, as illustrated. The portions of the sheath 212 that have been peeled away extend through these slots as illustrated. The locking mechanism 220 is secured to the depth stop/tubular member via locking screw 222.

Figure 25:
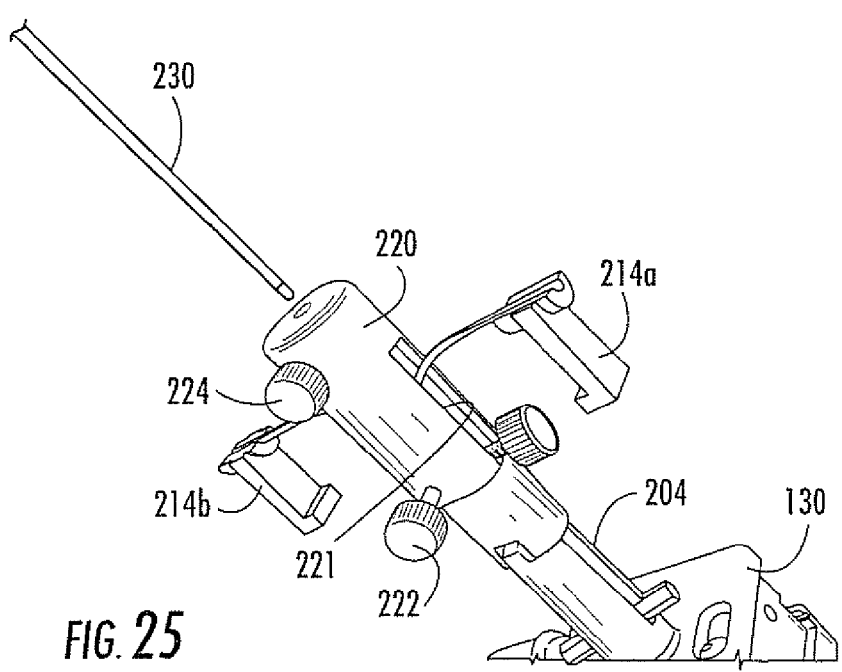
FIG. 25 illustrates a lead being inserted through the lead lock of FIG. 24 and through the targeting cannula.

The targeting cannula 200 is now ready to receive an interventional device therein. As illustrated in FIG. 25, an interventional device 230, such as a brain stimulation lead, is inserted into the locking mechanism and through the removable sheath 212. A locking screw 224 is tightened to secure the interventional device 230 and prevent axial movement thereof.

The targeting cannula 200 can be MRI-visible. In some particular embodiments, the cannula 200 may optionally comprise a plurality of spaced apart microcoils configured to provide data used to provide 3-D dimensional data in MRI 3-D space, such as a trajectory, or 3-D spatial coordinates of position of the cannula 200. The microcoils can each provide data that can be correlated to a three-dimensional (X, Y, Z) position in 3-D space in the body. The microcoils can be in communication with the MRI scanner, and tracking sequences can be generated and data from one or more of the MRI scanner channels can be used to define positional 3-D positional data and a trajectory thereof.

In some particular embodiments, the progress of the cannula 200 and/or interventional probe 230 or other device may optionally be tracked in substantially real-time as it advances to the target via the coils (similar ones of which may also or alternatively be on or in the probe or other device) and/or antenna. However, realtime tracking may not be desired in some embodiments.

Figure 8B:
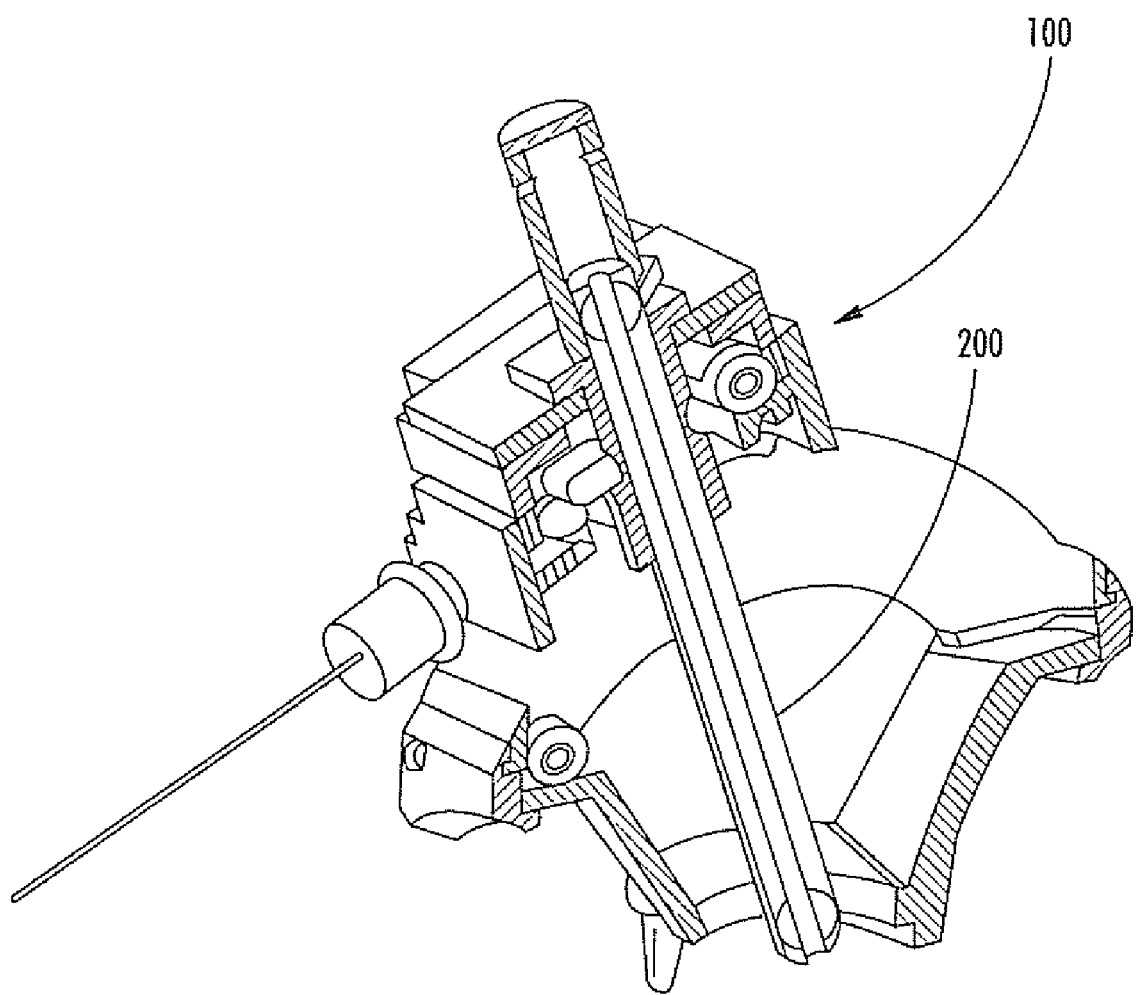
FIG. 8B is a cut-away perspective view of the frame of FIG. 3A, illustrating a targeting cannula according to some embodiments of the present invention.

In some embodiments, the cannula 200 can include at least one axially extending fluid-filled hollow lumen (FIG. 8B) or closed channel with fluid that can generate MRI signal that can be detected by an MRI scanner and/or by an internal MRI antenna incorporated on and/or into the cannula 200 that can increase the SNR of the fluid to increase its visibility in an MRI. The fluid may be an aqueous solution (able to resonate at the proton frequency). The cannula 200 can include an axially extending, relatively thin segment, which creates a high contrast MRI image (a segment filled with water or other suitable contrast solution filled section/lumen). The thickness of the segment may be between about 0.25-15 mm (and the segment can have a tubular shape with a diameter or may define another cross-sectional shape such as a square section). The cannula 200 may include MRI imaging coils to increase the signal from the high contrast fluid. See, e.g., co-pending U.S. patent application Ser. No. 12/066,862, which is incorporated here by reference in its entirety.

Figures 26A, 26B:
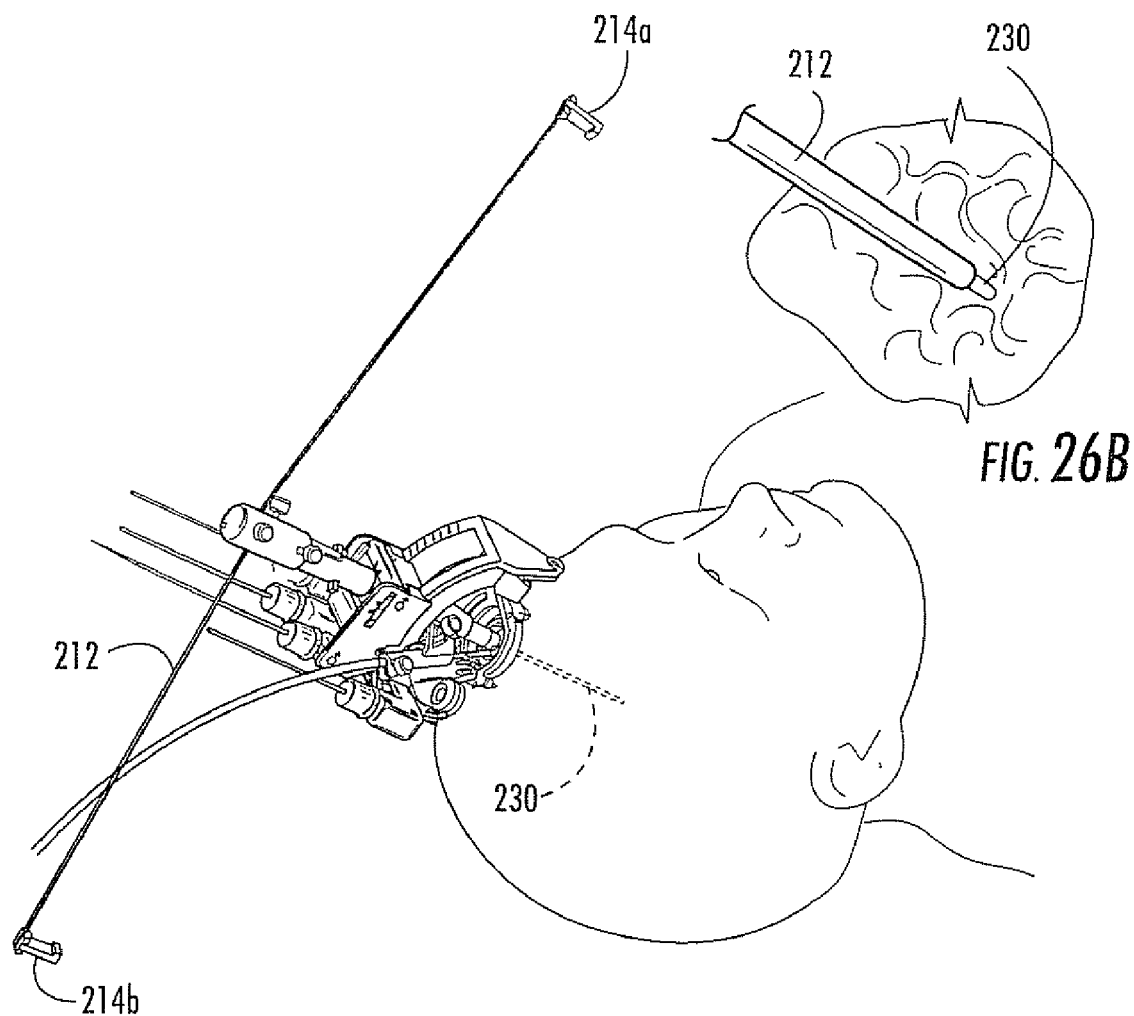
FIG. 26A is a perspective view of the frame of FIG. 3A with the lead of FIG. 25 inserted into the brain of a patient and with the peel-away sheath being removed, according to some embodiments of the present invention.
FIG. 26B is an enlarged view of the distal end of the peel-away sheath with the distal end of the lead extending therethrough, prior to removal of the sheath.
Figure 27:
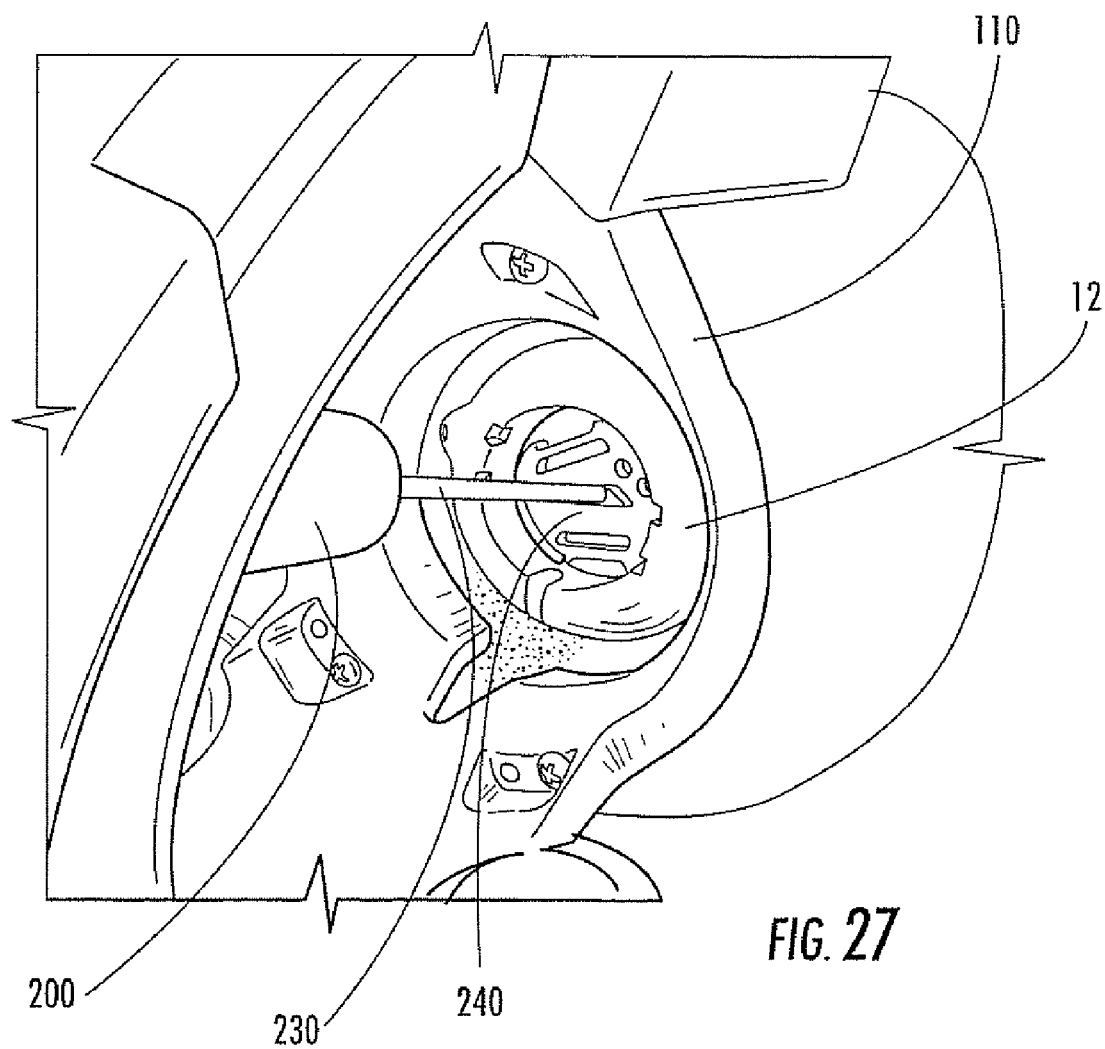
FIG. 27 illustrates a clamp inserted within and attached to the burr hole ring that is configured to prevent the lead from being retracted from the brain as the frame is removed from the skull of the patient.

As illustrated in FIGS. 26A and 26B, the interventional device 230 is positioned at the desired location within the body of a patient. The removable sheath 212 is then completely removed by pulling apart the opposing tabs 214a, 214b. A clamp 240 (FIG. 27) is inserted within the burr hole ring 12 that grips the interventional device 230 to prevent inadvertent removal of the interventional device 230 from the body of the patient. The clamp 240 is secured to the burr hole ring 12. The frame 100 can then be removed from the body of the patient, leaving behind only the interventional device 230 that has been inserted into the patient body.

Figure 28A:
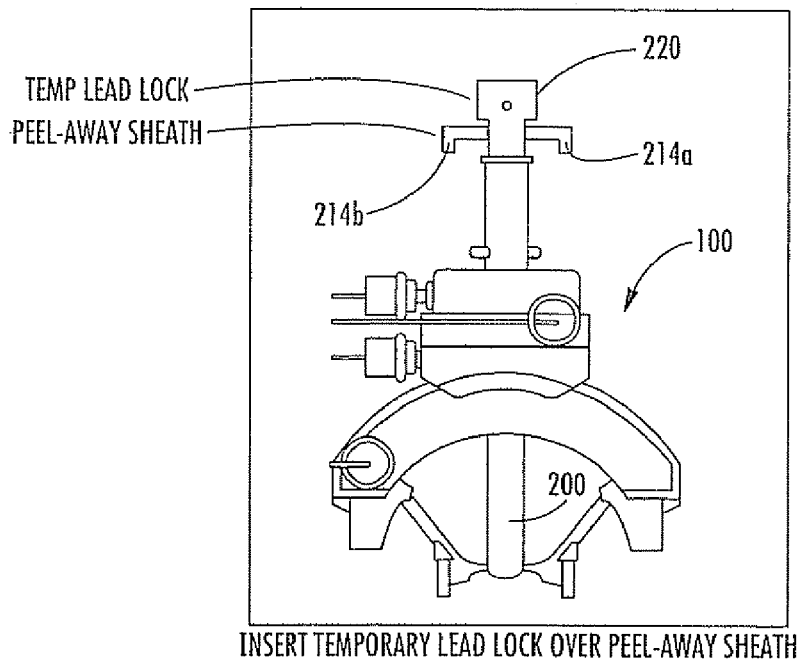
FIGS. 28A-28G are side view, schematic illustrations of the trajectory frame illustrating exemplary operation of the device for the insertion of interventional devices within the body of a patient via the targeting cannula.
Figure 28B:
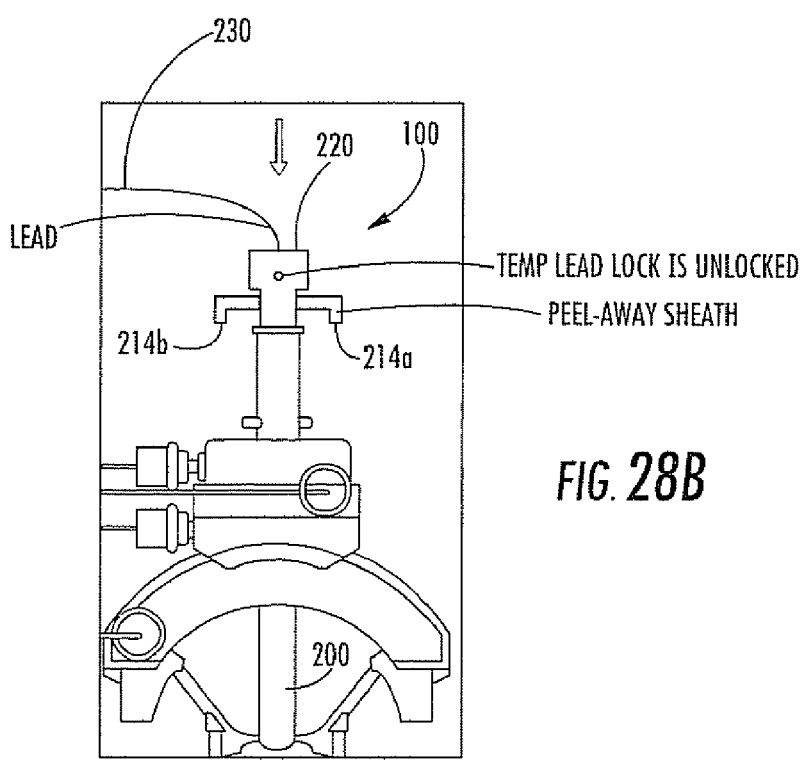
Figure 28C:
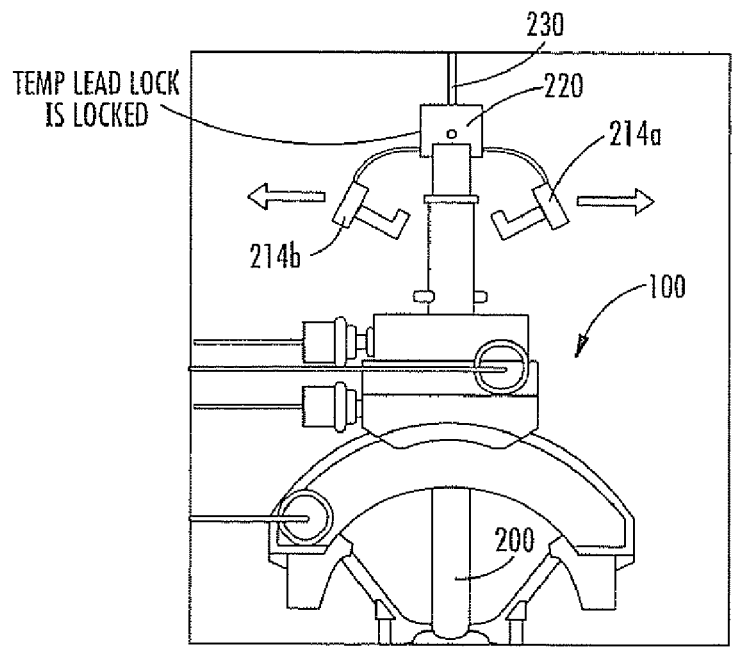
Figure 28D:
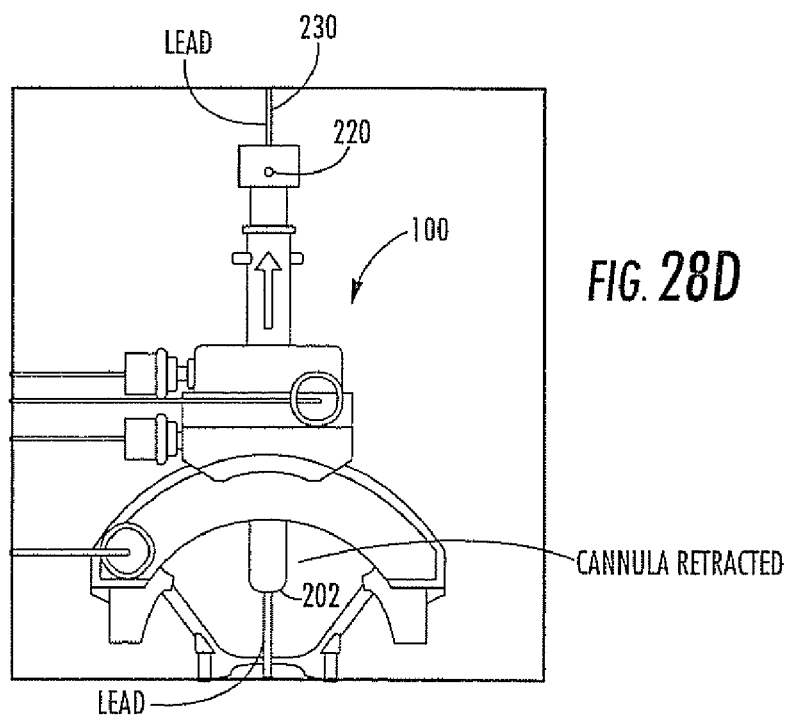
Figure 28E:
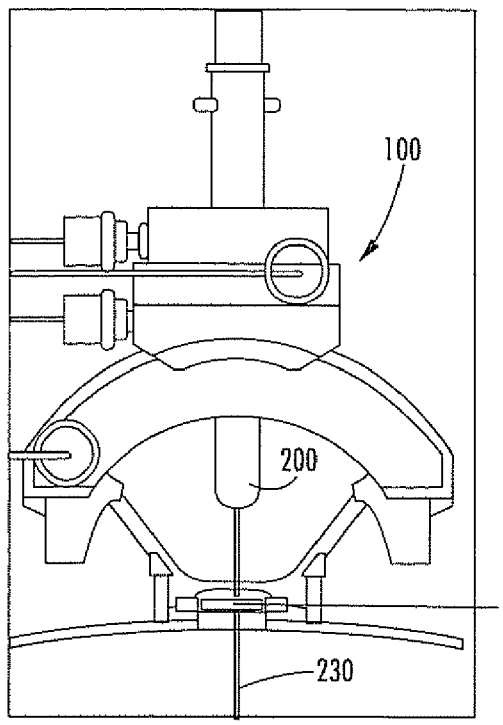
Figure 28F:
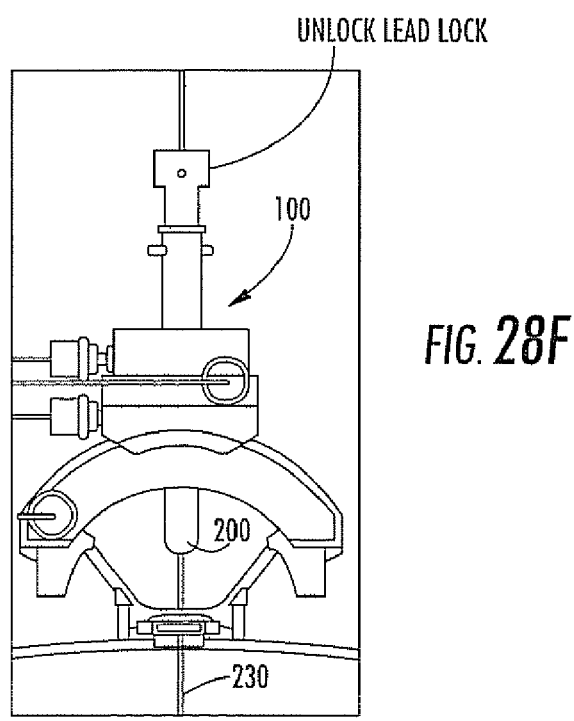
Figure 28G:
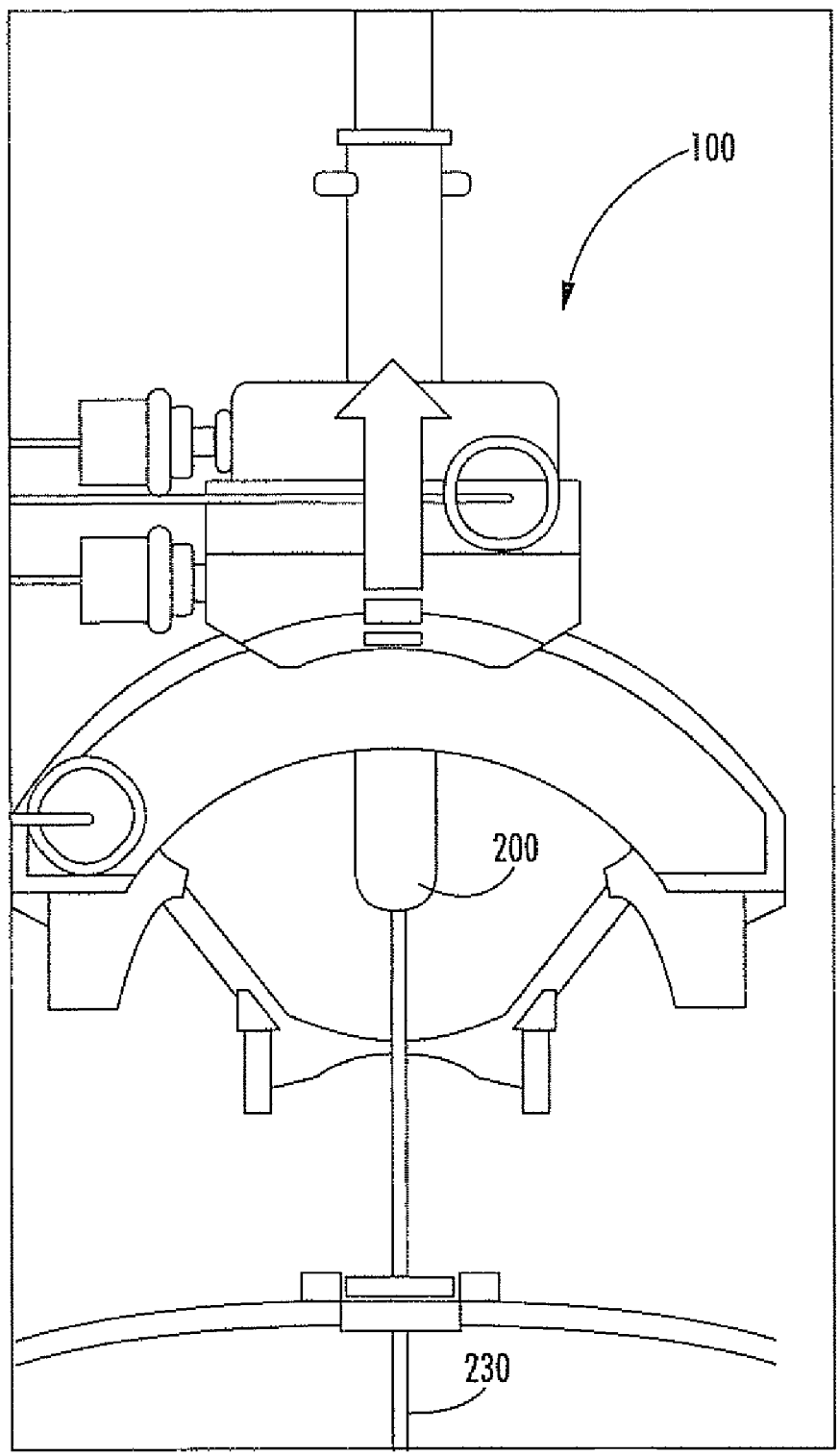

FIGS. 28A-28G are side view, schematic illustrations of the trajectory frame 100 illustrating an exemplary series of operations for the insertion of interventional devices within the body of a patient via the targeting cannula 200. In FIG. 28A, the locking mechanism 220, depth stop 210, and removable sheath 212 are positioned within the targeting cannula 200. In FIG. 3028B, an interventional device, e.g., lead 230, is inserted within the sheath 212 and into the brain of the patient. The locking mechanism 220 secures the lead against axial movement (FIG. 28C). The targeting cannula 200 is then retracted (FIGS. 28D-28E). The locking mechanism 220 is unlocked (FIG. 28F) and the frame 100 is removed from the skull of the patient (FIG. 28G).

Figure 13A:
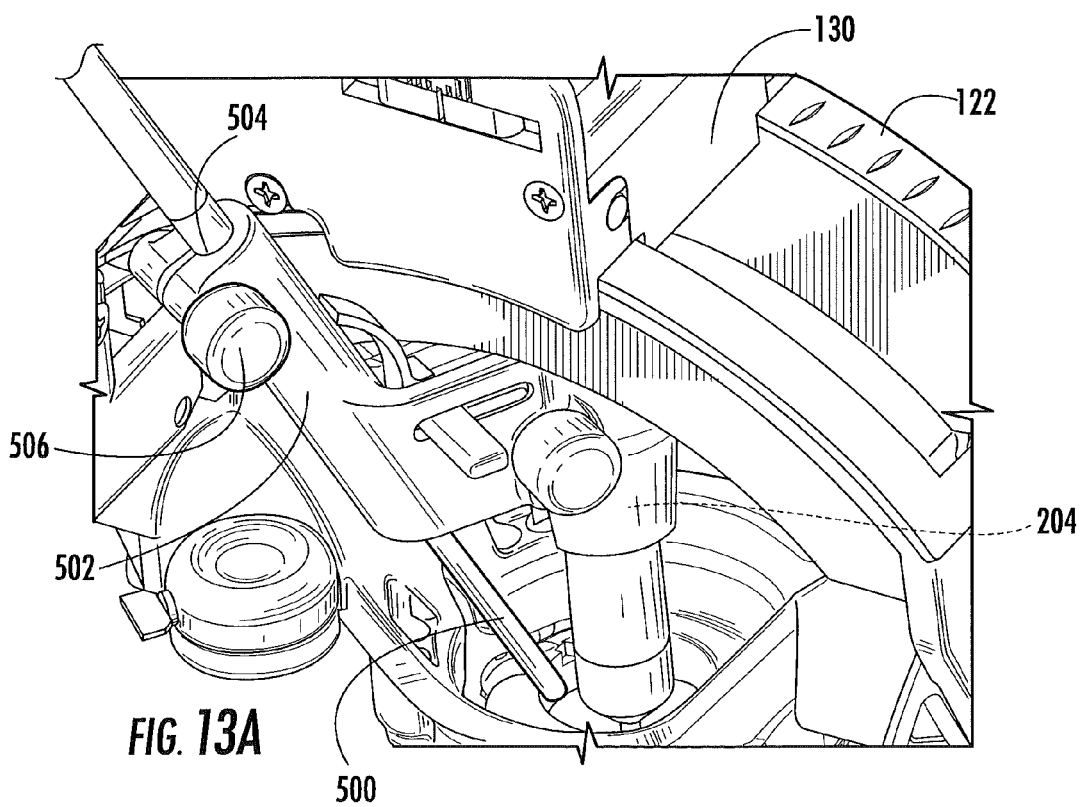
FIGS. 13A-13B illustrate an imaging device mounted to the frame of FIG. 3A so as to view a burr hole, according to some embodiments of the present invention.

In some embodiments of the present invention, an imaging device (e.g., a fiber scope/imaging device with visual access to the burr hole 10 and/or trajectory frame 100 in communication with a camera and display in a clinician workstation) 500 for viewing the burr hole 10 is removably secured to the frame 100 or to the targeting cannula tubular member 204 via a bracket 502. For example, as illustrated in FIG. 13A, a bracket 502 is secured to the targeting cannula tubular member 204. The illustrated bracket 502 is configured to adjustably slide axially along the tubular member 204 for positioning. The illustrated bracket 502 includes a sleeve 504 that is configured to slidably receive an imaging device 500 therein.

Figure 13B:
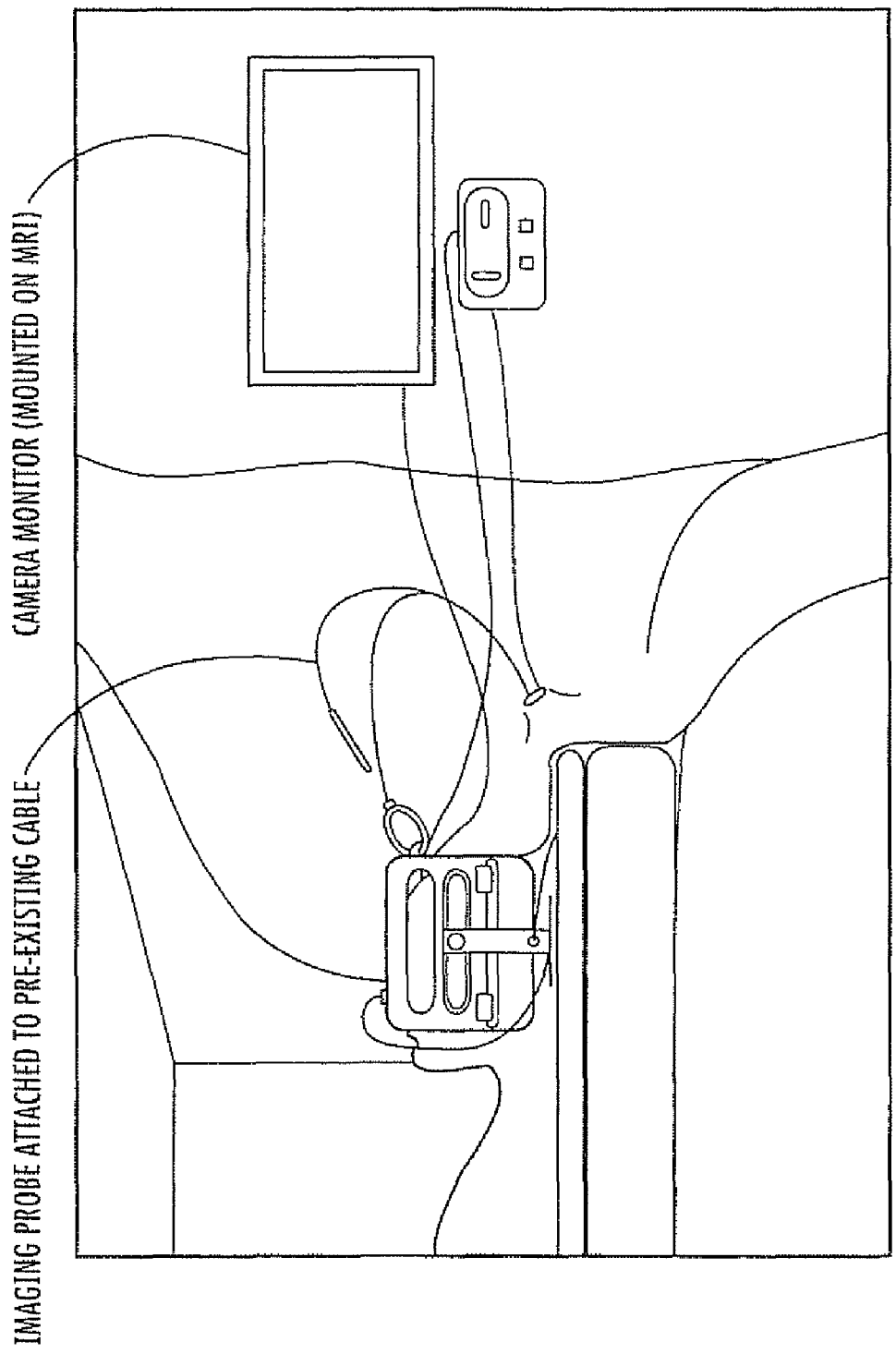

Threaded locking device 506 is configured to secure the imaging device 500 in position within the sleeve 504 for positioning of the imaging device 500 relative to the body of a patient. A clinician views images captured by the imaging device 500 via a monitor, as illustrated in FIG. 13B.

Figure 29:
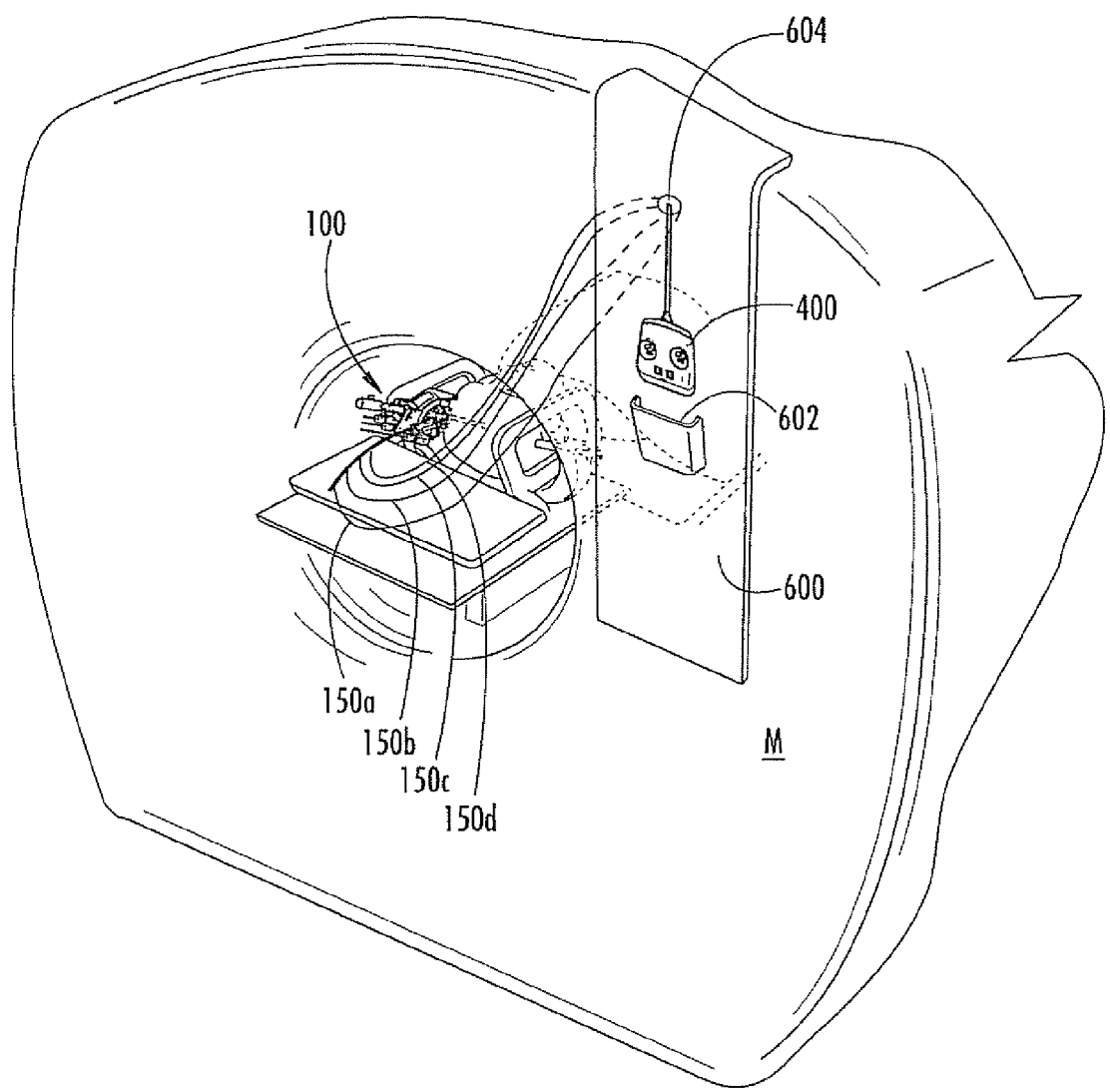
FIG. 29 illustrates a drape configured to be positioned adjacent to a patient and that has a pocket configured to removably receive the remote control unit of FIGS. 9 and 10A-10C.

In the illustrated embodiment of FIG. 29, a sterile drape 600 is provided for holding the remote control unit 400. The drape 600 is configured to be positioned near the body of a patient and includes a pocket 602 configured to removably receive the remote control unit 400 therein. The drape 600 also includes an aperture 604 through which the cables 150a-150b extend from the remote control unit 400 to the frame 100. In the illustrated embodiment, the drape 600 is attached to the magnet housing M of an MRI scanner system.

Figure 30:
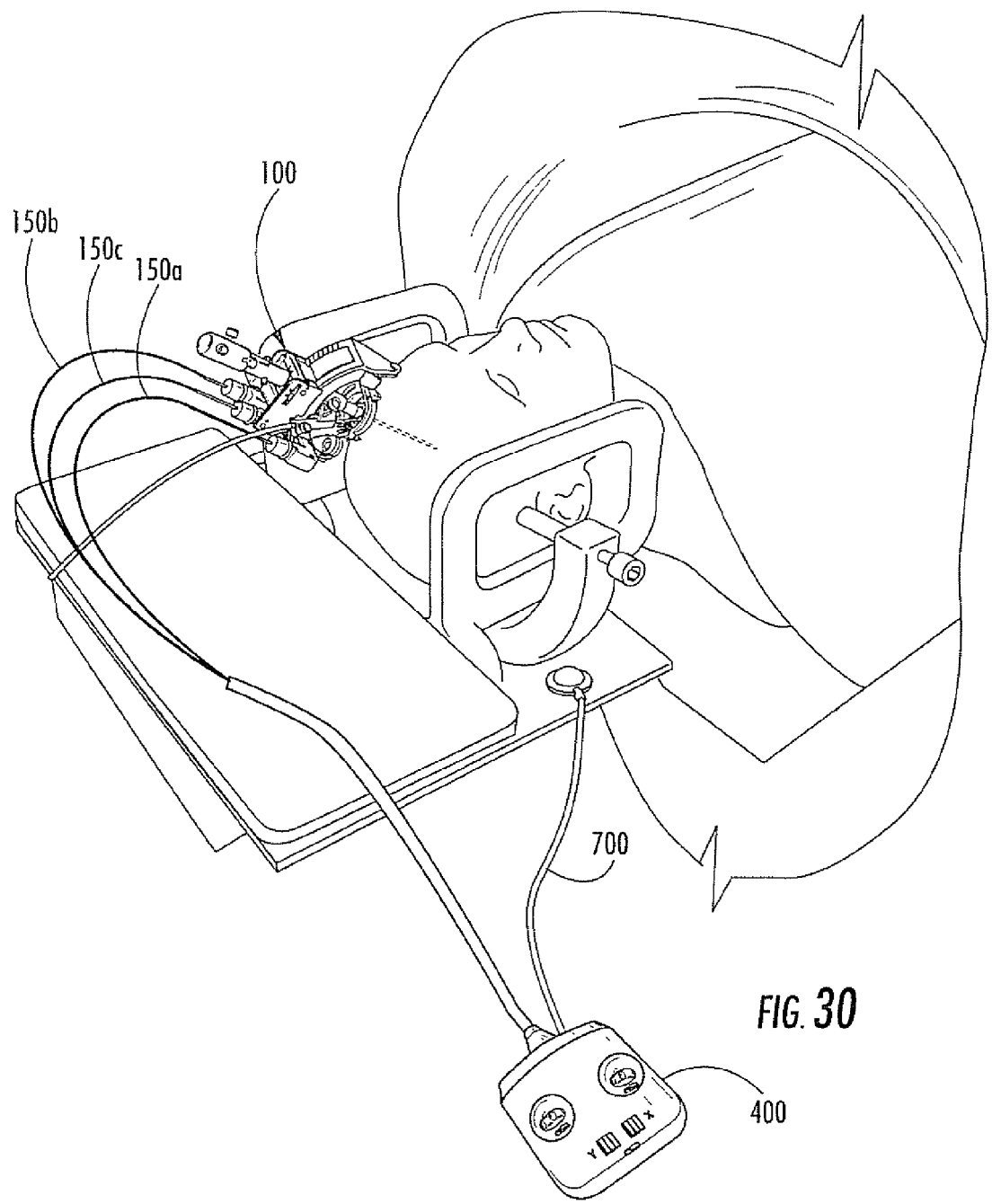
FIG. 30 illustrates a safety lanyard according to some embodiments of the present invention, wherein the safety lanyard is attached to the remote control unit of FIGS. 9 and 10A-10C and to a rigid object to prevent inadvertent detachment of the control cables.

In some embodiments, the control cables 150a-150d are configured to have a limited length. Accordingly, as illustrated in FIG. 30, a safety lanyard 700 may be attached to the remote control unit 400 and to a rigid object to prevent inadvertent detachment of the control cables 150a-150d from the frame actuators 140a-140d caused by moving the remote control unit 400 too far from the frame 100.

Operations associated with a typical surgical procedure using the trajectory frame 100, according to some embodiments of the present invention, will now be described. These operations relate to deep brain stimulation procedures. Embodiments of the present invention are not limited to use with deep brain stimulation procedures, however.

Initially, a patient is placed within an MR scanner and MR images are obtained of the patient's head that visualize the patient's skull, brain, fiducial markers and ROI (region of interest or target therapeutic site). The MR images can include volumetric high-resolution images of the brain. To identify the target ROI, certain known anatomical landmarks can be used, i.e., reference to the AC, PC and MCP points (brain atlases give the location of different anatomies in the brain with respect to these point) and other anatomical landmarks. The location of the burr hole 10 may optionally be determined manually by placing fiducial markers on the surface of the head or programmatically by projecting the location in an image.

Images in the planned plane of trajectory are obtained to confirm that the trajectory is viable, i.e., that no complications with anatomically sensitive areas should occur. The patient's skull is optically or manually marked in one or more desired locations to drill the burr hole. The burr hole 10 is drilled and a burr hole ring 12 is affixed to the skull overlying the burr hole.

The trajectory frame 100 is then fixed to the skull of the patient and the targeting cannula 200 is properly fitted thereto. A localization scan is obtained to determine/register the location of the targeting cannula 200, in direct orientation of the trajectory frame 100. The settings to which the trajectory frame 100 should be adjusted are electronically determined so that the targeting cannula 200 is in the desired trajectory plane. Frame adjustment calculations are provided to a clinician who can manually or electronically adjust the orientation of the frame 100. The desired trajectory plane is confirmed by imaging in one or more planes orthogonal to the desired trajectory plane.

Once the targeting cannula 200 has the desired trajectory plane, the multipurpose probe 217 and delivery sheath 212 are advanced through the targeting cannula 200. The advancement of the probe 217 is monitored by imaging to verify that the probe will reach the target accurately. If the probe 217 and delivery sheath 212 are at the desired target, the sheath is left in place and the probe 217 is removed. The sheath 212 will now act as the delivery cannula for the implantable lead 230.

If the probe 217 and delivery sheath 212 are not at the desired/optimal location, a decision is made as to where the probe 217 and delivery sheath 212 need to be. The trajectory frame 100 is adjusted accordingly via the actuators 140a-140d and the probe 217 and delivery sheath 212 are re-advanced into the brain. Once the probe 217 and delivery sheath 212 are at the desired location, the probe 217 is removed and the delivery sheath is left in place. The lead 230 is then advanced to the target location using the sheath 212 as a guide. The location of the lead is confirmed by reviewing an image, acoustic recording and/or stimulation. The sheath 212 is then removed, leaving the lead in place.

It is contemplated that embodiments of the invention can provide an integrated system 50 that may allow the physician to place the interventional device/leads accurately and in short duration of time. In some embodiments, once the burr hole is drilled, and the trajectory frame is fixed to the skull; the trajectory frame is oriented such that the interventional device advanced using the trajectory frame follows the desired trajectory and reaches the target as planned in preoperative setup imaging plans. As described herein, the system 50 can employ hardware and software components to facilitate an automated or semiautomated operation to carry out this objective.

Figure 33:
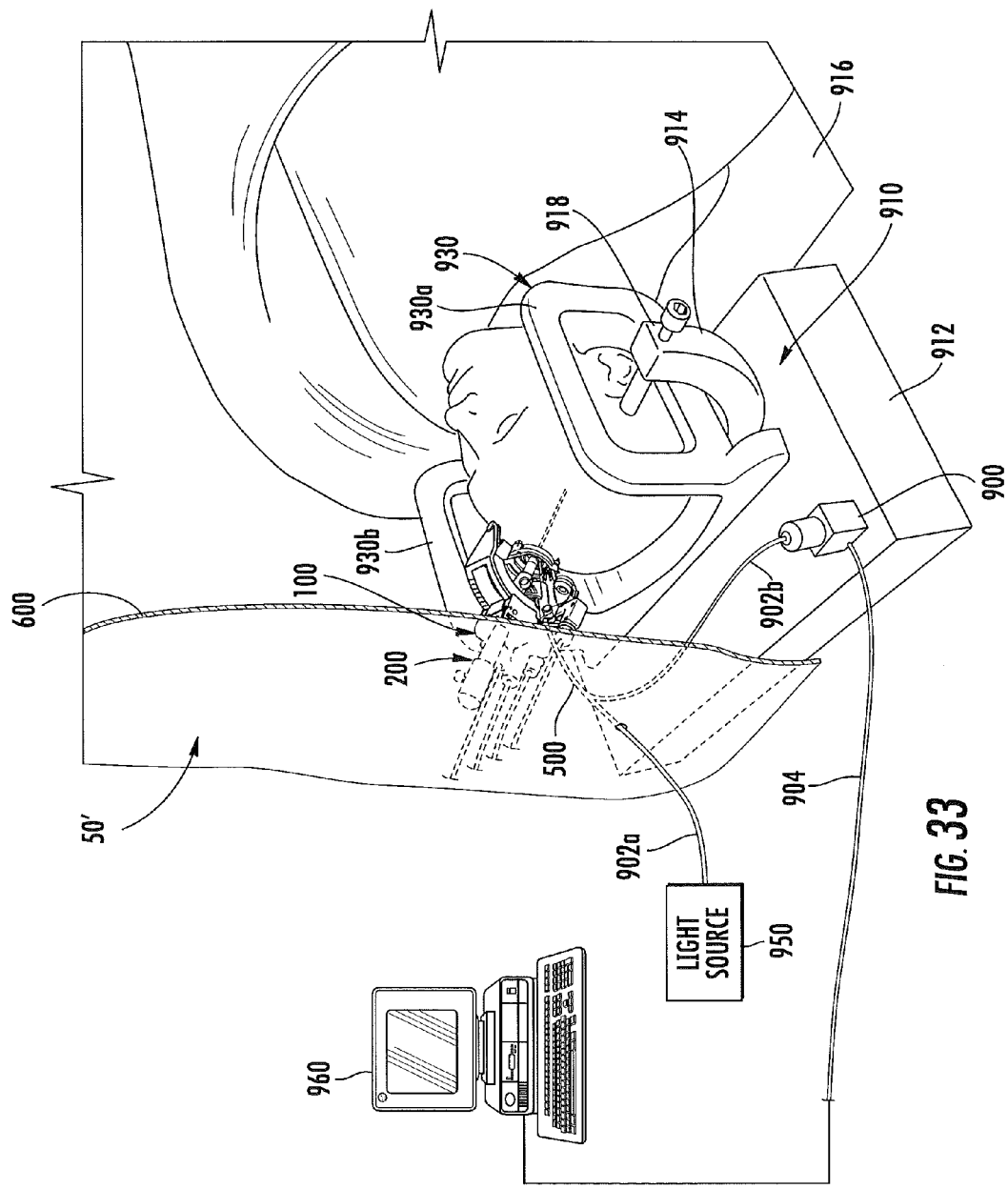
FIG. 33 is a perspective view of an MRI-guided interventional system including a frame and targeting cannula secured to a patient, and including an imaging device, according to some embodiments of the present invention.

Referring now to FIG. 33, an MRI-guided interventional system 50', according to some embodiments of the present invention is illustrated. The illustrated MRI-guided interventional system 50' includes a trajectory frame 100 having a targeting cannula 200 associated therewith, as described above. The frame 100 is secured to the skull of a patient, as described above. The illustrated system 50' includes an imaging device 500 secured to the frame 100 and coupled to an MRI-compatible camera 900 positioned proximate to a patient. The imaging device 500 includes a lens (not shown), and an optical fiber cable that includes one or more optical fibers for providing light from a light source 950, and at least about five thousand (5,000) optical fibers for providing an image to camera 900. The lens is in optical communication with the optical fibers and facilitates obtaining a focused image, as would be understood by those skilled in the art. The imaging device 500 is secured to the frame 100 and, more specifically, as shown in FIG. 13A, to the targeting cannula tubular member 204 (FIG. 3A) via a bracket 502 positioned such that the imaging device 500 has a local, small field of view visual access to a burr hole 10 in the skull of a patient. Still referring to FIG. 13A, the illustrated bracket 502 is configured to adjustably rotate around the tubular member 204 for positioning. The illustrated bracket 502 includes a sleeve 604 that is configured to slidably receive the imaging device 500 therein. Threaded locking device 506 is configured to secure the imaging device 500 in position within the sleeve 504 for positioning of the imaging device 500 relative to the body of a patient.

As shown in FIG. 33, the illustrated system 50' also includes a head support assembly 910 with a head coil apparatus 930 attached thereto. The illustrated head support assembly 910 includes a base 912 and a head support frame 914. The base 912 and head support frame 914 may be an integral unit, or may be separate components. The base 912 is secured to the gantry 916 associated with an MRI scanner 918. Embodiments of the present invention, however, are not limited to the illustrated base 912, or to the illustrated head coil 930.

The illustrated head support frame 914 includes a pair of elongated arms 918 that extend outwardly from the base 912 in adjacent, spaced-apart relationship to form an area for receiving the head of a patient. Head support frames according to embodiments of the present invention may have various structural configurations, without limitation, and are not limited to the illustrated embodiment.

The illustrated head support assembly 910 includes a head coil apparatus 930 that is positioned proximate to the head support frame 914. The head coil apparatus 930 has a substantially open-face, U-shaped configuration with spaced-apart leg portions 930a, 930b having free ends. The head coil apparatus 930 is positioned between the head support frame arms 918 such that the free ends of the leg portions 930a, 930b extend upwardly, as illustrated. The head coil apparatus 930 includes a plurality of RF coils along with circuitry associated therewith. An exemplary supplier of RF coils is Midwest RF, LLC., Hartland, Wis. The head coil apparatus 930 is configured to surround at least a portion of a patient's head secured within the head support frame 914. As such, RF coils can be positioned as desired relative to a patient's head in order to pick up sufficient MRI signals of the patients STN or other target deep brain region.

Figure 34:
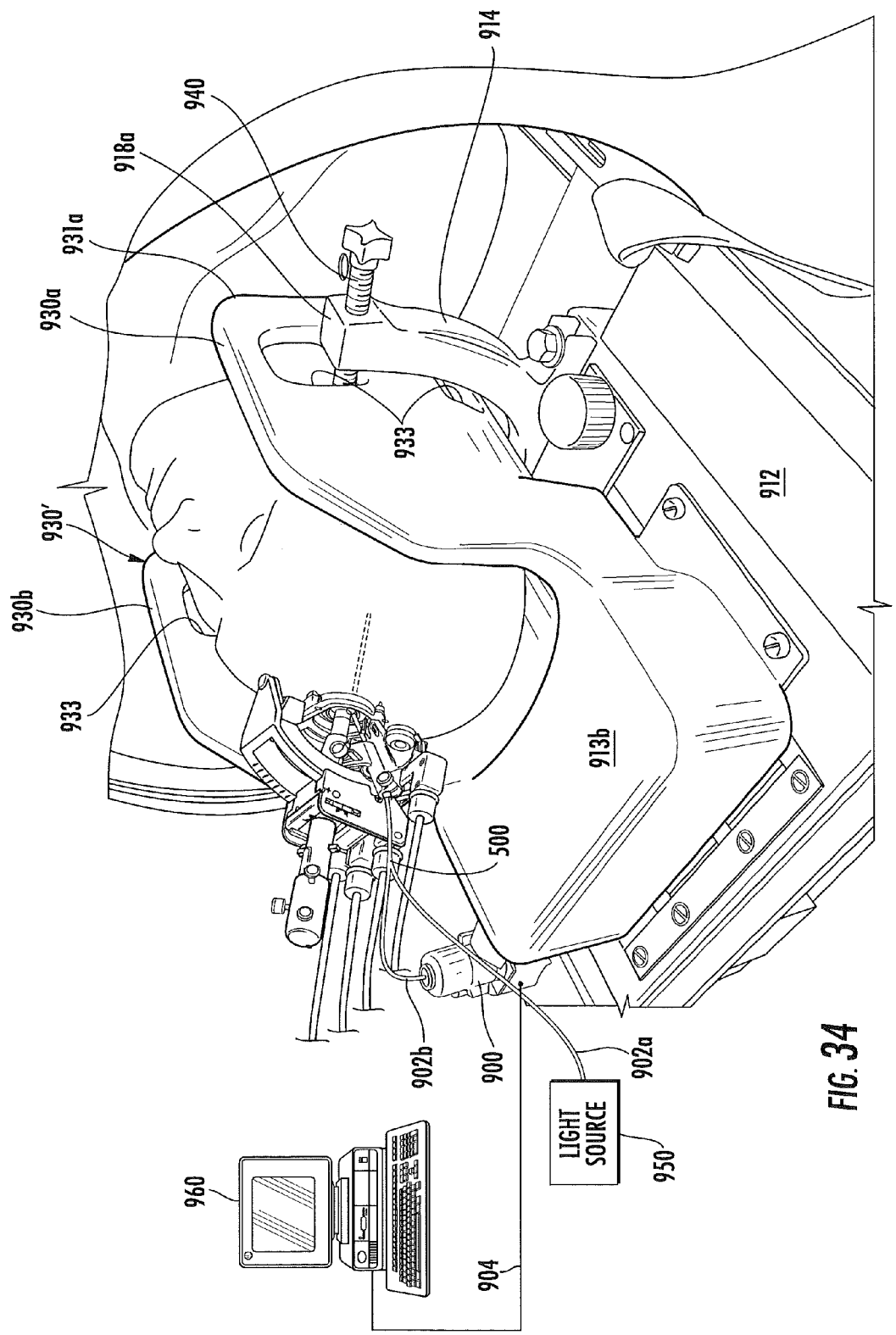
FIG. 34 is a perspective view of an MRI-guided interventional system including a pair of frames and targeting cannulas secured to a patient, each including an imaging device, according to some embodiments of the present invention.

Embodiments of the present invention are not limited to the configuration of the illustrated open-face head coil apparatus 930. Head coil apparatus 930 may have various shapes and configurations, without limitation. For example, FIG. 34 illustrates a head coil apparatus 930', according to other embodiments of the present invention. The illustrated open-ace head coil apparatus 930' is secured to a base 912, which can be removably secured to a gantry associated with an MRI scanner, and which is configured to surround at least a portion of a patient's head within the head support frame 914. The head coil apparatus 930' includes opposite first and second end portions 931a, 931b, with the first end portion 931a positioned within the head support frame 914. The head coil apparatus 930' includes a plurality of spaced-apart access windows 933 formed therein and a plurality of internal RF coils.

Each arm 918 of the head support frame 914 includes a respective free end 918a. A head engagement rod 940 is adjustably associated near each respective arm free end 918a. The head engagement rods 940 are configured to engage a patient's head within the head support frame 914. Additional head engagement rods may also be associated with the head support frame 914.

In the illustrated embodiments of FIGS. 33-34, an MRI-compatible camera 900 (e.g., digital camera capable of acquiring still images, streaming images, etc.) is attached to the base 912. A suitable MRI compatible camera is available from MRC Systems GmbH, Heidelberg, Germany. The illustrated imaging device 500 has a "Y" configuration with leg portions 902a, 902b. The imaging device 500 typically can include between about five thousand (5,000) and thirty thousand (30,000) strands of optical fibers in portion 902b for providing an image to the camera 900. However, embodiments of the present invention are not limited to this range of optical fibers; other numbers of optical fibers are possible. The imaging device 500 includes connectors for coupling the imaging device to a light source/light source cable and to the camera 900.

A remote light source 950 is configured to provide illumination for the imaging device 500. The imaging device can include one or more strands of optical fibers (or a light tube, pipe, etc.) in portion 902a for providing light to the area of interest that is to be imaged. The imaging device 500 and all connectors associated therewith are MRI-compatible. The imaging device 500 moves with the head support assembly 910 as a patient is moved into the bore of the magnet, without requiring long lengths of multi-strand fiber optic cable, thus providing a more economic configuration.

Prior to the present invention, cameras were utilized to provide a wide field of view during MRI-guided procedures. The imaging device 500 of the present invention allows a small field of view at the location of the body of a patient where an MRI-guided procedure is taking place, such as the burr hole 10 in the skull of a patient.

The imaging device 500 can have various lengths. In some embodiments, the imaging device 500 has a length of between about four inches and thirty-six inches (4"-36"). The imaging device 500 can be single-use (e.g., disposable after use with a patient). In the illustrated embodiment, the imaging device 500 extends through a sterile drape 600.

A display output module 960 (e.g., a PC or other computing device with a display) can be coupled to the camera 900, via cable 904, for receiving electrical signals therefrom and for displaying images corresponding thereto. As such, a physician/clinician can view images captured by the imaging device 500 via display output module 960.

Figure 35:
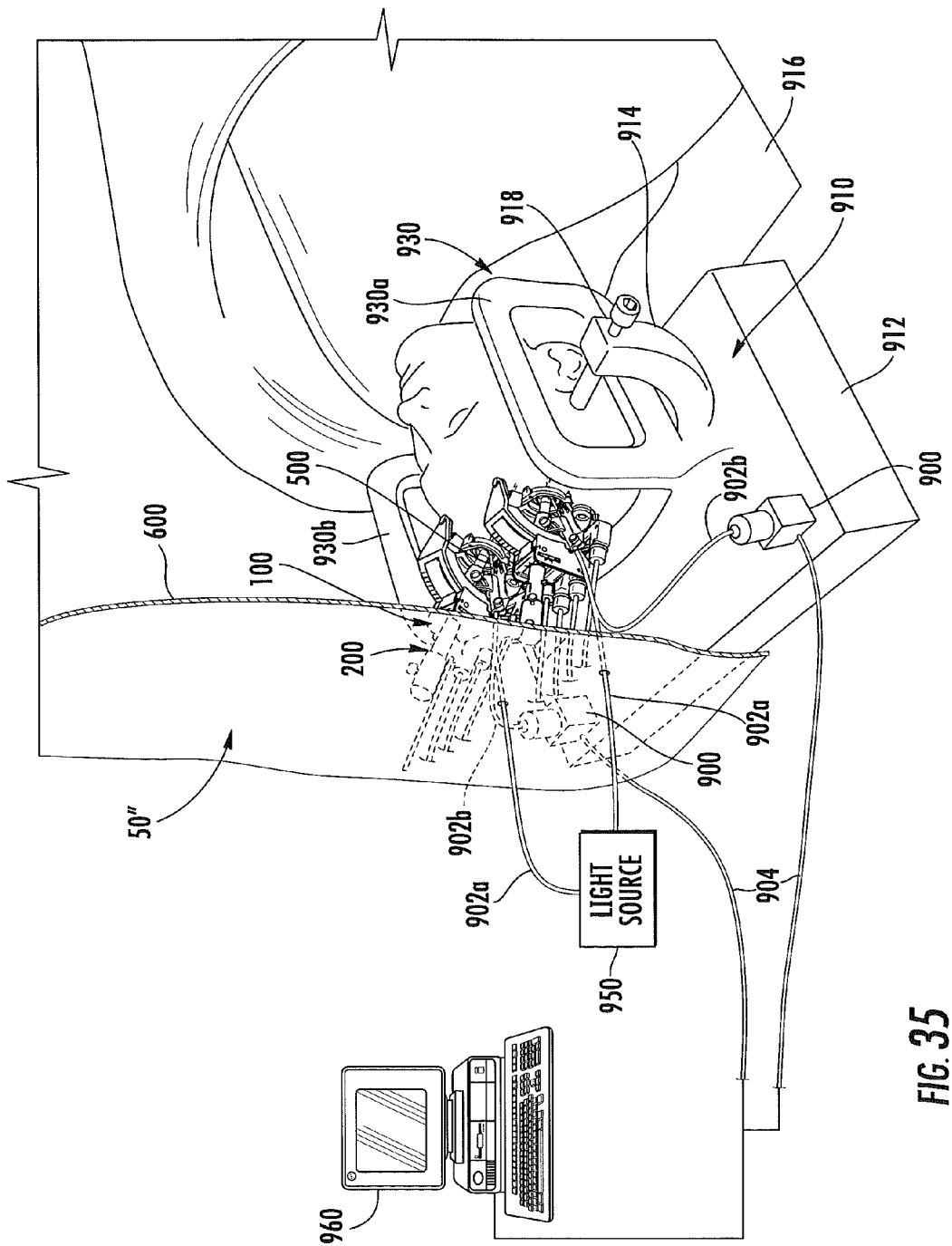
FIG. 35 is a perspective view of an MRI-guided interventional system including a frame and targeting cannula secured to a patient, and including an imaging device, according to other embodiments of the present invention.

Referring to FIG. 35, an MRI-guided interventional system 50", according to other embodiments of the present invention, is illustrated. The system 50" is identical to system 50' described above with respect to FIG. 33, with the addition of a second targeting frame 100, a second imaging device 500, and a second camera 900 for bilateral procedures.

Figure 36:
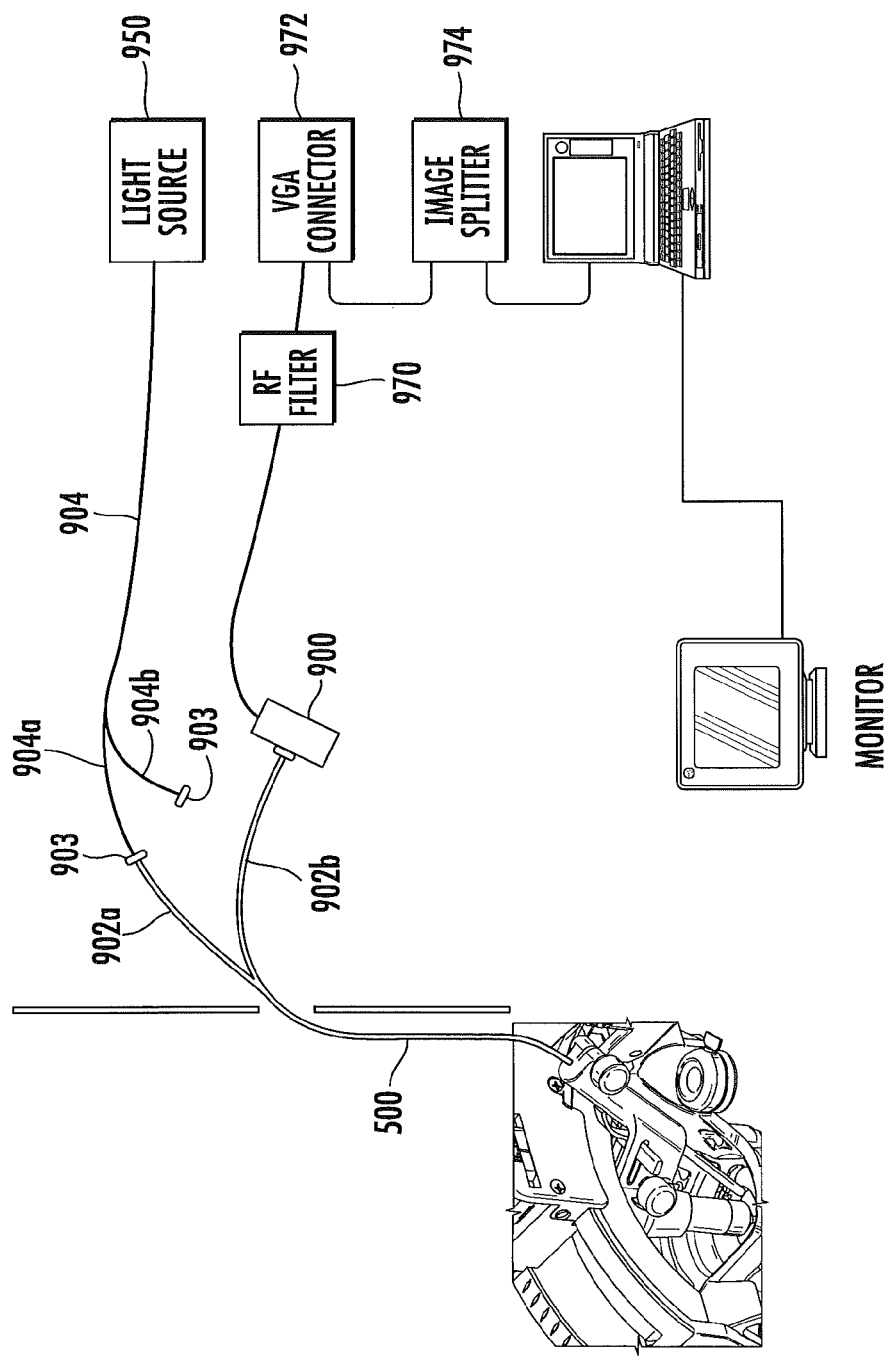
FIG. 36 is a schematic illustration of an MRI-guided interventional system including an imaging device, according to some embodiments of the present invention.

FIG. 36 is a schematic illustration of an MRI-guided interventional system including an imaging device 500 according to another embodiment of the present invention. The imaging device 500 has a "Y" configuration with leg portions 902a and 902b, as illustrated. The light source 950 has a light cable 904 extending therefrom that has a "Y" configuration with leg portions 904a and 904b. The light cable 904 can be an optical fiber cable with one or more optical fibers. The light cable can also be a light tube or pipe. Leg portions 902a and 904a are coupled together via connector 903. The light cable leg portion 904b can be utilized by another imaging device 500, for example in a bi-lateral procedure. In the illustrated embodiment, an RF filter 970 is provided between the MRI-compatible camera 900 and display monitor 960 in order to reduce the effects of MRI signals. A VGA converter 972 and image splitter 974 may also be provided, as illustrated.

The workflow steps described herein may be carried out in a different manner, in a different order and/or with other workflow steps or may omit some or replace some workflow steps with other steps. For example, the frame 100 can be mounted and assembled in a different order than that set forth above. According to some embodiments, the frame 100 is mounted on the patient and assembled as follows. The burr hole is formed. The base 110 is then mounted on the head about the burr hole. A burr hole ring is then mounted on the burr hole through the access opening 112. According to some embodiments, the access opening 112 is sized and shaped to prevent contact between the burr hole ring and the base 110 when both are mounted on the patient's head. The yoke 120 is then mounted on the base 110 (e.g., in the manner described above). According to some embodiments, the yoke 120 is removed from the base 110 after the interventional procedure is executed using the frame 100 in order to facilitate access to the screws securing the base 110 to the head. The screws can then be removed to dismount the base 110 from the head.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention That which is claimed is:

1. An MRI-guided interventional system, comprising:
   a frame configured to be secured to the body of a patient, wherein the frame includes a cooperating targeting cannula that is configured to guide placement of an interventional device through a burr hole in a patient's skull in vivo;
   a head support apparatus;
   an MRI-compatible camera proximate to the head support apparatus; and
   an MRI-compatible imaging device having one end attached to the frame to provide a local field of view of the burr hole, and an opposite end in communication with the camera.

2. The system of claim 1, wherein the imaging device is removably secured to the frame via a bracket, and wherein the bracket comprises a sleeve configured to slidably receive the imaging device therein.

3. The system of claim 1, wherein the targeting cannula is slidably secured within a tubular guide attached to the frame, wherein the imaging device is removably secured to the tubular guide via a bracket, and wherein the bracket comprises a sleeve configured to slidably receive the imaging device therein.

4. The system of claim 1, further comprising a display output module coupled to the camera for receiving electrical signals therefrom and for displaying images corresponding thereto.

5. An MRI-guided interventional system, comprising:
   a head support assembly for immobilizing the head of a patient during an MRI-guided procedure, comprising:
   a base configured to be removably secured to a gantry;
   a head support frame attached to the base, comprising a pair of elongated arms extending outwardly in adjacent, spaced-apart relationship;
   a pair of head engagement rods, wherein each rod is adjustably associated with a respective arm, and wherein the rods are configured to engage a patient's head within the head support frame; and
   a longitudinally extending head coil apparatus positioned proximate to the head support frame and configured to surround at least a portion of a patient's head, wherein the head coil apparatus comprises a plurality of spaced-apart RF coils;
   a targeting frame configured to be secured to the skull of a patient, wherein the frame includes a cooperating targeting cannula that is configured to guide placement of an interventional device through a burr hole in a patient's skull in vivo;
   an MRI-compatible camera proximate to the head support assembly; and
   an MRI-compatible imaging device having one end attached to the targeting frame to provide a local field of view of the burr hole, and an opposite end in communication with the camera.

6. The system of claim 5, wherein the head coil apparatus has an open-face, substantially U-shaped configuration with spaced-apart leg portions having free ends, wherein the head coil apparatus is positioned between the head support frame arms such that the leg portion free ends extend upwardly.

7. The system of claim 5, wherein the head coil apparatus is adjustable along a longitudinal direction relative to the head support frame.

8. The system of claim 5, wherein the head coil apparatus has an open-face, substantially U-shaped configuration and comprises a plurality of spaced-apart access windows formed therein.

9. The system of claim 5, wherein the camera is attached to the base adjacent the head coil apparatus.

10. An MRI-guided interventional system, comprising:
    a pair of targeting frames configured to be secured to the body of a patient in adjacent, spaced-apart relationship, wherein each frame includes a cooperating targeting cannula that is configured to guide placement of an interventional device through a burr hole in a patient's skull in vivo;
    a head support apparatus;
    a pair of MRI-compatible cameras proximate to the head support apparatus; and
    a pair of MRI-compatible imaging devices, each having one end attached to a respective targeting frame to provide a local field of view of a respective burr hole, and each having an opposite end in communication with a respective camera.

11. The system of claim 10, further comprising a display output module coupled to the cameras for receiving electrical signals therefrom and for displaying images corresponding thereto.

12. The system of claim 1, wherein the imaging device comprises one or more optical fibers for providing light from a light source and at least about five thousand (5,000) optical fibers for providing an image to the camera.

13. The system of claim 5, wherein the imaging device comprises one or more optical fibers for providing light from a light source and at least about five thousand (5,000) optical fibers for providing an image to the camera.

14. The system of claim 10, wherein each imaging device comprises one or more optical fibers for providing light from a light source and at least about five thousand (5,000) optical fibers for providing an image to a respective camera.

15. The system of claim 1, wherein the imaging device has a Y configuration with a first leg portion for providing light from a light source and a second leg portion for providing an image to the camera.

16. The system of claim 5, wherein the imaging device has a Y configuration with a first leg portion for providing light from a light source and a second leg portion for providing an image to the camera.

17. The system of claim 10, wherein each imaging device has a Y configuration with a first leg portion for providing light from a light source and a second leg portion for providing an image to a respective camera.

18. The system of claim 3, wherein the bracket comprises a locking device configured to secure the imaging device in position within the sleeve for positioning of the imaging device relative to the body of a patient.

19. The system of claim 5, wherein the imaging device is removably secured to the frame via a bracket, wherein the bracket comprises a sleeve configured to slidably receive the imaging device therein and a locking device configured to secure the imaging device in position within the sleeve for positioning of the imaging device relative to the body of a patient.

20. The system of claim 10, wherein each imaging device is removably secured to a respective frame via a bracket, wherein each bracket comprises a sleeve configured to slidably receive a respective imaging device therein and a locking device configured to secure the respective imaging device in position within the sleeve for positioning of the respective imaging device relative to the body of a patient.

* * * * *

UNITED STATES PATENT AND TRADEMARK OFFICE
CERTIFICATE OF CORRECTION

PATENT NO. : 8,208,993 B2
APPLICATION NO. : 12/237033
DATED : June 26, 2012
INVENTOR(S) : Piferi et al.

It is certified that error appears in the above-identified patent and that said Letters Patent is hereby corrected as shown below:

In the Specifications:
Column 22, Line 49: Please correct "In FIG. 3028B," to read -- In FIG 28B, --

Column 24, Line 48: Please correct "sleeve 604 that" to read -- sleeve 504 that --

Signed and Sealed this
Fourth Day of March, 2014

Michelle K. Lee
*Deputy Director of the United States Patent and Trademark Office*